US010550201B2

(12) United States Patent
Peterson et al.

(10) Patent No.: US 10,550,201 B2
(45) Date of Patent: Feb. 4, 2020

(54) ANTIBODY-NANOPARTICLE CONJUGATES FOR THE TREATMENT OF DRUG ABUSE

(71) Applicants: BioVentures, LLC, Little Rock, AR (US); Eric C. Peterson, Little Rock, AR (US); Nisha Nanaware-Kharade, Little Rock, AR (US); Guillermo Gonzalez, III, Little Rock, AR (US)

(72) Inventors: Eric C. Peterson, Little Rock, AR (US); Nisha Nanaware-Kharade, Little Rock, AR (US); Guillermo Gonzalez, III, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 239 days.

(21) Appl. No.: 14/775,227

(22) PCT Filed: Mar. 13, 2014

(86) PCT No.: PCT/US2014/025767
§ 371 (c)(1),
(2) Date: Sep. 11, 2015

(87) PCT Pub. No.: WO2014/160075
PCT Pub. Date: Oct. 2, 2014

(65) Prior Publication Data
US 2016/0030593 A1 Feb. 4, 2016

Related U.S. Application Data

(60) Provisional application No. 61/779,821, filed on Mar. 13, 2013.

(51) Int. Cl.
*A61K 39/395* (2006.01)
*C07K 16/44* (2006.01)

(52) U.S. Cl.
CPC ........ *C07K 16/44* (2013.01); *C07K 2317/622* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,141,850 A | 8/1992 | Cole et al. |
| 5,160,701 A | 11/1992 | Brown, III et al. |
| 5,328,828 A | 7/1994 | Hu et al. |
| 5,415,994 A | 5/1995 | Imrich et al. |
| 5,451,504 A | 9/1995 | Fitzpatrick et al. |
| 5,545,806 A | 8/1996 | Lonberg et al. |
| 5,545,807 A | 8/1996 | Surani et al. |
| 5,559,041 A | 9/1996 | Kang et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 2008/0125579 A1 | 5/2008 | Owens et al. |

FOREIGN PATENT DOCUMENTS

WO 2014160075 A1 10/2014

OTHER PUBLICATIONS

Shao et al., International Journal of Nanomedicine, 2011, vol. 6, pp. 3361-3372.*
Hardin, J. et al., "Pharmacodynamics of a Monoclonal Antiphencyclidine Fab with Broad Selectivity for Phencyclidine-Like Drugs," JPET, 1998, pp. 1113-1122, vol. 285, No. 3.
Kabat, E. et al., "Identical V region amino acid sequences and segments of sequences in antibodies of different specificities. Relative contributions of VH and VL genes, minigenes, and complementarity-determining regions to binding of antibody-combining sites," J. Immunol., Sep. 1, 1991, pp. 1709-1719, vol. 147, No. 5.
Kelley, R. et al., "Antigen Binding Thermodynamics and Antiproliferative Effects of Chimeric and Humanized anti-p185HER2 Antibody Fab Fragments," Biochem., 1992, pp. 5434-5441, vol. 31.
Laurenzana, E. et al., "Treatment of Adverse Effects of Excessive Phencyclidine Exposure in Rats with a Minimal Dose of Monoclonal Antibody," JPET, 2003, pp. 1092-1098, vol. 306, No. 3.
Mcmillan, D. et al., "Structure-Activity Relationships of Arylcyclohexylamines as Discriminative Stimuli in Pigeons," JPET, 1988, pp. 1086-1092, vol. 247, No. 3.
Lund, B. et al., "Vaccination of cattle with attenuated rinderpest virus stimulates CD4+ T cell responses with broad viral antigen specificity," J. Gen. Viral., 2000, pp. 2137-2146, vol. 81, Great Britain.
Owens, S. et al., "Antibodies Against Arylcycicohexylamines and Their Similarities in Binding Specificity with the Phencyclidine Receptor," JPET, 1988, pp. 472-478, vol. 246, No. 2.
Pluckthun, A., "Antibody engineering," Curr. Opin. Biotechnol., 1991, pp. 238-246, vol. 2.
Proksch, J. et al., "Pharmacokinetic Mechanisms for Obtaining High Renal Coelimination of Phencyclidine and a Monoclonal Antiphencyclidine Antigen-Binding Fragment of Immunoglobulin G in the Rat," JPET, 1998, pp. 616-624, vol. 287, No. 2.
Proksch, J. et al., "Anti-Phencyclidine Monoclonal Antibodies Provide Long-Term Reductions in Brain Phencyclidine Concentrations during Chronic Phencyclidine Administration in Rats," JPET, 2000, pp. 831-837, vol. 292, No. 3.
Bourne, N. et al., "Dendrimers, a New Class of Candidate Topical Microbicides with Activity against Herpes Simplex Virus Infection," Antimicrob. Agents Chemother., Sep. 2000, pp. 2471-2474, vol. 44, No. 9, American Society for Microbiology.
Brocchini, S. et al., "Disulfide bridge based PEGylation of proteins," Adv. Drug Deilv. Rev., 2008, pp. 3-12, vol. 60, Elsevier B.V.
Brunger, A. et al., "Crystallography & NMR System: A New Software Suite for Macromolecular Structure Determination," Acta Cryst., 1998, pp. 905-921, vol. D54, International Union of Crystallography, Great Britain.
Byrnes-Blake, K. et al., "Pharmacodynamic mechanisms of monoclonal antibody-based antagonism of (+)-methamphetamine in rats," Eur. J. Pharmacol., Feb. 14, 2003, pp. 119-128, vol. 461, Nos. 2-3, Elsevier Science B.V.

(Continued)

*Primary Examiner* — Yunsoo Kim
(74) *Attorney, Agent, or Firm* — Polsinelli PC

(57) ABSTRACT

The present invention generally relates to an antibody composition including antibodies conjugated to nanoparticles. The antibody composition may be used in methods to treat drug use, drug addiction, and effects of drug use.

8 Claims, 35 Drawing Sheets
(18 of 35 Drawing Sheet(s) Filed in Color)
Specification includes a Sequence Listing.

(56) References Cited

OTHER PUBLICATIONS

Carroll, F. et al., "The Synthesis of Haptens and Their Use for the Development of Monoclonal Antibodies for Treating Methamphetamine Abuse," NIH Public Access Author Manuscript, available in PMC Nov. 26, 2010, pp. 1-20, Published in final edited form as: J. Med. Chem., pp. 7301-7309, vol. 52, No. 22.
Celikel, R. et al., "Crystal structures of a therapeutic single chain antibody in complex with two drugs of abuse-methamphetamine and 3,4-methylenedioxymethamphetamine," Protein Sci., 2009, pp. 2336-2345, vol. 18, Wiley-Blackwell.
Daftarian, P. et al., "Peptide-Conjugated PAMAM Dendrimer as a Universal DNA Vaccine Platform to Target Antigen-Presenting Cells," Cancer Res., Dec. 15, 2011, pp. 7452-7462, vol. 71, No. 24, American Association for Cancer Research.
Fishwild, D. et al., "High-avidity human IgGk monoclonal antibodies from a novel strain of minilocus transgenic mice," Nat. Biotech., Jul. 1996, pp. 845-851, vol. 14, Nature Publishing Group.
Gentry, W. et al., "Safety and efficiency of an anti-(+)-methamphetamine monoclonal antibody in the protection against cardiovascular and central nervous system effects of (+)-methamphetamine in rats," International Immunopharmacology, 2006, pp. 968-977, vol. 6, Elsevier B.V.
International Search Report and Written Opinion dated Jul. 11, 2014 from related International Patent Application No. PCT/US2014/025767; 9 pgs.
Jones, P. et al., "Replacing the complementarity-determining regions in a human antibody with those from a mouse," Nature, May 29, 1986, pp. 522-525, vol. 321, Nature Publishing Group.
Kohler, G. et al., "Continuous cultures of fused cells secreting antibody of predefined specificity," Nature, Aug. 7, 1975, pp. 495-497, vol. 256, No. 5517, Nature Publishing Group.
Kubetzko, S. et al., "PEGylation and Multimerization of the Anti-p185HER-2 Single Chain Fv Fragment 4D5: Effects on Tumor Targeting," J. Biol. Chem., Nov. 17, 2006, pp. 35186-35201, vol. 281, No. 46, The American Society for Biochemistry and Molecular Biology, Inc.
Kukowska-Latallo, J. et al., "Nanoparticle Targeting of Anticancer Drug Improves Therapeutic Response in Animal Model of Human Epithelial Cancer," Cancer Res., Jun. 15, 2005, pp. 5317-5324, vol. 65, No. 12, American Association for Cancer Research.
Laurenzana, E. et al., "Functional and Biological Determinants Affecting the Duration of Action and Efficacy of Anti-(+)-methamphetamine Monoclonal Antibodies in Rats," NIH Public Access Author Manuscript, available in PMC Nov. 23, 2010, pp. 1-27, Published in final edited form as: Vaccine, 2009, pp. 7011-7020, vol. 27, No. 50.
Laurenzana, E. et al., "Use of Anti-(+)-Methamphetamine Monoclonal Antibody to Significantly Alter (+)-Methamphetamine and (+)-Amphetamine Disposition in Rats," Drug Metab. Dispos., 2003, pp. 1320-1326, vol. 31, No. 11, The American Society for Pharmacology and Experimental Therapeutics.
Lee, C. et al., "A single dose of doxorubicin-functionalized bow-tie dendrimer cures mice bearing C-26 colon carcinomas," PNAS, Nov. 7, 2006, pp. 16649-16654, vol. 103, No. 45.
Lee, L. et al., "Prolonged Circulating Lives of Single-Chain Fv Proteins Conjugated with Polyethylene Glycol: A Comparison of Conjugation Chemistries and Compounds," Bioconjug. Chem., 1999, pp. 973-981, vol. 10, No. 6, American Chemical Society.
Lonberg, N. et al., "Antigen-specific human antibodies from mice comprising four distinct genetic modifications," Nature, Apr. 28, 1994, pp. 856-859, vol. 368, Nature Publishing Group.
Luo, D. et al., "Poly(ethylene glycol)-Conjugated PAMAM Dendrimer for Biocompatible, High-Efficiency DNA Delivery," Macromolecules, 2002, pp. 3456-3462, vol. 35, No. 9, American Chemical Society.
Marks, J. et al., "By-passing Immunization. Human Antibodies from V-gene Libraries Displayed on Phage," J. Mol. Biol., 1991, pp. 581-597, vol. 222, Academic Press Limited.

Mcmillan, D. et al., "Effects of Murine-Derived Anti-Methamphetamine Monoclonal Antibodies on (+)-Methamphetamine Self-Administration in the Rat," JPET, 2004, pp. 1248-1255, vol. 309, No. 3, The American Society for Pharmacology and Experimental Therapeutics.
Nanaware-Kharade, N. et al., "Therapeutic Anti-Methamphetamine Antibody Fragment-Nanoparticle Conjugates: Synthesis and In Vitro Characterization," NIH Public Access Author Manuscript, available in PMC Sep. 19, 2013, pp. 1-22, Published in final edited form as: Bioconjug. Chem., Sep. 19, 2012, pp. 1864-1872, vol. 23, No. 9.
Neuberger, M., "Generating high-avidity human Mabs in Mice," Nat. Biotechnol., Jul. 1996, p. 826, vol. 14, No. 7, Nature Publishing Group.
Owens, S. et al., "125I Radioimmunoassay of Delta-9-Tetrahydrocannabinol in Blood and Plasma with a Solid-Phase Second-Antibody Separation Method," Clin. Chem., 1981, pp. 619-624, vol. 27, No. 4.
Peer, D. et al., "Nanocarriers as an emerging platform for cancer therapy," Nat. Nanotechnol., Dec. 2007, pp. 751-760, vol. 2, Nature Publishing Group.
Peterson, E. et al., "Monoclonal Antibody Form and Function: Manufacturing the Right Antibodies for Treating Drug Abuse," The AAPS Journal, 2006, pp. E383-E390, vol. 8, No. 2, Article 43.
Peterson, E. et al., "Using Hapten Design to Discover Therapeutic Monoclonal Antibodies for Treating Methamphetamine Abuse," JPET, 2007, pp. 30-39, vol. 322, No. 1, The American Society for Pharmacology and Experimental Therapeutics.
Peterson, E. et al., "Development and Preclinical Testing of a High Affinity Single Chain Antibody against (+)-Methamphetamine," NIH Public Access Author Manuscript, available in PMC Nov. 4, 2009, pp. 1-24, Published in final edited from as: JPET, Apr. 2008, pp. 124-133, vol. 325, No. 1.
Peterson, E. et al., "Designing Immunotherapies to Thwart Drug Abuse," Mol. Interv., Jun. 2009, pp. 119-124, vol. 9, No. 3.
Provenzale, J. et al., "Uses of Nanoparticles for Central Nervous System Imaging and Therapy," AJNR Am. J. Neuroradiol., Aug. 2009, pp. 1293-1301, vol. 30.
Riechmann, L. et al., "Reshaping human antibodies for therapy," Nature, Mar. 24, 1988, pp. 323-327, vol. 332.
Riviere, G. et al., "Spontaneous Locomotor Activity and Pharmacokinetics of Intravenous Methamphetamine and Its Metabolite Amphetamine in the Rat," J. Pharmacol. Exp. Ther., 1999, pp. 1220-1226, vol. 291, No. 3, The American Society for Pharmacology and Experimental Therapeutics.R.
Roopenian, D. et al., "FcRn: the neonatal Fc receptor comes of age," Nat. Rev. Immunol., Sep. 2007, pp. 715-725, vol. 7, Nature Publishing Group.
Sharma, A. et al., "Polyacrylamide gel electrophoresis separation and detection of polyamidoamine dendrimers possessing various cores and terminal groups," J. Chromatogr. A., Jul. 22, 2005, pp. 238-244, vol. 1081, No. 2, Elsevier B.V.
Sharma, A. et al., "A simple polyacrylamide gel electrophoresis procedure for separation of polyamidoamine dendrimers," Electrophoresis, 2003, pp. 2733-2739, vol. 24, No. 16, Wiley-VCH Verlag.
Stevens, M. et al., "Preclinical characterization of an anti-methamphetamine monoclonal antibody for human use," mAbs, Mar./Apr. 2014, pp. 547-555, vol. 6, No. 2, Landes Bioscience.
Thomas, J. et al., "Synthesis and Biosensor Performance of a Near-IR Thiol-Reactive Fluorophore Based on Benzothiazolium Squaraine," Bioconjug. Chem., 2007, pp. 1841-1846, vol. 18, No. 6, American Chemical Society.
Tyssen, D. et al., "Structure Activity Relationship of Dendrimer Microbicides with Dual Action Antiviral Activity," PLoS ONE, Aug. 2010, pp. 1-15, vol. 5, No. 8, e12309.
Verhoeyen, M. et al., "Reshaping Human Antibodies: Grafting an Antilysozyme Activity," Science, Mar. 25, 1988, pp. 1534-1536, vol. 239, No. 4847.
Yang, K. et al., "Tailoring structure-function and pharmacokinetic properties of single-chain Fv proteins by site-specific PEGylation," Protein Eng., 2003, pp. 761-770, vol. 16, No. 10, Oxford University Press.

(56) References Cited

OTHER PUBLICATIONS

Zhang, L. et al., "Nanoparticles in Medicine: Therapeutic Applications and Developments," Clin. Pharmacol. Therapeutics, May 2008, pp. 761-769, vol. 83, No. 5, Nature Publishing Group.

Boas, U. et al., Dendrimers in drug research, Chem. Soc. Rev., 2004, pp. 43-63, vol. 33, No. 1, The Royal Society of Chemistry.

Baum, P. et al., "Single-chain Fv immunoliposomes for the targeting of fibroblast activation protein-expressing tumor stromal cells," J. Drug Target, Jul. 2007, pp. 399-406, vol. 15, No. 6, Informa UK Ltd.

Boerner, P. et al., "Production of antigen-specific human monoclonal antibodies from in vitro-primed human splenocytes," J. Immunol., Jul. 1, 1991, pp. 86-95, vol. 147, No. 1.

Chapman, A. et al., "PEGylated antibodies and antibody fragments for improved therapy: a review," Adv. Drug Deliv. Rev., Jun. 17, 2002, pp. 531-545, vol. 54, No. 4, Elsevier Science B.V., United Kingdom.

Cheng, Y.-C. et al., "Relationship between the inhibition constant (K1) and the concentration of inhibitor which causes 50 per cent inhibition (I50) of an enzymatic reaction," Biochem. Pharmacol., Dec. 1, 1973, pp. 3099-3108, vol. 22, No. 23, Pergamon Press, Great Britain.

Hoogenboom, H. et al., "By-passing Immunisation: Human Antibodies from Synthetic Repertoires of Germline VH Gene Segments Rearranged in Vitro," J. Mol. Biol., Sep. 20, 1992, pp. 381-388, vol. 227, No. 2, Academic Press Limited.

Kozbor, D. et al., "A human hybrid myeloma for production of human monoclonal antibodies," J. Immunol., Dec. 1, 1984, pp. 3001-3005, vol. 133, No. 6.

Kurfurst, M., "Detection and Molecular Weight Determination of Polyethylene Glycol-Modified Hirudin by Staining after Sodium Dodecyl Sulfate-Polyacrylamide Gel Electrophoresis," Anal. Biochem., 1992, pp. 244-248, vol. 200, No. 2, Academic Press, Inc.

Malik, N. et al., "Dendrimers: Relationship between structure and biocompatibility in vitro, and preliminary studies on the biodistribution of 125I-labelled polyamidoamine dendrimers in vivo," J. Control. Release, Mar. 2000, pp. 133-148, vol. 65, Nos. 1-2, Elsevier Science B.V.

Marks, J. et al, "By-Passing Immunization: Building High Affinity Human Antibodies by Chain Shuffling," Nat. Biotechnol., Jul. 1992, pp. 779-783, vol. 10, No. 7, Nature Publishing Company.

McClurkan, M. et al., "Disposition of a Monoclonal Antiphencyclidine Fab Fragment of Immunoglobulin G in Rats," JPET, Sep. 1993, pp. 1439-1445, vol. 266, No. 3, Williams & Wilkins.

Morrison, S., "Success in specification," Nature, Apr. 28, 1994, pp. 812-813, vol. 368, No. 6474.

Plesner, B. et al., "The molar hydrodynamic volume changes of factor VIIa due to GlycoPEGylation," J. Pharm. Biomed. Anal., Jun. 1, 2011, pp. 597-602, vol. 55, No. 3, E;sevier, B.V.

Presta, L., "Antibody engineering," Curr. Op. Struct. Biol., Aug. 1992, pp. 593-596, vol. 2, No. 4, Current Biology Ltd.

\* cited by examiner

FIG. 16

SEQUENCE LISTING

<160> NUMBER OF SEQ ID NOS: 3

<210> SEQ ID NO 1
<211> LENGTH: 18
<212> TYPE: PRT
<213> ORGANISM: Artificial Sequence

```
<220> FEATURE:
<223> OTHER INFORMATION: SYNTHESIZED

<400> SEQUENCE: 1

Gly Gly Gly Gly Pro Gly Gly Gly Ser Gly Gly Pro Gly Gly Gly
 1               5                  10                  15

Gly Ser

<210> SEQ ID NO 2
<211> LENGTH: 242
<212> TYPE: PRT
<213> ORGANISM: Artificial Sequence
<220> FEATURE:
<223> OTHER INFORMATION: SYNTHESIZED

<400> SEQUENCE: 2

Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Val Thr Ser Gly
            20                  25                  30

Tyr Trp Ser Trp Ile Arg Gln Phe Pro Gly Asn Lys Leu Asp Tyr Met
        35                  40                  45

Gly Tyr Ile Ser Tyr Arg Gly Ser Thr Tyr Tyr Asn Pro Ser Leu Lys
    50                  55                  60

Ser Arg Ile Ser Ile Thr Arg Asp Thr Ser Lys Asn Gln Val Tyr Leu
65                  70                  75                  80

Gln Leu Lys Ser Val Ser Ser Glu Asp Thr Ala Thr Tyr Tyr Cys Ser
                85                  90                  95

Tyr Phe Asp Ser Asp Asp Tyr Ala Met Glu Tyr Trp Gly Gln Gly Thr
            100                 105                 110

Ser Val Thr Val Ser Gly Gly Gly Gly Ser Gly Gly Gly Ser Gly
        115                 120                 125

Gly Gly Gly Ser Gln Ile Val Leu Thr Gln Ser Pro Ala Ile Met Ser
    130                 135                 140

Ala Ser Pro Gly Glu Lys Val Thr Leu Thr Cys Ser Ala Ser Ser Ser
145                 150                 155                 160

Val Ser Ser Ser His Leu Tyr Trp Tyr Gln Gln Lys Pro Gly Ser Ser
                165                 170                 175

Pro Lys Leu Trp Ile Tyr Ser Thr Ser Asn Leu Ala Ser Gly Val Pro
            180                 185                 190

Ala Arg Phe Ser Gly Ser Gly Ser Gly Thr Ser Tyr Ser Leu Thr Ile
        195                 200                 205

Ser Ser Met Glu Ala Glu Asp Ala Ala Ser Tyr Phe Cys His Gln Trp
    210                 215                 220

Ser Ser Phe Pro Phe Thr Phe Gly Ser Gly Thr Lys Leu Glu Ile Lys
225                 230                 235                 240

Arg Ala

<210> SEQ ID NO 3
<211> LENGTH: 119
<212> TYPE: PRT
<213> ORGANISM: Artificial Sequence
<220> FEATURE:
<223> OTHER INFORMATION: SYNTHESIZED
```

```
<400> SEQUENCE: 3

Tyr Gln Thr Val Ala Arg Gly Ala Ser Val Lys Met Ser Lys Ala Ser
1               5                   10                  15

Tyr Thr Phe Tyr Trp Met His Val Lys Arg Gln Gly Glu Trp Ile Gly
            20                  25                  30

Tyr Pro Gly Asn Ser Asp Thr Thr Gln Lys Phe Gly Lys Ala Lys Leu
        35                  40                  45

Ala Val Thr Ser Thr Ala Met Glu Ser Leu Thr Asn Ser Val Leu Tyr
        50                  55                  60

Gly Asn Tyr Asp Phe Asp Thr Leu Asp Met Ser Ser Leu Leu Gly Ile
65                  70                  75                  80

Lys Gln Asp Ile Asn Lys Phe Ile Ala His Lys Gly Arg Leu His Tyr
                85                  90                  95

Thr Gln Pro Ile Ser Arg Asp Phe Ser Asn Leu Pro Ile Thr Tyr Leu
            100                 105                 110

Tyr Ala Asn Leu Leu Trp Gly
            115
```

ANTIBODY-NANOPARTICLE CONJUGATES FOR THE TREATMENT OF DRUG ABUSE

CROSS REFERENCE TO RELATED APPLICATIONS

This application claims the priority of PCT Application PCT/US2014/025767, filed Mar. 13, 2014, which claims the priority of U.S. provisional application No. 61/779,321, filed Mar. 13, 2013, each of which is hereby incorporated by reference in its entirety.

GOVERNMENTAL RIGHTS

This invention was made with government support under grants DA026423, DA11560, DA14361, DA018039, and DA05477, awarded by the National Institute on Drug Abuse (NIDA). The government may have certain rights in the invention.

FIELD OF THE INVENTION

The present invention relates to compositions and methods for the treatment of drug abuse in a subject. More particularly, the invention relates to treating the effects of drug abuse and drug addiction in a subject using antibody-nanoparticle conjugates.

BACKGROUND OF THE INVENTION

The socioeconomic impact of (+)-methamphetamine (METH) abuse is of great concern worldwide. Due to its multiple sites of action in the central nervous system (CNS) as well as systemically, it is difficult to attenuate the detrimental effects of METH using a brain receptor antagonist or agonist. Currently, there are no FDA approved medications to treat METH addiction. The available therapies are mainly supportive and involve behavior modification. METH specific antibody-based medications that act as pharmacokinetic (PCKN) antagonists by reducing the concentration of METH in the brain and other crucial organs have shown promise as potential therapeutics. They alter the disposition of METH in the body, thus reducing the associated medical complications. However, the in vivo half-life of these METH specific antibody-based medications is too short to offer longer-term protection from the effects of METH and the active metabolite (+)-amphetamine (AMP).

Accordingly, a need still exists for METH specific therapeutics that could reduce the concentration of METH in the CNS and offer long-term protection from the effects of METH and AMP. Compositions and methods exploiting METH specific antibody based therapies are needed to further medical research and provide improved therapeutic resources for such conditions. The present invention provides compositions and methods for treating conditions associated with drug abuse that offer long-term protection from the effects of METH and AMP.

BRIEF DESCRIPTION OF THE DRAWINGS

The application file contains at least one photograph executed in color. Copies of this patent application publication with color photographs will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

(FIG. 1A) Depicts a schematic of polyamidoamine (PAMAM) dendrimer consisting of a core, three generations of synthesis, and terminal groups. (FIG. 1B) Depicts the structure representative of heterobifunctional polyethylene glycol (PEG) linker with N-hydroxysuccinimide (NHS) ester and maleimide groups with 24 ethylene oxide repeat units [succinimidyl-[(N-maleimidopropionamido)-tetracosaethyleneglycol] ester. (FIG. 1C) Depicts a schematic of scFv6H4Cys (VH, variable heavy region; VL, variable light region; Linker, an 18 amino acid linking region (GGGGPGGGGSGGPGGGGS; SEQ ID NO:1); His6, 6-histidine tag for aiding purification; Cys, engineered cysteine residue for site-specific conjugation.

(FIG. 3A) Depicts UV spectroscopy monitoring of the NHS crosslinking reaction. Representative UV wavelength scans from 220-230 nm of increasing reaction ratios of PEG$_{24}$ to G3 PAMAM dendrimers before and after desalting to remove the NHS groups and unreacted PEG$_{24}$. The solid lines represent the PEG$_{24}$ modified dendrimers before desalting and the dotted lines represent the PEG$_{24}$ modified dendrimers after desalting. (FIG. 3B) Depicts SDS-PAGE reducing gels loaded with reaction products of increasing ratios of PEG$_{24}$ to dendrimer: (lane 1) purified scFv6H4Cys, (lanes 2 and 6) 5:1 PEG$_{24}$:dendrimer reaction ratio, (lanes 3 and 7) 11:1 PEG$_{24}$:dendrimer reaction ratio, (lanes 4 and 8) 16:1 PEG$_{24}$:dendrimer reaction ratio, and (lanes 5 and 9) 32:1 PEG$_{24}$:dendrimer reaction ratio. The left gel panel is stained with coomassie based GelCode Blue stain and the right is stained with PEG-specific iodine stain.

(FIG. 4A) Depicts a representative MALDI-TOF spectrum showing the peaks resolved from a 5:1 PEG$_{24}$:dendrimer reaction. (FIG. 4B) Depicts a plot of the average number of PEG$_{24}$ incorporated per dendrimer versus each reaction ratio as calculated from MALDI-TOF analysis.

(FIG. 5A) Depicts a SDS-PAGE reducing gel from studies of temperature optimization of the PEG$_{24}$ modified dendrimer crosslinking to scFv6H4Cys (dendribodies) reaction: (Lane 1) PEG$_{24}$:dendrimer (reaction ratio 11:1), (Lane 2) purified scFv6H4Cys, (Lane 3) dendribodies, reaction incubated at 10° C., (Lane 4) dendribodies, reaction incubated at 25° C. and (Lane 5) dendribodies, reaction incubated at 37° C. (FIG. 5B) Depicts a SDS-PAGE reducing gel from studies of pH optimization of the PEG$_{24}$ modified dendrimer crosslinking to the scFv6H4Cys (dendribodies): (Lane 1) purified scFv6H4Cys, (Lane 2) PEG$_{24}$:dendrimer (reaction ratio 11:1), dendribodies synthesized in conjugation buffer adjusted at pH 6.2 (Lane 3), 6.4 (Lane 4), 6.6 (Lane 5, 6.8 (Lane 6), 7.0 (Lane 7) and 7.2 (Lane 8).

(FIG. 6A) Graphically illustrates an SEC analysis of dendribodies before purification and DTT reduced scFv6H4Cys. The solid line represents the dendribodies and the dotted line represents scFv6H4Cys. (FIG. 6B) Depicts a Western Blot analysis showing purified scFv6H4Cys (Lane 1), dendribodies before purification (Lane 2) and eluting fractions (Lanes 1-11). This data indicates that the DTT reduced scFv6H4Cys exists in vitro mainly as a monomer shown by a prominent peak at 27 kDa. There was also a trace quantity of dimeric species eluting at approximately 15 mL. The dendribodies elute as a single peak at 184 kDa followed by the peak of unreacted scFv6H4Cys.

(FIG. 7A) Graphically illustrates the separation profile of dendribodies from unreacted $PEG_{24}$:dendrimers and scFv6H4Cys. Peak assignments: (1-3) unreacted $PEG_{24}$: dendrimers, (4-6) dendribodies and (7-15) mixture of dendribodies and unreacted scFv6H4Cys. (FIG. 7B) Depicts an SDS-PAGE analysis of the fractions eluted with imidazole gradient. (FIG. 7C) Depicts an SDS-PAGE analysis of pooled and concentrated elution fractions 4-6.

(FIG. 9A) Depicts the design of anti-METH scFv6H4. (FIG. 9B) Depicts the expression and purification of anti-METH scFv6H4. The inset to (FIG. 9B) shows scFv6H4 one column purification. (Lane 2, expression media; lane 3, flow through; and lane 4, column elution).

(FIG. 11A) Depicts a schematic representation of the dosing regimen used for the in vivo pharmacokinetic studies. (FIG. 11B) Graphically illustrates the average concentration versus time profiles for METH in serum with and without scFv6H4 antibody.

(FIG. 13A) Depicts the time lapse of 1-30 minutes and (FIG. 13B) depicts the time lapse of 60-240 minutes.

(FIG. 15A) Depicts an overall view of the scFv6H4/METH complex. The METH moiety is shown in salmon. The nitrogen of METH is colored blue. The light chain is shown in magenta and the heavy chain in yellow. (FIG. 15B) Depicts the environment of the amide nitrogen of METH (blue) and hydrophilic interactions. There is a strong hydrogen bond between the amide nitrogen and one of the carboxylate oxygen atoms (red) of glutamate 101 from the heavy chain. Additionally, there could be favorable interactions with tyrosine 24 and histidine 89 of the light chain.

FIG. 16 depicts a sequence alignment of two known anti-METH scFv sequences. The sequence is in single letter amino acid notation and numbered according to Kabat et al., 1991. Location of the framework and CDR residues are indicated. Residues that are identical are noted with a (·, dot), and positions in the CDR that do not contain an amino acid are noted with a (-, hash mark). Residue positions that form the METH binding pocket of scFv6H4 are highlighted and the three residues responsible for hydrogen bonding to the METH nitrogen have a black border. The sequence of 6H4 is SEQ ID NO:2 and the sequence of 4G9 is SEQ ID NO:3.

(FIG. 17A) Depicts Coomassie stained reducing SDS-PAGE showing G3 dendrimer alone, mAb4G9 alone, and mAb-G3 mixture after EDC/Sulfo-NHS crosslinking. (FIG. 17B) Depicts Q-sepharose separation of crosslinking reaction. Key: G3, dendrimer; HC, IgG heavy chain; and, LC, IgG light chain.

(FIG. 23A)

Short acting anti-METH scFvCys engineered from long acting IgG followed by the conjugation of scFvCys to dendrimer nanoparticle to create dendribodies. (Four scFvs conjugated to the PEGylated dendrimer are shown for illustration purposes). (FIG. 23B) Separation profile of dendribodies from unreacted scFv7F9Cys. Peak assignments: (B8-C9) dendribodies and (C10-D11) PEGylated and unreacted scFv7F9Cys. DTT treated scFv7F9Cys exists in vitro mainly as mixture of monomer and dimer. (FIG. 23C) SDS-PAGE analysis of the fractions. (FIG. 23D) SDS-PAGE analysis of pooled and concentrated elution fractions B11-C9.

(FIG. 24A) In vitro methamphetamine (METH) saturation data for specific binding of $^3$H-METH to scFv7F9Cys and dendribodies. The $K_D$ of the scFv7F9Cys and dendribodies were 6.2 and 3.2 nM, respectively. (FIG. 24B) In vitro competition binding analysis to determine the affinity of scFv7F9Cys and dendribodies for amphetamine (AMP). The $IC_{50}$ of the scFv7F9Cys and dendribodies were 8 and 4 µM, respectively. Upon conjugation to dendrimer nanoparticles, an increase in scFv7F9Cys affinity for METH and AMP was seen. Data points are the mean±S.E.M. of triplicate determinations. (FIG. 24C) In vitro hemolysis assay: G3 PAMAM dendrimers exhibit concentration dependent hemolysis, whereas PEGylated dendrimers, unconjugated scFv6H4Cys and dendribodies are non-hemolytic. PEG functionalization protects the erythrocytes from hemolysis better than control buffer (PBS).

(FIG. 25A) Schematic representation of the dosing regimen used for the in vivo pharmacokinetic studies. (FIG. 25B) Concentration-time profile of anti-METH scFv7F9Cys and dendribodies after i.v. bolus dosing. The total amount of antibody (µg/ml) in the serum was calculated based on the ratio of dose to radiolabeled protein dose (DPM). Values represent the mean±SEM. Connecting lines in the graph are representative and not the fitted curves used for pharmacokinetic modeling and determination of final pharmacokinetic parameters.

(FIG. 26A) Organ distribution of scFv7F9Cys in male Sprague Dawley rats at three time points: 0.5, 2 and 8 hr post-injection (n=2 per time point) depicted as percent injected dose recovered per gram of organ (% ID/g). (FIG. 26B) Organ distribution of dendribodies in male Sprague Dawley rats at three time points: 0.5, 8 and 24 hr post-injection (n=2 per time point) depicted as percent injected dose recovered per gram of organ (% ID/g). (FIG. 26C) Blood circulation and urine profile of $^3$H-tracer in blood and urine data for scFv7F9Cys and dendribody group agrees well with the estimated pharmacokinetic parameters. Renal clearance appears to be the major route of elimination for both groups.

SUMMARY OF THE INVENTION

Figure 1A:
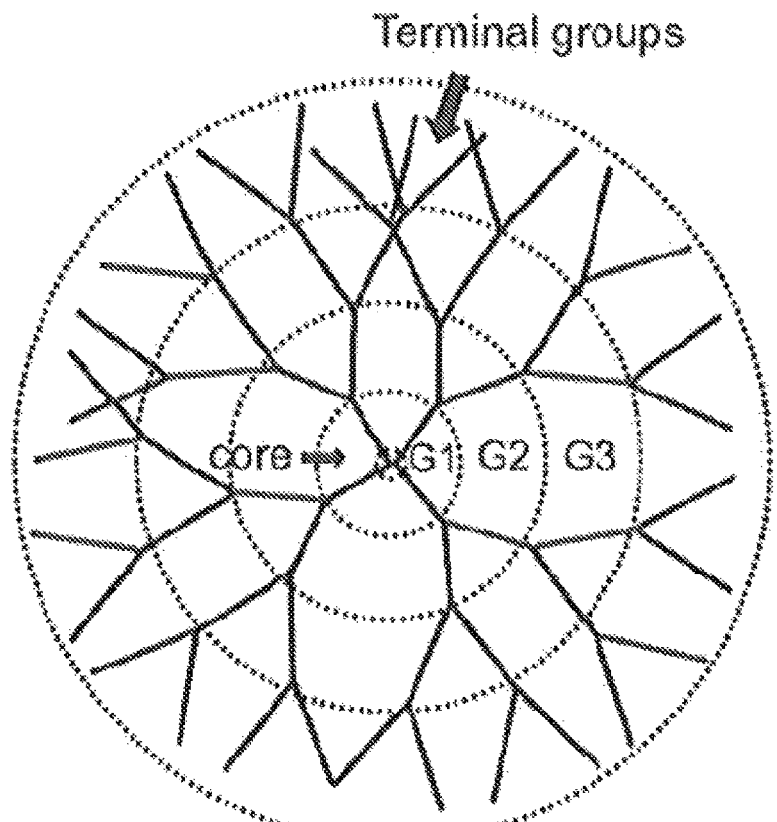
FIG. 1A, FIG. 1B and FIG. 1C depict schematics of components used to create the antibody-nanoparticle conjugated composition of the invention.

The present invention is directed to compositions and methods for treating drug use, addiction, and effects of drug abuse. In particular, the present invention is directed to an antibody composition including antibodies and nanoparticles. Also, the present invention is directed to methods of treating a subject using the antibody compositions of the invention.

One aspect of the invention encompasses a method of antagonizing the effects of amphetamine and amphetamine-like compounds in a subject. The method comprises administering to the subject an antibody composition comprising a single chain antibody that binds an amphetamine compound, a nanoparticle, and, a crosslinker. The antibody composition antagonizes the effects of the amphetamine compound by binding the compound. The antibody composition still displays at least 30% binding activity in the subject at 72 hours after administration, when compared to binding activity of the antibody composition at 1 minute after administration.

A further aspect of the invention provides an antibody composition comprising a single chain antibody, a nanoparticle, and a crosslinker.

Other features and aspects of the invention are described in more detail herein.

DETAILED DESCRIPTION

The present invention provides antibody compositions including antibodies conjugated to nanoparticles having a higher in vivo half-life compared to either the antibody or nanoparticle alone. In one aspect, the present invention provides antibody compositions that have specificity and affinity for amphetamine compounds. These antibody compositions recognize at least one compound of the group consisting of (+)amphetamine, (+)methamphetamine, and (+)3,4-methylenedioxymethamphetamine ((+)MDMA). Because of their specificity and affinity, the antibody compositions may be used to treat drug use, drug addiction, and effects of drug use in a subject.

I. Compositions

In some aspects, the present invention provides antibody compositions. Antibody compositions of the invention comprise an antibody conjugated to a nanoparticle.

(a) Antibodies

In one embodiment, the antibody compositions may recognize at least one compound of the group consisting of (+)methamphetamine, (+)amphetamine, and (+)MDMA. In another embodiment, the antibody compositions may recognize at least two compounds from the group consisting of (+)methamphetamine, (+)amphetamine, and (+)MDMA. In an exemplary embodiment, the antibody compositions may recognize all three compounds of the group consisting of (+)methamphetamine, (+)amphetamine, and (+)MDMA. In another exemplary embodiment, the antibody compositions may recognize all three compounds of the group consisting of (+)methamphetamine, (+)amphetamine, and (+)MDMA, and not substantially recognize over the counter medications. In yet another exemplary embodiment, the antibody compositions may recognize all three compounds of the group consisting of (+) methamphetamine, (+)amphetamine, and (+)MDMA, and not substantially recognize non-(+) methamphetamine like prescription medications. In each of the above embodiments, the antibody compositions do not substantially recognize (−) methamphetamine, (−)amphetamine, and (−)MDMA.

An antibody composition of the invention "recognizes" a compound if the $IC_{50}$ ratio for that antibody is greater than about 20%. The $IC_{50}$ ratio may be calculated in reference to either (+)methamphetamine or (+)amphetamine. Typically, if the antibody is generated with a hapten derived from (+)methamphetamine, then the $IC_{50}$ ratio should be determined in reference to (+)methamphetamine. Similarly, if the antibody is generated with a hapten derived from (+)amphetamine, then the $IC_{50}$ ratio should be determined in reference to (+)amphetamine. For instance, if the hapten was derived from a compound of formula (I),

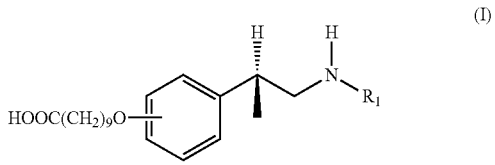

(I)

wherein $R_1$ is hydrogen (i.e. forming (+)amphetamine), then the $IC_{50}$ ratio should be determined in reference to (+)amphetamine. Alternatively, if $R_1$ of formula (I) is a methyl group (i.e. forming (+)methamphetamine), then the $IC_{50}$ ratio should be determined in reference to (+)methamphetamine.

In reference to (+)methamphetamine, the $IC_{50}$ ratio refers to the ratio of the $IC_{50}$ for (+)methamphetamine in the presence of labeled (+)methamphetamine to the $IC_{50}$ for a test ligand in the presence of labeled (+)methamphetamine. The $IC_{50}$ value is the concentration of test ligand required to inhibit 50% of the labeled (+)methamphetamine binding.

In reference to (+)amphetamine, the $IC_{50}$ ratio refers to the ratio of the $IC_{50}$ for (+)amphetamine in the presence of labeled (+)amphetamine to the $IC_{50}$ for a test ligand in the presence of labeled (+)amphetamine. The $IC_{50}$ value is the concentration of test ligand required to inhibit 50% of the labeled (+)amphetamine binding.

Irrespective of whether the $IC_{50}$ ratio is determined in reference to (+)methamphetamine or (+)amphetamine, an antibody of the invention "recognizes" a compound if the $IC_{50}$ ratio is greater than about 20%. In one embodiment, an antibody composition of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)methamphetamine (e.g. an anti-(+) METH antibody composition).

In another embodiment, an antibody composition of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)amphetamine (e.g. an anti-(+)AMP antibody composition).

In yet another embodiment, an antibody composition of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)MDMA (e.g. an anti-(+)MDMA antibody composition).

In still another embodiment, an antibody composition of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)methamphetamine and (+)amphetamine (e.g. an anti-(+) METH/(+)AMP antibody composition).

In a further embodiment, an antibody composition of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)methamphetamine and (+)MDMA (e.g. an anti-(+) METH/(+)MDMA antibody composition).

In a further embodiment, an antibody composition of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)amphetamine and (+)MDMA (e.g. an anti-(+)AMP/(+)MDMA antibody composition).

In an exemplary embodiment, an antibody composition of the invention has an $IC_{50}$ ratio of greater than about 20%, greater than about 23%, greater than about 25%, greater than about 27%, greater than about 30%, greater than about 33%, greater than about 35%, greater than about 37%, greater than about 40%, greater than about 43%, greater than about 45%, greater than about 47%, greater than about 50%, greater than about 53%, greater than about 55%, greater than about 57%, greater than about 60%, greater than about 63%, greater than about 65%, greater than about 67%, greater than about 70%, greater than about 73%, greater than about 75%, greater than about 77%, greater than about 80%, greater than about 83%, greater than about 85%, greater than about 87%, greater than about 90%, greater than about 93%, greater than about 95%, greater than about 97%, or greater than about 100% for (+)methamphetamine, (+)amphetamine, and (+)MDMA (e.g. an anti-(+)METH/(+)AMP/(+)MDMA antibody composition).

An antibody of the invention "substantially does not recognize" a compound if the $IC_{50}$ ratio is less than about 15%. In one embodiment, an antibody composition of the invention has an $IC_{50}$ ratio of less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1% for (−)methamphetamine, (−)amphetamine, and (−)MDMA. In another embodiment, an antibody composition of the invention may have an $IC_{50}$ ratio of less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1% for over the counter medications. In yet another embodiment, an antibody composition of the invention may have an $IC_{50}$ ratio of less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1% for non-(+)methamphetamine like prescription medications.

The antibodies may be murine antibodies, human antibodies, humanized antibodies, chimeric antibodies, recombinant antibodies, or antibody fragments thereof without departing from the scope of the invention. In one embodiment, the invention encompasses murine antibodies or fragments. Non-limiting examples of murine antibodies include mouse and rat antibodies. In another embodiment, the invention encompasses human antibodies or fragments. In yet another embodiment, the invention encompasses humanized antibodies or fragments. In still yet another embodiment, the invention encompasses chimeric antibodies or fragments. In an alternative embodiment, the invention encompasses recombinant antibodies or fragments. Recombinant antibodies include antibodies that have been engineered so as to reduce the antibodies' immunogenicity when used as a medication. In another alternative, the invention encompasses antibody fragments. Non-limiting examples of such fragments include Fab fragments, Fab' fragments, F(ab')$_2$ fragments, single chain antigen binding fragments (scFv), disulfide stabilized Fv (dsFv) fragments, single domain antigen binding fragments, and other antibody fragments that maintain the binding specificity of the whole antibody but that are less immunogenic, more cost-effective to produce, or more pharmaceutically effective than the whole antibody.

Antibodies may have lambda, kappa, or a recombinant light chain. Additionally, antibodies are typically, but not necessarily, IgG antibodies. In certain embodiments, the IgG antibodies may include antibodies from the IgG1, IgG2, IgG3, and IgG4 human antibody classes. In other embodiments, the IgG antibodies may include antibodies from the IgG1, IgG2a, IgG2b, and IgG3 mouse antibody classes.

In some preferred embodiments, an antibody of the invention is mAb6H4. In exemplary embodiments, an antibody fragment of the invention is scFv6H4. mAb6H4 and scFv6H4 may be as described in the Examples, and in Carroll et al., 2009 J Med Chem 52:7301:7309; Laurenzana et al., 2009 Vaccine 27:7011-7020; Peterson et al., 2008 J Pharmacol Exp Ther 325:124-133; and Nanaware-Kharade et al., 2012 Bioconjug Chem 23:1864-1872, the disclosures of which are incorporated herein in their entirety.

In other preferred embodiments, an antibody of the invention is mAb4G9. In exemplary embodiments, an antibody fragment of the invention is scFv4G9. mAb4G9 and scFv4G9 may be as described in the Examples, and in Carroll et al., 2009 J Med Chem 52:7301:7309, Laurenzana et al., 2009 Vaccine 27:7011-7020, and Peterson et al., 2008 J Pharmacol Exp Ther 325:124-133, the disclosures of which are incorporated herein in their entirety.

In yet other preferred embodiments, an antibody of the invention is mAb7F9. In exemplary embodiments, an antibody fragment of the invention is scFv7F9. mAb7F9 and scFv7F9 may be as described in the Examples, and in Stevens et al., 2013 mAbs 6(2):547-555, the disclosure of which is incorporated herein in its entirety.

(b) Methods of Making Monoclonal Antibodies i. Hapten Compounds for Making Monoclonal Antibodies Hapten compounds may be used to elicit antibodies that recognize at least one of the compounds selected from the group consisting of (+)methamphetamine, (+)amphetamine, and (+)MDMA, but not substantially recognize (−)methamphetamine, (−) amphetamine, and (−)MDMA. In certain embodiments, the hapten compound is designed to generate antibodies that recognize at least two compounds from the group consisting of (+)methamphetamine, (+)amphetamine, and (+)MDMA. In an exemplary embodiment, the hapten compound is designed to generate monoclonal antibodies that recognize all three compounds of the group consisting of (+)methamphetamine, (+)amphetamine, and (+)MDMA. Typically, such a hapten compound will comprise either (+)methamphetamine or (+)amphetamine conjugated to a linker (L).

In general, L is comprised of atoms and is of a sufficient length so that L is flexible enough to facilitate an orientation of the (+)methamphetamine or (+) amphetamine sufficient to generate desired antibodies. In this context, "desired" antibodies include antibodies that recognize at least one compound selected from the group consisting of (+)methamphetamine, (+)amphetamine, and (+)MDMA. L is also typically not strongly immunogenic. In other words, L may be designed so that antibodies generated against a compound of the invention recognize the compound without the need for L to be linked to the compound or present in a subject during treatment.

The exact length of L can and will vary. Typically, L is at least 9 angstroms long. In one embodiment, L may be from about 9 angstroms to about 27 or more angstroms long. In another embodiment, L is at least 11 angstroms, at least 12 angstroms, at least 13 angstroms, at least 14 angstroms, at least 15 angstroms, at least 16 angstroms, at least 17 angstroms, at least 18 angstroms, at least 19 angstroms, at least 20 angstroms, at least 21 angstroms, at least 22 angstroms, at least 23 angstroms, at least 24 angstroms, at least 25 angstroms, at least 26 angstroms, or at least 27 angstroms. The length of the linker when expressed in angstroms may be determined by performing a modeling study, using, for instance, the MM94 force field. Stated another way, the length of L may be expressed as the number of contiguous atoms forming the shortest path from one substructure that L connects to the other substructure. In one embodiment, L is at least 6 contiguous atoms in length. In another embodiment, L may be from about 8 to about 100 or more atoms in length. In an additional embodiment, L is 6, 7, 8, 9, 10, 11, 12, 13, 14, 15, 16, 17, 18, 19, 20, 21, 22, 23, 24, 25, 26, 27, 28, 29, or 30 or more contiguous atoms in length.

As will be appreciated by a skilled artisan, the atoms comprising L may vary widely. Typically, the atoms impart the appropriate degree of flexibility, as detailed above. Suitable atoms forming L may be selected from the group comprising hydrocarbyl, substituted hydrocarbyls, and heteroatoms. In some embodiments, L may be comprised of amino acids, such as glycine or proline. For instance, L may be a peptide. In other embodiments, L may be comprised of nucleotides. In further embodiments, L may be linear, branched, or may comprise ring structures.

It is also envisioned that L may be attached to the benzene ring of (+)methamphetamine or (+)amphetamine at a variety of positions without departing from the scope of the invention. For example, in one embodiment, L may be attached at the meta position of the benzene ring. In another embodiment, L may be attached at the ortho position. In yet another embodiment, L may be attached at the para position.

In an exemplary embodiment, the hapten compound may comprise a compound of formula (I):

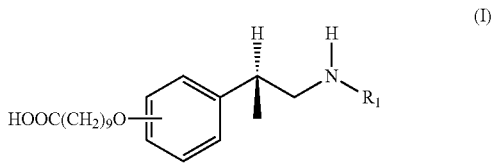

wherein:
$R_1$ is selected from the group consisting of hydrogen and methyl. In some embodiments, $R_1$ is hydrogen (i.e., forming (+) amphetamine). In other embodiments, $R_1$ is a methyl group (i.e., forming (+) methamphetamine). In formula (I), L is represented by the —O(CH$_2$)$_9$COOH group. Therefore, in one embodiment, the —O(CH$_2$)$_9$COOH group may be in the ortho position. In another embodiment, the —O(CH$_2$)$_9$COOH group may be in the meta position. In yet another embodiment, the —O(CH$_2$)$_9$COOH group may be in the para position. In other exemplary embodiments, the hapten compound may comprise a compound listed in Table 3.

ii. Immunizing Agents Comprising Hapten Compounds

To elicit an antibody response, immunizing agents comprising hapten compounds may be used. In certain embodiments, an immunizing agent may comprise a hapten compound and an adjuvant. Generally speaking, an adjuvant may be used to increase the immune response to a hapten compound. For instance, an adjuvant may be used to increase antibody affinity, antibody titer, and the duration of the immune response. Non-limiting examples of adjuvants include alum, TiterMax Gold, Ribi, ASO4, Freund's complete adjuvant, and Freund's incomplete adjuvant. In one embodiment, the adjuvant may be alum. In another embodiment, the adjuvant may be TiterMax Gold. In yet another embodiment, the adjuvant may be Ribi. In still another embodiment, the adjuvant may be ASO4. In still yet another embodiment, the adjuvant may be Freund's complete adjuvant. In an additional embodiment, the adjuvant may be Freund's incomplete adjuvant.

In some embodiments, an immunizing agent may further comprise a pharmaceutically acceptable carrier. Briefly, a pharmaceutically acceptable carrier safely elicits an antibody response in a subject. In this context, safely means that the carrier does not substantially elicit an immune response that cross-reacts with a self-protein, or a regularly ingested protein. Typically, the carrier may be a protein, lipid, carbohydrate, or any combination thereof that is capable of eliciting an immune response. In some embodiments, the carrier is a protein. In a particular embodiment, the carrier may be selected from the group of proteins comprising keyhole limpet hemocyanin (KLH), ovalbumin, bovine serum albumin (BSA), sheep albumin, thyroglobulin, and any modifications, derivatives, or analogues thereof. For instance, in one embodiment, the carrier may be BSA or cationized BSA. In another embodiment, the carrier may be KLH. In yet another embodiment, the carrier may be thyroglobulin.

In another particular embodiment, the carrier may be a bacterial toxin or toxoid. Non-limiting examples of suitable bacterial toxins or toxoids may include tetanus toxoid, diphtheria toxoid, non-toxic mutant diphtheria toxoid CRM$_{197}$, outer membrane protein complex (OMPC) from *Neisseria meningitidis*, the B subunit of heat-labile *Escherichia coli*, recombinant exoprotein A from *Pseudomonas aeruginosa* (rEPA), cholera toxin B-(CTB), pertussis toxin and filamentous hemagglutinin, shiga toxin, and the LTB family of bacterial toxins.

In an alternative embodiment, an immunizing agent comprising a hapten compound may further comprise an excipient. Non-limiting examples of excipients include sterile water, salt solutions such as saline, sodium phosphate, sodium chloride, alcohol, gum arabic, vegetable oils, benzyl alcohols, polyethylene glycol, gelatin, mannitol, carbohydrates, magnesium stearate, viscous paraffin, fatty acid esters, hydroxy methyl cellulose, and buffer. Other suitable excipients may be used by those skilled in that art.

iii. Hybridoma Methods

Antibodies may be prepared using hybridoma methods, such as those described by Kohler and Milstein, Nature, 256:495 (1975). In a hybridoma method, a mouse, hamster, or other appropriate host animal is typically immunized with an immunizing agent, as described above, to elicit lymphocytes that produce or are capable of producing antibodies that will specifically bind to the immunizing agent. Alternatively, the lymphocytes may be immunized in vitro.

The immunizing agent will typically comprise a hapten compound capable of eliciting antibodies that recognize at least one of the compounds selected from the group consisting of (+)methamphetamine, (+)amphetamine, and (+)MDMA, but not substantially recognize (−)methamphetamine, (−)amphetamine, and (−)MDMA, as described above and as detailed in the examples.

Generally, the lymphocytes from the host animal immunized with a hapten compound are collected and fused with an immortalized cell line using a suitable fusing agent, such as polyethylene glycol, to form a hybridoma cell [Goding, Monoclonal Antibodies: Principles and Practice, Academic Press, (1986) pp. 59 103]. Peripheral blood lymphocytes ("PBLs") may be used if cells of human origin are desired, or spleen cells or lymph node cells may be used if non-human mammalian sources are desired. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human antibodies [Kozbor, J. Immunol., 133:3001 (1984); Brodeur et al., Monoclonal Antibody Production Techniques and Applications, Marcel Dekker, Inc., New York, (1987) pp. 51 63].

The culture medium in which the hybridoma cells are cultured can then be assayed for the presence of antibodies that recognize at least one compound selected from the group consisting of (+)methamphetamine, (+)amphetamine, and (+)MDMA, but do not substantially recognize (−)methamphetamine, (−)amphetamine, and (−)MDMA. Preferably, the binding specificity of antibodies produced by the hybridoma cells is determined by immunoprecipitation or by an in vitro binding assay, such as radioimmunoassay (RIA) or enzyme-linked immunoabsorbent assay (ELISA). In an exemplary embodiment, the binding specificity is determined using the RIA method detailed in the Examples.

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The antibodies secreted by the subclones may be isolated or purified from the culture medium or ascites fluid by conventional immunoglobulin purification procedures such as, for example, protein A-Sepharose, protein G-Sepharose, hydroxyapatite chromatography, ion exchange chromatography, gel electrophoresis, dialysis, or affinity chromatography.

iv. Recombinant Antibody Methods

The antibodies may also be made by recombinant DNA methods, such as those described in U.S. Pat. No. 4,816,567. DNA (including cDNA derived from reverse transcription of RNA) encoding the antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of antibodies in the recombinant host cells. The DNA also may be modified, for example, by substituting the coding sequence for human heavy and light chain constant domains in place of the homologous murine sequences [U.S. Pat. No. 4,816,567] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric antibody. Methods of creating recombinant or chimeric antibodies are well known in the art. See, for instance, Harlow and Lane, Antibodies: a Laboratory Manual, Cold Spring Harbor Laboratory (1988).

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Antibodies and antibody fragments may also be produced in plant expression systems. For more details, see Peterson et al., The AAPS Journal 2006; 8(2): E383.

v. Human and Humanized Antibody Methods

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarily determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region, typically that of a human immunoglobulin [Jones et al., Nature, 321:522 525 (1986); Riechmann et al., Nature, 332:323 329 (1988); and Presta, Curr. Op. Struct. Biol., 2:593 596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522 525 (1986); Riechmann et al., Nature, 332:323 327 (1988); Verhoeyen et al., Science, 239:1534 1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86 95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al, Bio/Technology 10: 779-783 (1992); Lonberg et al., Nature 368:856-859 (1994); Morrison, Nature 368:812-13 (1994); Fishwild et al, Nature Biotechnology 14:845-51 (1996); Neuberger, Nature Biotechnology 14:826 (1996); Lonberg and Huszar, Intern. Rev. Immunol. 13:65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

(c) Antibody Conjugated to Nanoparticle

The antibody compositions of the invention include nanoparticles. Suitable nanoparticles include any known in the art that do not reduce the affinity, or recognition, of an associated antibody or antibody fragment for its target. Non limiting examples of nanoparticles that may be suitable for an antibody composition of the invention include liposomes, poloxamers, microemulsions, micelles and other phospholipid-containing systems, lanthanide-doped zirconia, metal nanoparticles such as gold nanoparticles, titanium oxide nanoparticles, iron oxide nanoparticles, quantum dots, carbon nanotubes, amine functionalized iron, ferraheme, silica, silica oxide, silica coated magnetic, titanium, titanium oxide, PGLA, magnetic, magnetite, mesoporous Fe3O4, siliceouscobalt, SPIO, silver, silver oxide, platinum, platinum oxide, and dendrimers, dendron, or hyperbranched polymers such as G1-10 PAMAM dendrimers.

Preferably, the nanoparticle is a dendrimer, dendron, hyperbranched polymer, or a combination thereof. More preferably, the nanoparticle is a dendrimer. Suitable dendrimers include poly(amidoamine) (PAMAM) dendrimers, phosphorous dendrimers, polylysine dendrimers, polypropylenimine dendrimers, or combinations thereof. More preferably, the nanoparticle is poly(amidoamine). More preferably, the nanoparticle is a generation 3, 4, or 5 poly (amidoamine) dendrimer. More preferably, the nanoparticle is a generation 3 poly(amidoamine) dendrimer.

An antibody or antibody fragment may be conjugated to a nanoparticle by any method or means known in the art. In general, an antibody or antibody fragment may be conjugated to a nanoparticle by a crosslinker. Briefly, suitable crosslinkers may react with one or more active groups in a nanoparticle, and an antibody or antibody fragment of the invention may then be conjugated to the crosslinker.

One of ordinary skill in the art would recognize that a suitable crosslinker can and will vary depending on the composition of the nanoparticle and the antibody or antibody fragment. In some aspects, an antibody or antibody fragment may be chemically crosslinked to a nanoparticle using chemical crosslinkers such as glutaraldehyde, bis-carboxylic acid spacers, bis-carboxylic acid-active esters, using a bis-linker amine/acid by carbodiimide coupling protocol, or using a click chemistry protocol, carbodiimide-coupling chemistry, acylation, active ester coupling, or alkylation. In some embodiments, the crosslinking is carbodiimide mediated. In other embodiments, EDC (also EDAC or EDCI, 1-ethyl-3-(3-dimethylaminopropyl) carbodiimide hydrochloride), a highly water soluble carbodiimide, is used in combination with N-hydroxysuccinimide (NHS) or sulfo-NHS.

Crosslinkers may also be homobifunctional or heterobifunctional. In some embodiments, an antibody or antibody fragment is chemically crosslinked to a nanoparticle using a homobifunctional chemical linker. Suitable homobifunctional linkers may include disuccinimidyl suberate, disuccinimidyl glutarate, and disuccinimidyl tartrate. In preferred embodiments, an antibody or antibody fragment is chemically crosslinked to a nanoparticle using a heterobifunctional chemical linker. Suitable heterobifunctional chemical linkers may include any heterobifunctional crosslinker comprising a sulfhydryl reactive group at one terminus and an amine or carboxyl reactive group at the other terminus. For instance, a heterobifunctional crosslinker may be poly(ethylene)glycol of any length, succinimidyl acetylthioacetate (SATA), succinimidyl trans-4-(maleimidylmethyl)cyclohexane-1-carboxylate (SMCC), and succinimidyl 3-(2-pyridyldithio)propionate (SPDP). In one aspect, the crosslinker is a heterobifunctional $PEG_{24}$ crosslinker.

The number of antibodies or antibody fragments that may be conjugated to a nanoparticle to generate a composition of the invention can and will vary depending on the nanoparticle, the antibody or antibody fragment, the intended use of the composition, and may be determined experimentally. For instance, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 or more antibodies or antibody fragments may be conjugated to a nanoparticle. In some embodiments, about 1, 2, 3, 4, 5, 6, 7, 8, 9, or about 10 antibodies are conjugated to a nanoparticle. In other embodiments, about 10, 11, 12, 13, 14, 15, 16, 17, 18, 19, or about 20 antibodies are conjugated to a nanoparticle. In yet other embodiments, about 20, 21, 22, 23, 24, 25, 26, 27, 28, 29, or about 30 antibodies are conjugated to a nanoparticle. In additional embodiments, about 30, 31, 32, 33, 34, 35, 36, 37, 38, 39, or about 40 antibodies are conjugated to a nanoparticle. In other embodiments, about 40, 41, 42, 43, 44, 45, 46, 47, 48, 49, or about 50 antibodies are conjugated to a nanoparticle. In yet other embodiments, about 50, 55, 60, 65, 70, 75, 80, 85, 90, 95, or about 100 antibodies or more are conjugated to a nanoparticle. In some preferred embodiments, about 3, 4, 5, 6, or about 7 antibodies are conjugated to a nanoparticle. In other preferred embodiments, about 18, 19, 20, 21, or about 22 antibodies are conjugated to a nanoparticle. In a preferred embodiment, about 14, 15, 16, 17, 18, or about 19 antibodies are conjugated to a nanoparticle.

In some embodiments, all conjugation sites available in a nanoparticle are conjugated with antibodies or antibody fragments. For instance, when a nanoparticle is a G3 PAMAM dendrimer, 32 amine terminal groups may be available for conjugation of an antibody or antibody fragment. As such, a G3 PAMAM dendrimer may be conjugated with 32 antibodies or antibody fragments. In other embodiments, a fraction of conjugation sites available in a nanoparticle are conjugated with antibodies or antibody fragments. As such, when a nanoparticle is a G3 PAMAM dendrimer, about 10, 20, 30, 40, 50, 60, 70, 80, 90 or about 99%, preferably about 50, 55, 60, 65, 70, or about 75%, even more preferably about 55, 56, 57, 58, 59, 60, 61, 62, 63, 64, 65, 66, 67, 68, 69, or about 70% of 32 amine terminal groups of a G3 PAMAM dendrimer may be conjugated to an antibody or antibody fragment. In some embodiments, about 59, 60, 61, 62, 63, 64, 65, 66, or about 67% of 32 amine terminal groups of a G3 PAMAM dendrimer are conjugated to an antibody or antibody fragment.

According to the invention, conjugation of an antibody or antibody fragment to a nanoparticle alters the in vivo half life of the antibody. An antibody or antibody fragment of the invention may have a higher or lower in vivo half-life when conjugated to a nanoparticle compared to an in vivo half-life of the antibody or antibody fragment alone. The term "half-life" is used in the art to describe the time required for a quantity to fall to half its value as measured at the beginning of a time period. A skilled artisan will recognize that the desired half-life of an antibody composition depends upon the intended use of the antibody composition. For instance, if the antibody composition is used to treat the effects of drug abuse, a longer half-life may be desired. However, if the antibody composition is used to rapidly clear the body of a subject of small molecule toxins, a shorter half-life may be desired. In some embodiments, a composition comprising an antibody conjugated to a nanoparticle has an in vivo half-life$_{(t1/2)}$ that is less, or shorter, than a composition comprising an unconjugated antibody. In preferred embodiments, a composition comprising an antibody conjugated to a nanoparticle has an in vivo half-life$_{(t1/2)}$ that is greater, or longer, than a composition comprising an unconjugated antibody.

In vivo half-life of an antibody composition may refer to the time required for the binding activity of an antibody composition to fall to half its value as measured at the beginning of a time period in a sample taken from a subject administered the antibody composition. As such, an antibody or antibody fragment of the invention may display a longer in vivo binding activity half-life when conjugated to a nanoparticle, than in vivo binding activity half-life of the same antibody or antibody fragment when not conjugated to a nanoparticle. Alternatively, in vivo half-life of an antibody composition may refer to the time required for the concentration of an antibody composition to fall to half its value as measured at the beginning of a time period in a sample taken from a subject administered the antibody composition. As such, an antibody or antibody fragment of the invention displays higher in vivo antibody concentration half-life when conjugated to a nanoparticle, than the in vivo antibody concentration half-life of the same antibody or antibody fragment when not conjugated to a nanoparticle.

An antibody composition of the invention may still display about 10, 20, 30, 40, 50, 60, 70, 80, 90, or about 100% binding activity in a subject at about 2, 3, 4, 5, 6, 7, 8, 9, 10, 11, 12, 24, 36, 48, 60, 72, 84, 96, or about 108 hours after administration, when compared to binding activity of the antibody composition at 1 minute after administration.

In some embodiments, an antibody composition still displays about 80, 81, 82, 83, 84, 85, 86, 87, 88, 89, 90, 91, 92, 93, 94, 95, 96, 97, 98, 99, or about 100% binding activity in a subject at about 5 hours after administration, when compared to binding activity of the antibody composition at 1 minute after administration. In other embodiments, an antibody composition still displays about 80, 81, 82, 83, 84, or about 85% binding activity in a subject at about 5 hours after administration, when compared to binding activity of the antibody composition at 1 minute after administration. In yet other embodiments, an antibody composition still displays about 85, 86, 87, 88, 89, or about 90% binding activity in a subject at about 5 hours after administration, when compared to binding activity of the antibody composition at 1 minute after administration. In preferred embodiments, an antibody composition still displays about 90, 91, 92, 93, 94, or about 95% binding activity in a subject at about 5 hours after administration, when compared to binding activity of the antibody composition at 1 minute after administration. In other preferred embodiments, an antibody composition still displays about 95, 96, 97, 98, 99, or about 100% binding activity in a subject at about 5 hours after administration, when compared to binding activity of the antibody composition at 1 minute after administration. In exemplary embodiments, an antibody composition still displays about 94, 95, 96, 97, 98, or about 99% binding activity in a subject at about 5 hours after administration, when compared to binding activity of the antibody composition at 1 minute after administration.

In some embodiments, an antibody composition still displays about 80, 81, 82, 83, 84, 85, 86, 87, 88, 89, 90, 91, 92, 93, 94, 95, 96, 97, 98, 99, or about 100% binding activity in a subject at about 10 hours after administration, when compared to binding activity of the antibody composition at 1 minute after administration. In other embodiments, an antibody composition still displays about 80, 81, 82, 83, 84, or about 85% binding activity in a subject at about 10 hours after administration, when compared to binding activity of the antibody composition at 1 minute after administration. In yet other embodiments, an antibody composition still displays about 85, 86, 87, 88, 89, or about 90% binding activity in a subject at about 10 hours after administration, when compared to binding activity of the antibody composition at 1 minute after administration. In preferred embodiments, an antibody composition still displays about 90, 91, 92, 93, 94, or about 95% binding activity in a subject at about 10 hours after administration, when compared to binding activity of the antibody composition at 1 minute after administration. In other preferred embodiments, an antibody composition still displays about 95, 96, 97, 98, 99, or about 100% binding activity in a subject at about 10 hours after administration, when compared to binding activity of the antibody composition at 1 minute after administration. In exemplary embodiments, an antibody composition still displays about 93, 94, 95, 96, 97, or about 98% binding activity in a subject at about 10 hours after administration, when compared to binding activity of the antibody composition at 1 minute after administration.

In some embodiments, an antibody composition still displays about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or about 80% binding activity in a subject at about 48 hours after administration, when compared to binding activity of the antibody composition at 1 minute after administration. In other embodiments, an antibody composition still displays about 50, 51, 52, 53, 54, or about 55% binding activity in a subject at about 48 hours after administration, when compared to binding activity of the antibody composition at 1 minute after administration. In yet other embodiments, an antibody composition still displays about 55, 56, 57, 58, 59, or about 60% binding activity in a subject at about 48 hours after administration, when compared to binding activity of the antibody composition at 1 minute after administration. In preferred embodiments, an antibody composition still displays about 60, 61, 62, 63, 64, or about 65% binding activity in a subject at about 48 hours after administration, when compared to binding activity of the antibody composition at 1 minute after administration. In other preferred embodiments, an antibody composition still displays about 65, 66, 67, 68, 69, or about 70% binding activity in a subject at about 48 hours after administration, when compared to binding activity of the antibody composition at 1 minute after administration. In additional preferred embodiments, an antibody composition still displays about 65, 66, 67, 68, 69, or about 70% binding activity in a subject at about 48 hours after administration, when compared to binding activity of the antibody composition at 1 minute after administration. In preferred embodiments, an antibody composition still displays about 70, 71, 72, 73, 74, or about 75% binding activity in a subject at about 48 hours after administration, when compared to binding activity of the antibody composition at 1 minute after administration. In preferred embodiments, an antibody composition still displays about 75, 76, 77, 78, 79, or about 80% binding activity in a subject at about 48 hours after administration, when compared to binding activity of the antibody composition at 1 minute after administration.

In some embodiments, an antibody composition still displays about 10, 20, or about 30% binding activity in a subject at about 72 hours after administration, when compared to binding activity of the antibody composition at 1 minute after administration. In other embodiments, an antibody composition still displays about 30, 40, or about 50% binding activity in a subject at about 72 hours after administration, when compared to binding activity of the antibody composition at 1 minute after administration. In yet other embodiments, an antibody composition still displays about 50, 60, or about 70% binding activity in a subject at about 72 hours after administration, when compared to binding activity of the antibody composition at 1 minute after administration. In preferred embodiments, an antibody composition still displays about 40% binding activity in a subject at about 72 hours after administration, when compared to binding activity of the antibody composition at 1 minute after administration. In other preferred embodiments, an antibody composition still displays about 50% binding activity in a subject at about 72 hours after administration, when compared to binding activity of the antibody composition at 1 minute after administration. In exemplary embodiments, an antibody composition still displays about 30% binding activity in a subject at about 72 hours after administration, when compared to binding activity of the antibody composition at 1 minute after administration.

II. Methods of Using the Antibody Compositions

A further aspect of the invention comprises a method of using an antibody composition of the invention. Methods of using an antibody composition of the invention encompass both therapeutic and non-therapeutic uses for the antibody compositions of the invention.

(a) Non-Therapeutic Uses

In certain embodiments, the antibody compositions may be used in non-therapeutic assays, such as immunostaining, immunoprecipitation, immunoblotting, immunoaffinity purification, immunochromatographic assays, lateral-flow assays and ELISAs. In one embodiment, the antibody compositions may be used for immunostaining. In another embodiment, the antibody compositions may be used for immunoprecipitation. In yet another embodiment, the antibody compositions may be used for immunoblotting. In still another embodiment, the antibody compositions may be used for immunoaffinity purification. In still yet another embodiment, the antibody compositions may be used for ELISAs. In an alternative embodiment, the antibody compositions may be used for immunochromatographic assays. In another alternative embodiment, the antibody compositions may be used for lateral-flow assays. Protocols for each of the above non-therapeutic uses are well known in the art, and may be found, for instance, in Harlow and Lane, *Antibodies*, Cold Spring Harbor, 1988, Chapters 9-14, U.S. Pat. Nos. 5,160,701, 5,141,850, 5,451,504, 5,415,994, and U.S. Pat. No. 5,559,041, hereby incorporated by reference.

Additionally, one or more antibody compositions of the invention may be used for detecting (+)methamphetamine, (+)amphetamine, and (+)MDMA in a sample using a non-therapeutic assay described above. For example, one embodiment of the invention is an assay for detecting the presence of at least one compound in a sample selected from the group of compounds consisting of (+)methamphetamine, (+)amphetamine, and (+)3,4-methylenedioxymethamphetamine. The assay comprises contacting the sample with an antibody composition of the invention and detecting the association of the antibody composition in the sample with at least one compound selected from the group consisting of (+)methamphetamine, (+)amphetamine, and (+)3,4-methylenedioxymethamphetamine. In some embodiments, the assay may further comprise quantifying the amount of a compound in the sample selected from the group of compounds consisting of (+)methamphetamine, (+)amphetamine, and (+)3,4-methylenedioxymethamphetamine.

An antibody composition may be used to detect and/or quantify at least one compound from the group consisting of (+)methamphetamine, (+)amphetamine, and (+)MDMA in a sample. In another embodiment, an antibody composition may be used to detect and/or quantify at least two compounds from the group consisting of (+)methamphetamine, (+)amphetamine, and (+)MDMA in a sample. In yet another embodiment an antibody composition may be used to detect and/or quantify each compound of the group consisting of (+)methamphetamine, (+)amphetamine, and (+)MDMA in a sample. In an alternative embodiment, more than one antibody composition may be used to detect and/or quantify each compound of the group consisting of (+)methamphetamine, (+)amphetamine, and (+)MDMA in a sample. Methods and devices for using antibodies to detect and/or quantify substances in samples are well known in the art. For instance, see U.S. Pat. No. 5,328,828.

As used herein, "sample" may refer to a biological sample from a subject or a sample of a chemical substance. Non-limiting examples of biological samples from a subject may include fluid samples or tissue samples. Fluid samples may include blood (including serum or plasma), urine, saliva, or other biological fluids that could comprise (+)methamphetamine, (+)amphetamine, or (+)MDMA. Tissue samples may include hair or skin samples, or other biological tissues that could comprise (+)methamphetamine, (+)amphetamine, or (+)MDMA. Methods of collecting biological samples are well known in the art. Non-limiting examples of chemical substances may include powders, pills, and liquids. For instance, a monoclonal antibody of the invention may be used to detect (+)methamphetamine, (+)amphetamine, or (+)MDMA in a powder of unknown composition.

(b) Therapeutic Uses

Additionally, the antibody compositions may be used for therapeutic purposes. As such, a method of the invention comprises administering to a subject an antibody composition of the invention. An antibody composition antagonizes the effects of amphetamine and amphetamine-like drug compounds in a subject by binding the compounds in the subject. A composition of the invention may be as described in Section I. Methods of the invention are described herein below.

i. Subject

A method of the invention comprises treating a subject by administering to the subject an antibody composition that antagonizes the effects of amphetamine compounds. As used herein, "subject" may include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value. Suitable subjects may also include: mice, rats, dogs, cats, ungulates such as cattle, swine, sheep, horses, and goats, lagomorphs such as rabbits and hares, other rodents, and primates such as monkeys, chimps, and apes. In some preferred embodiments, a subject is a human. In other preferred embodiments, a subject is a rat. In yet other preferred embodiments, a subject is a mouse.

ii. Treating a Subject

A method of the invention comprises treating a subject using amphetamine compounds, or at risk for using amphetamine and amphetamine-like drugs. For instance, a method of the invention may be used to treat a subject addicted to use of amphetamine or amphetamine-like compounds, or at risk for developing a drug addiction to amphetamine and amphetamine-like drugs. Alternatively, a method of the invention may be used to treat a subject with an overdose of amphetamine or amphetamine-like compounds, or at risk for an overdose of amphetamine and amphetamine-like drugs. In some embodiments, a method of the invention is used to treat a subject addicted to use of amphetamine or amphetamine-like compounds. In other embodiments, a method of the invention is used to treat a subject at risk for developing a drug addiction to amphetamine and amphetamine-like drugs. In yet other embodiments, a method of the invention is used to treat a subject with an overdose of amphetamine or amphetamine-like compounds. In additional embodiments, a method of the invention is used to treat a subject at risk for an overdose of amphetamine and amphetamine-like drugs.

Treating a subject using a method of the invention may extend the survival of the subject. Alternatively, treating a subject using a method of the invention may reduce or eliminate the addiction to use of amphetamine or amphetamine-like compounds. For instance, treating a subject may decrease drug-seeking behavior in the subject. Alternatively, treating a subject may decrease self-dosing behavior in the subject. In one embodiment, a subject is treated by decreasing drug-seeking behavior in the subject. In another embodiment, a subject is treated by decreasing self-dosing behavior in the subject.

A method of the invention may antagonize the effects of amphetamine or amphetamine-like compounds in a subject. In some embodiments, the method may comprise administering an antibody composition to a subject, wherein the antibody composition antagonizes the effects of one amphetamine or amphetamine-like compound in the subject. In other embodiments, the method may comprise administering an antibody composition to a subject, wherein the antibody composition antagonizes the effects of two or more amphetamine or amphetamine-like compounds in the subject. In yet other embodiments, the method may comprise administering an antibody composition to a subject, wherein the antibody composition antagonizes the effects of three or more amphetamine or amphetamine-like compounds in the subject.

A subject may be treated by antagonizing the effects of amphetamine and amphetamine-like compounds in the subject. The effects of amphetamine and amphetamine-like compounds may be antagonized by binding amphetamine and amphetamine-like drug compounds in a subject. Binding may antagonize the effects of amphetamine and amphetamine-like drug compounds by decreasing the concentration of the drug compounds in a subject. For instance, administering an antibody composition of the invention may decrease the concentration of drug compounds by binding amphetamine and amphetamine-like drug compounds and targeting the drug compounds for removal from the body by detoxification or excretion. Alternatively, administering an antibody composition of the invention may decrease the effective concentration of amphetamine and amphetamine-like drug compounds by binding the drug compounds and sequestering the compounds in a manner that they are not available to function at the site of action of the compounds, therefore reducing the effective concentration of amphetamine and amphetamine-like compounds in the subject.

In some embodiments, administering an antibody composition of the invention decreases the concentration of amphetamine and amphetamine-like drug compounds by binding the drug compounds, and targeting the drug compounds for removal from the body. In preferred embodiments, administering an antibody composition of the invention decreases the concentration of amphetamine and amphetamine-like drug compounds by binding amphetamine and amphetamine-like drug compounds and decreasing the effective concentration of amphetamine and amphetamine-like drug compounds in the subject. In some embodiments, a composition of the invention decreases the effective concentration of amphetamine and amphetamine-like drug compounds by about 10, 20, 30, 40, 50, 60, 70, 80, 90, or about 100%, preferably by about 30, 40, 50, 60, 70, 80, 90, or about 100%, more preferably by about 60, 70, 80, 90, or about 100%, even more preferably by about 70, 80, 90, or about 100%.

When a composition of the invention decreases the effective concentration of amphetamine and amphetamine-like drug compounds in a subject, the effective concentration of drug compounds may be decreased by decreasing the concentration of drug compounds at the sites of action of the drugs. Sites of action of amphetamine and amphetamine-like drug compounds are known in the art and include all parts of the nervous system, including the central nervous system and the peripheral nervous system. As such, in some embodiments, a method of the invention comprises decreasing the effective concentration of amphetamine and amphetamine-like drug compounds in the nervous system of a subject. In some embodiments, a composition of the invention decreases the effective concentration of amphetamine and amphetamine-like drug compounds in the nervous system of a subject by about 10, 20, 30, 40, 50, 60, 70, 80, 90, or about 100%, preferably by about 30, 40, 50, 60, 70, 80, 90, or about 100%, more preferably by about 60, 70, 80, 90, or about 100%, even more preferably by about 70, 80, 90, or about 100%.

When a composition of the invention decreases the effective concentration of amphetamine and amphetamine-like drug compounds in a subject, the effective concentration of drug compounds may be decreased at the sites of action of the drugs, but the concentrations of sequestered drug compounds may be increased away from the sites of action of the amphetamine and amphetamine-like drug compounds. For instance, a composition of the invention may decrease the effective concentration of amphetamine and amphetamine-like drug compounds in the nervous system of a subject by increasing the concentration of sequestered drugs bound by an antibody of a composition of the invention in the serum. Put differently, administering a composition of the invention to a subject may decrease the effective concentration of amphetamine and amphetamine-like drug compounds in the subject by causing a redistribution of amphetamine and amphetamine-like drug compounds from the nervous system, and into the serum of the subject. As such, administering a composition of the invention to a subject may increase the concentration of amphetamine and amphetamine-like drug compounds in the serum of the subject, wherein the increased concentration of drug compounds in the serum is increased concentrations of drug compounds bound by an antibody of the invention. In some embodiments, administering a composition of the invention to a subject increases the concentration of amphetamine and amphetamine-like drug compounds in the serum of the subject by about 5, 10, 15, 20, 25, 30, 35, 40, 45, 50, 55, 60, 65, 70, 75, 80, 85 fold or more, preferably 15, 20, 25, 30, 35, 40, 45, 50, 55, 60, 65, 70, 75, 80, 85 fold, more preferably 25, 30, 35, 40, 45, 50, 55, 60, 65, 70, 75, 80 fold, even more preferably 40, 45, 50, 55, 60, 65, 70, 75 fold, when compared to the concentration of drug compounds in the serum of the subject before administration of an antibody composition of the invention.

Methods of determining the concentrations of amphetamine and amphetamine-like drug compounds are known in the art, and may be as described in the Examples.

iii. Administration

Generally, a method of the invention comprises administering to a subject an antibody composition comprising a composition of the invention. For instance, 1, 2, 3, 4, 5, 6, 7, 8, 9, 10 or more different antibody compositions may be administered. In some embodiments, 1, 2, 3, 4, or 5 different antibody compositions are administered. In other embodiments, 5, 6, 7, 8, 9, 10 or more different antibody compositions are administered.

An antibody composition of the invention may be administered to a subject by several different means. Methods of administration include any method known in the art or yet to be discovered. Exemplary administration methods include intravenous, intraocular, intratracheal, intratumoral, oral, rectal, topical, intramuscular, intraarterial, intrahepatic, intrathoracic, intrathecal, intracranial, intraperitoneal, intrapancreatic, intrapulmonary, or subcutaneously. One skilled in the art will appreciate that the route of administration and method of administration depend upon the intended use of the compositions, the location of the target area, and the condition being treated, in addition to other factors known in the art such as subject health, age, and physiological status.

In a preferred embodiment, an antibody composition may be administered parenterally. The term "parenteral" as used herein describes administration into the body via a route other than the mouth, especially via infusion, injection, or implantation, and includes intradermal, subcutaneous, transdermal implant, intracavernous, intravitreal, intra-articular or intrasynovial injection, transscleral, intracerebral, intrathecal, epidural, intravenous, intracardiac, intramuscular, intraosseous, intraperitoneal, intravenous, intrasternal injection, or nanocell injection. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

For instance, compositions may generally be administered in dosage unit formulations containing conventional nontoxic pharmaceutically acceptable carriers, adjuvants, and vehicles as desired. As such, the antibody compositions of the present invention may be formulated into pharmaceutical compositions and administered by a number of different means that may deliver a therapeutically effective dose. Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

For therapeutic purposes, formulations for parenteral administration may be in the form of aqueous or non-aqueous isotonic sterile injection solutions or suspensions. These solutions and suspensions may be prepared from sterile powders or granules having one or more of the carriers or diluents mentioned for use in formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

In some embodiments, an antibody composition of the invention is administered into central nervous system fluid. In preferred embodiments, an antibody composition of the invention is administered into the circulatory system. Methods of administering an antibody composition of the invention to the circulatory system are known in the art. For instance, an antibody composition of the invention may be administered in a bolus directly into the circulatory system. Alternatively, an antibody composition of the invention may be administered by continuous infusion into the circulatory system.

In a preferred embodiment, an antibody composition of the invention is administered in a bolus directly into the circulatory system. In another preferred embodiment, an antibody composition is administered by continuous infusion into the circulatory system. Non-limiting examples of methods that may be used to deliver an antibody composition into the circulatory system by continuous infusion may include pumps, wafers, gels, foams and fibrin clots.

The amount of compound of the invention that may be combined with the carrier materials to produce a single dosage of the composition can and will vary depending upon the patient and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Gilman's The Pharmacological Basis of Therapeutics, Tenth Edition (2001), Appendix II, pp. 475-493.

Generally speaking, a dosage of an antibody composition may be from about 1 ng/kg subject body weight per month to about 1 g/kg subject body weight per month. In one embodiment, a dosage of an antibody composition may be from about 1 mg/kg subject body weight per month to about 125 mg/kg subject body weight per month. In another embodiment, a dosage of an antibody composition may be from about 10 mg/kg subject body weight per month to about 150 mg/kg subject body weight per month. In yet another embodiment, a dosage of an antibody composition may be from about 25 mg/kg subject body weight per month to about 100 mg/kg subject body weight per month. In a preferred embodiment, a dosage of an antibody composition may be from about 25 mg/kg subject body weight per month to about 40 mg/kg subject body weight per month.

An antibody composition may be administered to the subject once or multiple times. In some preferred embodiments, an antibody composition is administered once. For instance, an antibody composition may be administered once if the antibody composition is used to clear the body of a subject of a single use of an amphetamine or amphetamine-like compound. In other preferred embodiments, an antibody composition is administered multiple times. An antibody composition may be administered multiple times if the antibody composition is used to clear the body of a subject of continued use of an amphetamine or amphetamine-like compound. When administered multiple times, an antibody composition may be administered at regular intervals or at intervals that may vary during the treatment of a subject. In some embodiments, an antibody composition is administered multiple times at intervals that may vary during the treatment of a subject. In other embodiments, an antibody composition is administered multiple times at regular intervals.

One skilled in the art will appreciate that the frequency and intervals of administration depend upon the antibody composition, the subject, in addition to other factors known in the art such as subject health, age, and physiological status, and may be determined experimentally. As such, an antibody composition may be administered about once a day, once a week, once every two weeks, once every three weeks, once a month, once every two months, about once every three months, or longer. In some embodiments, an antibody composition may be administered about once every 1, 2, 3, 4, 5, 6, or 7 days. In other embodiments, an antibody composition may be administered about once a week. In yet other embodiments, an antibody composition may be administered about once every two weeks. In other embodiments, an antibody composition may be administered about once every three weeks. In additional embodiments, an antibody composition may be administered about once a month. In additional embodiments, an antibody composition may be administered about once every two months. In additional embodiments, an antibody composition may be administered about once every three months, or longer.

One of skill in the art will also recognize that the duration of multiple administrations can and will vary, and will depend in part on the subject, the frequency of drug use, and the duration of drug use by the subject. For instance, a composition of the invention may be administered multiple times until a subject is not using an amphetamine or amphetamine-like compound. Alternatively, a composition of the invention may be administered multiple times even after a subject is not using an amphetamine or amphetamine-like compound, if the subject is suspected of being at risk for using amphetamine and amphetamine-like drugs.

Compositions of the invention are typically administered to a subject in an amount sufficient to provide a benefit to the subject. This amount is defined as a "therapeutically effective amount." A therapeutically effective amount may be determined by the efficacy or potency of the particular composition, the duration or frequency of administration, the method of administration, and the size and condition of the subject, including that subject's particular treatment response, the concentration of amphetamine and amphetamine-like compounds in the subject, the frequency of use of amphetamine and amphetamine-like compounds by the subject. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining the therapeutically effective amounts, one skilled in the art may also consider the existence, nature, and extent of any adverse effects that accompany the administration of a particular compound in a particular subject.

When an antibody composition is administered parenterally, an antibody composition may be administered to the subject in an amount sufficient to bind the amphetamine or amphetamine-like compounds present in the subject. For instance, an amount of an antibody composition of the invention comprising a molar concentration of an antibody of the invention equivalent to the molar concentration of amphetamine or amphetamine-like compound may be administered. Alternatively, an amount of an antibody composition of the invention comprising a molar concentration of an antibody of the invention in excess of the molar concentration of amphetamine or amphetamine-like compound may be administered. In some embodiments, an amount of an antibody composition of the invention that may be administered may comprise about 10, 15, 20, 25, 30, 35, 40, 45, 50, 55, 60, 65, 70, 75, 80, 85, 90, 95, or about 100 mg/kg or more of an antibody or antibody fragment of the invention, more preferably about 20, 25, 30, 35, 40, 45, 50, 55, 60, 65, 70, 75, 80, or about 85 mg/kg, even more preferably about 25, 30, 35, 40, 45, 50, or about 55 mg/kg, and more preferably about 30, 35, 40, or about 45 mg/kg of an antibody or antibody fragment of the invention. In other embodiments, an amount of an antibody composition of the invention that may be administered may comprise about 100, 110, 120, 130, 140, 150, 160, 170, 180, 190, 200, 210, 220, 230, 240, or about 250 mg/kg or more of an antibody or antibody fragment of the invention, more preferably about 120, 130, 140, 150, 160, 170, 180, 190, 200, 210, 220, 230, or about 240 mg/kg, even more preferably about 140, 150, 160, 170, 180, 190, 210 or about 220 mg/kg, and more preferably about 160, 170, 180, 190, or about 200 mg/kg of an antibody or antibody fragment of the invention.

An antibody composition may be administered in combination with at least one additional therapeutic agent. Additional therapeutic agents may include those used in treating drug abuse. Non limiting examples of agents capable of treating drug abuse include behavioral therapies aimed at ending drug abuse, such as cognitive behavioral and contingency management interventions.

An amphetamine or amphetamine-like compound may be (+)methamphetamine, (+)amphetamine, or (+)MDMA, or any compound derived from (+)methamphetamine, (+)amphetamine, or (+)MDMA. In some embodiments, an amphetamine or amphetamine-like compound is (+)methamphetamine, (+)amphetamine, (+)MDMA, or combinations thereof. As such, a method of the invention may antagonize the effects of (+)methamphetamine, (+)amphetamine, (+)MDMA or combinations thereof. In some embodiments, administering an antibody composition to a subject antagonizes the effects of (+)methamphetamine in the subject. In other embodiments, administering an antibody composition to a subject antagonizes the effects of (+)amphetamine in the subject. In yet other embodiments, administering an antibody composition to a subject antagonizes the effects of (+)MDMA in the subject. In other embodiments, administering an antibody composition to a subject antagonizes the effects of combinations of (+)methamphetamine, (+)amphetamine, and (+)MDMA described in Table A.

TABLE A (+)methamphetamine and (+)amphetamine
(+)amphetamine and (+)MDMA
(+)methamphetamine and (+)MDMA
(+)methamphetamine, (+)amphetamine, and (+)MDMA Alternatively, the method of treating drug use may comprise administering more than one antibody composition to a subject to decrease the concentration of (+)methamphetamine, (+)amphetamine, or (+)MDMA in the brain of the subject. If more than one antibody composition is administered to a subject, the antibody compositions may be administered simultaneously or sequentially. In one embodiment, each antibody composition administered to a subject has a different pharmacokinetic profile. For instance, an antibody composition that has a short half-life may be administered together with an antibody composition that has a longer half-life. In another embodiment, each antibody composition administered to a subject has a different affinity for a particular target compound. For instance, an antibody composition that recognizes (+)methamphetamine may be administered together with an antibody composition that recognizes (+)amphetamine. Alternatively, an antibody composition that recognizes at least one compound selected from the group comprising (+)methamphetamine, (+)amphetamine, and (+)MDMA may be administered with an antibody composition that recognizes another drug of abuse, such as cocaine, phencyclidine, opioids, or nicotine.

III. Kits

A further aspect of the invention encompasses kits. The kits typically comprise an antibody composition of the invention described above. The kits may further comprise instructions for detecting and/or quantifying the presence of at least one compound in a sample selected from the group of compounds consisting of (+)methamphetamine, (+)amphetamine, and (+)3,4-methylenedioxymethamphetamine using the methods described above and in the Examples. The kits may also comprise means for collecting a sample. In some embodiments, the sample may be biological. In other embodiments, the sample may be chemical. For instance, in certain embodiments the kits may be used for detecting and/or quantifying the presence of at least one compound in a hair or blood sample selected from the group of compounds consisting of (+)methamphetamine, (+)amphetamine, and (+)3,4-methylenedioxymethamphetamine.

Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein "(d)" stands for dextrorotatory and "(l)" stands for levorotatory, and refers to the direction in which an enantiomer rotates the plane of polarized light. Herein, (d) is used interchangeably with (+), and (l) is used interchangeably with (−).

The terms "amphetamine compound", "amphetamine or amphetamine-like drug compound", "amphetamine or amphetamine-like compound", or "drug compound" may refer to (+)methamphetamine, (+)amphetamine, or (+)MDMA, or any compound derived from (+)methamphetamine, (+)amphetamine, or (+)MDMA.

The phrase "decreasing the concentration of (+)methamphetamine, (+)amphetamine, or (+)MDMA in the brain" may refer to either decreasing the amount of (+)methamphetamine, (+)amphetamine, or (+)MDMA in the brain, or changing the rate of entry of (+)methamphetamine, (+)amphetamine, or (+)MDMA into the brain.

The term "hapten" refers to a partial or incomplete antigen. Haptens are protein-free substances that generally are not capable of stimulating antibody formation, but may react with antibodies. Amphetamine, methamphetamine, and their derivatives are haptens.

The term "subject" as used herein refers to a mammal. Suitable mammals may include mice, rats, dogs, non-human primates, and humans.

As various changes could be made in the above compounds, products and methods without departing from the scope of the invention, it is intended that all matter contained in the above description and in the examples given below, shall be interpreted as illustrative and not in a limiting sense.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials

Chemicals and drugs. Enzymes and *Escherichia coli* strains were purchased from Invitrogen (Carlsbad, Calif.). [3H]-N-Methyl-1-phenylpropane-2-amine (METH) (39 Ci/mmol) labeled at two metabolically stable sites on the aromatic ring structure was obtained from the National Institute on Drug Abuse (Bethesda, Md.) after synthesis at the Research Triangle Institute (Research Triangle Park, N.C.). G3 polyamidoamine (PAMAM) dendrimers were purchased from Dendritic Nanotechnologies, Inc. (Mt. Pleasant, Mich.). All other reagents were purchased from Sigma Aldrich (St. Louis, Mo.) unless otherwise noted.

Cloning and large-scale expression of anti-METH scFv6H4Cys.

The generation, characterization, and sequence determination of murine mAb6H4 (IgG1, K light chain, KD=11 nM) and scFv6H4 (KD=10 nM) were previously reported (See, Byrnes-Blake, K. A. et al, 2003, *Eur. J. Pharmacol.* 461, 119-128 and Peterson, E. C. et al., 2007, J. Pharmacol. Exp. Ther. 322, 30-39). General molecular and genetic techniques used for plasmid construction and transformation of scFv6H4Cys were performed as described in Sambrook and Russell, 2001, Molecular cloning, CSHL Press. A carboxyl terminus cysteine was engineered immediately following the 6-histidine (His6) tag of scFv6H4 by DNA synthesis (Genscript, Piscataway, N.J.) to create scFv6H4Cys in pUC57 vector. The pUC57 scFv6H4Cys plasmid was transformed into *E. coli* strain DH5α (Invitrogen) for amplification and plasmid maintenance. The gene product was then restricted using EcoR1 and Xbal, gel purified, and ligated into the matching sites in cloning vector pPICZaA (Invitrogen). Ampicillin resistant colonies containing pPICZaA were selected on plates containing LB agar and ampicillin. DNA was isolated and the integrity of the transformed product was confirmed by restriction digest and DNA sequencing (University of Arkansas for Medical Sciences DNA Core Sequencing Facility). After sequence confirmation, the plasmid was linearized with SacI and used to transform *Pichia pastoris* strain X33 by electroporation according to manufacturers' instructions (Invitrogen).

Zeocin-resistant colonies containing the scFv6H4Cys cDNA were selected on yeast extract/peptone/dextrose/sorbitol agar plates [1% (wlv) yeast extract, 2% (w/v) peptone, 2% (w/v) dextrose, 1 M sorbitol and 2% agar] containing 100 µg/ml Zeocin. Colonies that exhibited high Zeocin resistance were tested for scFv6H4Cys expression. In brief, colonies were picked from a freshly streaked plate and grown for 24 hr in a 5 ml starter culture of BMGY [1% (w/v) yeast extract, 2% (w/v) peptone, 100 mM potassium phosphate, pH 6.0, 1.34% (w/v) yeast nitrogen base, $4 \times 10^{-5}$% biotin, and 1% (v/v) glycerol] at 30° C. Then 500 µl of this stater culture was inoculated in 50 ml of BMGY and cultured for additional 18 hr. The cells were harvested and resuspended in 500 ml BMMY [BMGY with 0.5% methanol (w/v) substituted for glycerol] to induce protein expression. The cultures were grown at 30° C. with shaking overnight and methanol was fed to a final concentration of 0.5% (w/v) at 24, 48 and 72 hr. To harvest and analyze total scFv6H4Cys expression, the samples were centrifuged at 20,000 g for 10 min, and the supernatant was analyzed using SDS-PAGE and coomassie dye G-250 based GelCode Blue staining (Pierce Thermo Scientific).

ScFv6H4Cys purification and formulation. The scFv6H4Cys expression product was purified using an AKTA explorer 100. FPLC system and a nickel sepharose immobilized affinity chromatography (IMAC) HiPrep FF16/10 column (GE Healthcare, Piscataway, N.J.). In brief, the column was equilibrated with 5 column volumes of binding/wash buffer (20 mM NaPO4, pH 7.4, 500 mM NaCl, 10 mM imidazole) and eluted in a single step with the elution buffer (binding/wash buffer with 500 mM final concentration of imidazole). The fractions were collected, pooled, buffer exchanged and concentrated into scFv administration buffer (15 mM NaPO4, 150 mM NaCl, pH 7.5) using 7 or 20 ml Pierce® concentrators with 9 kDa molecular weight cut off (MWCO) (Pierce Thermo Scientific). The protein was characterized by SDS-PAGE, Western blot, and N-terminal sequencing (Midwest Analytical Inc, St. Louis, Mo.).

Synthesis and characterization of $PEG_{24}$ modified G3 PAMAM dendrimers. A working stock of 0.1 mM G3 PAMAM dendrimers 1 (FIG. 1A) was prepared in phosphate buffered saline (PBS) (2.683 mM KCl, 1.47 mM $KH_2PO_4$, 136.893 mM NaCl, 8.101 mM $Na_2HPO_4$) (MP Biomedicals LLC, Solon, Ohio) containing 1 mM EDTA. The heterobifunctional crosslinker with NHS ester and maleimide groups with PEG 2 spacer arms (NHS-$PEG_{24}$-Mal) was added in 20, 15, 10 and 5 fold molar excess to the dendrimer working stock (e.g., 0.5 mM crosslinker to 0.1 mM dendrimer). The G3 dendrimer 1 and $PEG_{24}$ 2 conjugation reactions were set up in stoichiometric ratios such that a single $PEG_{24}$ molecule had 5, 11, 16 or 32 amine groups available to react with each dendrimer. The reaction was incubated at room temperature (RT) for 2 hr in the dark with gentle shaking. After incubation, excess of crosslinker and leaving NHS group were removed using protein desalting spin columns (Thermo Fisher Scientific) equilibrated with conjugation buffer (50 mM NaPO4, pH 6.4, 150 mM NaCl, 2 mM EDTA). $PEG_{24}$ modified G3 PAMAM dendrimers 3 were characterized using UV spectrometry, gel electrophoresis, and matrix-assisted laser desorption ionization-time of flight mass spectrometry (MALDI-TOFMS). A Nanodrop 1000 spectrophotometer (Thermo Fisher Scientific) was used to obtain UV spectra.

Gel electrophoresis: Reducing SDS-PAGE analysis was conducted using 4¬12% acrylamide Bis-Tris NuPage gels (Invitrogen) according to manufacturer's instruction. Samples were heated with sample loading buffer containing dithiothreitol (DTT) at 70-80° C. for 10 min and were run at 200 V for 35 min. The gel was stained with Coomassie based GelCode Blue for 1 hr at RT and destained overnight in water. For PEG-specific iodine staining, the gel was soaked in 5% barium chloride solution for 10 min and placed in 0.1 M iodine solution until a brown color developed.

MALDI-TOF analysis: MALDI-TOF mass spectra were obtained on a Bruker Ultraflex II TOF-TOF (Arkansas Statewide Mass Spectrophotometry Facility). A 1 M solution of 2,5-dihydroxybenzoic acid in 90% methanol with 0.1% formic acid (MALDI matrix) was mixed with the various reaction ratios of PEG$_{24}$ modified dendrimer 3 samples in a 1:1 ratio (v/v) and 1 µL of the mixture was deposited onto the MALDI target. Mass spectra were acquired in the linear, positive ion mode and externally calibrated with a protein standard mixture.

Synthesis and optimization of PEG$_{24}$ modified G3 PAMAM dendrimer 3 and scFv6H4Cys 4 conjugation reactions. The individual parameters of the dendribody 5 reaction were optimized (i.e., reaction ratios of PEG modified dendrimers 3 to scFv6H4Cys 4, type and concentration of reducing agent, pH, temperature, EDTA, and NaCl concentration) to obtain the maximum dendribody 5 yield. The reaction was performed in conjugation buffer at pH 6.2, 6.4, 6.6, 6.8, 7.0 and 7.2. The optimum reaction pH (6.4) was then allowed to proceed at 4° C. 25° C. and 37° C. to determine the optimum temperature. To ensure that the scFv6H4Cys's 5 thiol groups remained in their reduced state, two reducing agents TCEP (tris-2-carboxyethyl phosphine) and DTT at various concentrations were explored. The scFv6H4Cys was treated with freshly prepared 2, 4, 6, 8 and 10 mM DTT or TCEP concentrations equal to 2, 5, or 10 fold the protein concentration. These reduction reactions were allowed to proceed for 2 hr at RT in dark with shaking. The TCEP and DTT treated scFv6H4Cys 5 was desalted using Pierce® desalting spin column into the conjugation buffer. The DTT treated scFv6H4Cys was desalted twice to ensure complete removal of DTT as confirmed by Ellman's assay (Thermo Fisher Scientific). The reaction ratio of 15-fold excess of PEG$_{24}$ 2 to G3 PAMAM dendrimers 1 was reacted immediately with a three molar excess of reduced scFv6H4Cys 4. This reaction was allowed to proceed for 2 hr at RT in the dark with shaking to produce dendribodies.

Characterization of PEG24 modified G3 PAMAM dendrimers and scFv6H4Cys Conjugates (dendribodies). Dendribodies 5 were characterized using SDS-PAGE, size exclusion chromatography (SEC), and Western blot. Gel electrophoresis was performed as described for PEG$_{24}$ modified dendrimers 3 and was used to assess the efficiency of crosslinking. Western blot was used to detect the presence of scFv6H4Cys 4 in the higher molecular weight dendribody 5 bands. The gel was electrophoretically transferred to a polyvinylidine fluoride (PVDF) membrane using a XCell SureLock™ Mini-Cell Western blotting kit (Invitrogen) as per manufacture's instruction. The membranes were then blocked with 10% non-fat dry milk overnight at 4° C. and incubated for 2 hr at RT with 1:5000 mouse monoclonal ANTI-FLAG® M2-Alkaline Phosphatase antibody (Invitrogen) made in 0.2% bovine serum albumin (BSA, Biorad Laboratories Inc., Hercules, Calif.). Following incubation, the membrane was washed with tris-buffered saline (+0.1% Tween-20, three times with five minutes per rinse). Bands were identified by exposing the membrane to 5-bromo-4-chloro-3-indolyl-phosphate in conjunction with nitro blue tetrazolium for colorimetric detection.

Purification of the dendribodies 5 from the unreacted PEG$_{24}$ modified G3 PAMAM dendrimers 3 and scFv6H4Cys 4. The dendribodies 5 were purified by immobilized metal affinity chromatography (IMAC) using an AKTA Explorer 100 FPLC system and a 1 ml HiTrap IMAC FF column. In brief, the column was equilibrated with five column volumes of binding/wash buffer (containing 10 mM imidazole) at 1 ml/min. The dendribody reaction mixture containing the unreacted PEG$_{24}$ modified dendrimers 3, unconjugated scFv6H4Cys 4 and dendribodies 5 was loaded onto the column. The dendribodies 5 were eluted from the column with the elution buffer (binding/wash buffer plus 470 mM imidazole, pH of 7.5) and collected as 0.5 ml fractions. The elution profile was monitored by UV absorbance at 220, 254, and 280 nm wavelengths. Fractions were analyzed by SDS-PAGE and the fractions enriched in dendribodies 5 were pooled and concentrated into PBS using 3 kDa MWCO Vivaspin concentrators (GE Healthcare).

Saturation binding assay for determination of KD values for METH. Rapid equilibrium dialysis (RED) (Pierce Thermo Scientific) device was used to perform the saturation binding assay. The Teflon base plate was placed in 20% v/v ethanol for 10 min for washing. After ethanol removal, the base plate was thoroughly rinsed three times with water and allowed to dry. RED inserts with a nominal MWCO of 6-8 kDa were used. The concentration of scFv6H4Cys 4 or dendribodies 5 that binds 20% [3-1]-METH was added to the sample chamber. This protein concentration was determined using a titration binding assay where serial dilutions of scFv6H4Cys 4 or dendribodies 5 were allowed to bind a constant concentration of [$^3$H]-METH. For total binding, 100 µl of PBS and 200 µl of increasing concentrations of [$^3$H]-METH were added into the buffer chamber. For nonspecific binding, 100 µl of PBS was replaced by 100 µl of 10 µM unlabeled METH as a competitor for $^3$H-METH. After loading, the plates were sealed with self-adhesive plastic sealing sheets to prevent evaporation and incubated overnight at RT on an orbital shaker with gentle shaking. After equilibrium was reached (18 hr), an aliquot of (50 µl) of the sample solution, from both the sample and buffer sides, was added to 5 ml of scintillation fluid and vortexed. [$^3$H]-METH was quantified using liquid scintillation spectrophotometry.

Data analysis and statistics. Data represent mean±standard error of the mean (S.E.M) for the number (n) of experiments indicated in parentheses.

Example 2

Dendribody Synthesis

Sulfhydryl specific crosslinking was used to conjugate the anti-METH antibody fragment to dendrimers. This conjugation strategy was chosen because it is effective for coupling proteins to non-protein molecules, such as detection molecules, PEG, and liposomes. The basis of the chemistry is to utilize the selective reactivity of the thiol side chain of a cysteine residue in the protein sequence with the maleimide of the heterobifunctional PEG linker. The IgG inherently possess cysteines that form intrachain disulfide bonds in the variable light and heavy chains, however conjugating to these internal cysteines groups could disrupt the structure of the antibody and ligand binding. Thus we engineered a scFv with a cysteine at the carboxy-terminus of the DNA coding sequence to create scFv6H4Cys (FIG. 1C).

Figure 1B:
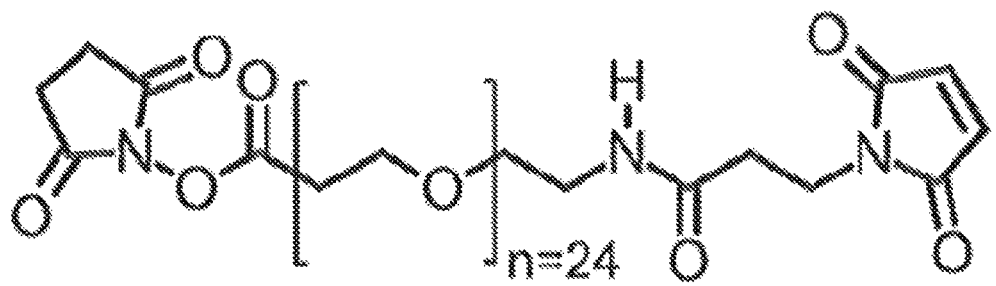
Figure 1C:
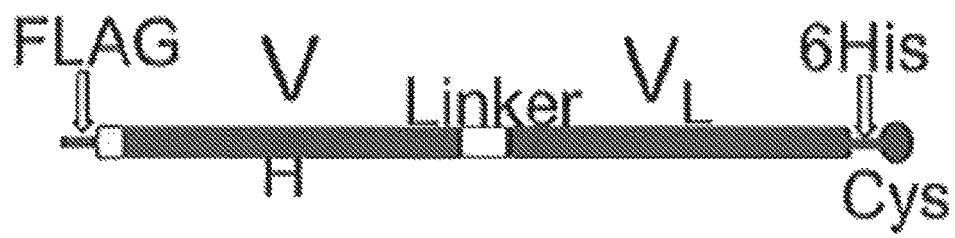

G3 PAMAM dendrimer was used as the supporting scaffold of the dendribody (FIG. 1A). G3 PAMAM dendrimers consist of a diaminobutane core that has undergone three generations of synthesis, doubling the number of functional groups with each progressive generation. The G3 PAMAM dendrimer possesses a maximum number of 32 amine terminal groups, which can be utilized for conjugation with a variety of homo- and heterobifunctional crosslinking agents. A heterobifunctional 1270 Da PEG (24 ethylene oxide repeats) crosslinker that is reactive to amines via an NHS ester at one terminus and to a free sulfhydryl group via a maleimide group at the opposite terminus (FIG. 1B) was chosen.

Figure 2:
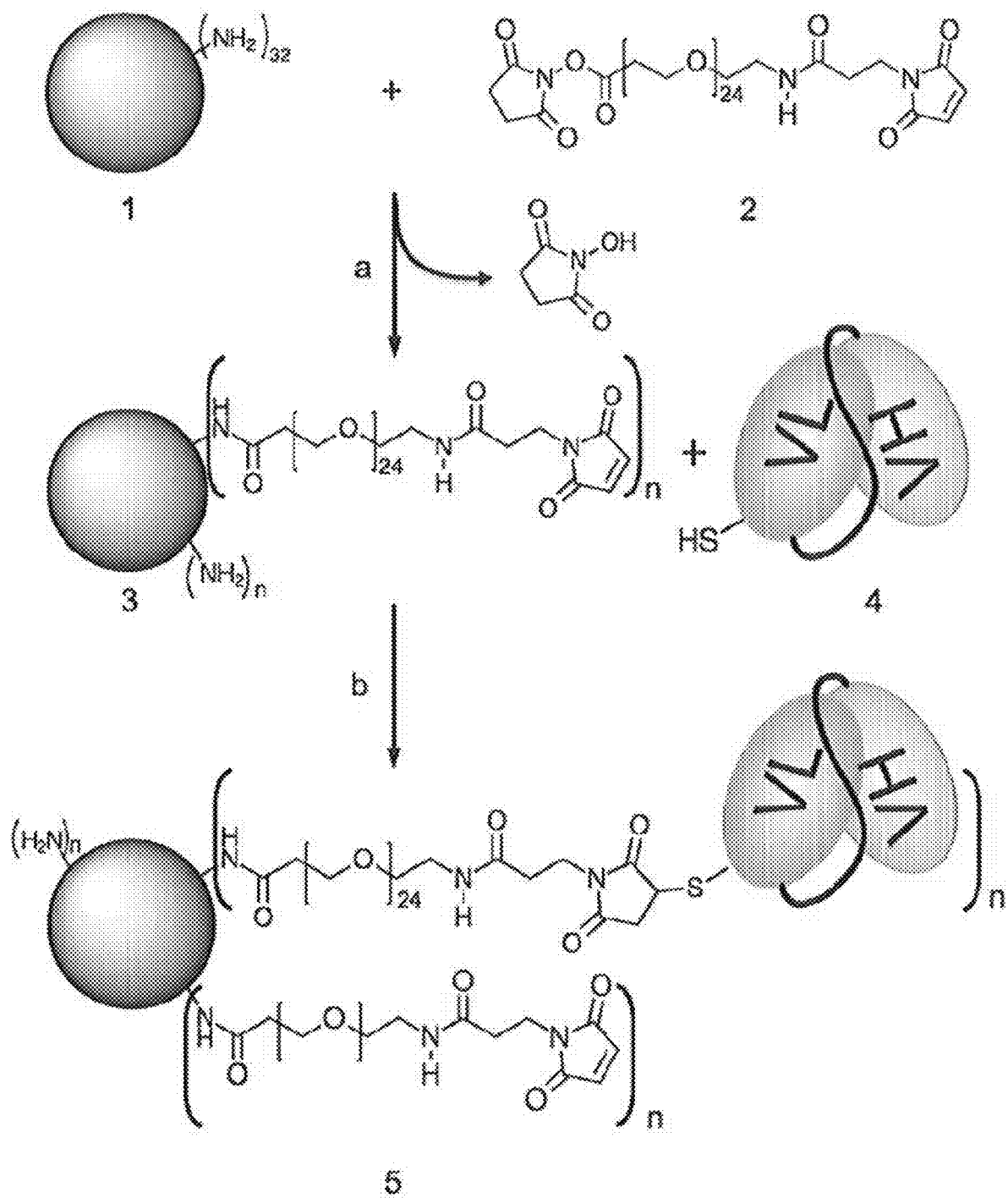
FIG. 2 depicts a schematic of the synthesis of anti-METH scFv6H4Cys-dendrimer conjugates (dendribodies). Specifically, G3 PAMAM dendrimer (1) is reacted with a heterobifunctional PEG$_{24}$ crosslinker (2) to produce PEG modified dendrimer (3) along with the loss of NHS group. Then, (3) is conjugated to reduced scFv6H4Cys (4), via a thioether bond to produce the dendribody (5). Reagents and conditions (a) PBS, pH 7.4, 2 mM EDTA, room temperature, dark, shaking, 2 hours (hr); (b) 50 mM NaPO$_4$, pH 6.4, 150 mM NaCl, 2 mM EDTA, room temperature, dark, shaking, 2 hr.

The general steps to assemble the dendrimer-PEG-scFv6H4Cys conjugate are represented schematically in FIG. 2. Briefly, the first step was to crosslink the NHS-moiety of the heterobifunctional PEG 2 to the amine terminal groups of the G3 PAMAM dendrimer (1), followed by removal of unreacted dendrimers and PEG by desalting chromatography (FIG. 2). Step two was to reduce the carboxy-terminal cysteine of the scFv6H4Cys (4) with DTT reducing agent followed by a desalting step (FIG. 2). This step was found to be important for three reasons. First, it reduces any scFv dimer interactions that were mediated by disulfide bonds. Second, and most importantly, this reduction step reduced any potential disulfide interactions that occurred in the cell growth media during the scFv production in the presence of sulfhydryl-containing amino acids or peptides. The desalting step removes these small adducts and DTT, both of which could compete and interfere with the maleimide reaction in the next step. Third, it served as a quick method of buffer exchange.

Once the $PEG_{24}$ modified dendrimer (3) and reduced scFv6H4Cys (4) were desalted and buffer exchanged, they were combined and the free sulfhydryl groups of the scFv6H4Cys were covalently linked to the maleimide groups of the PEG modified dendrimer (3) to form the final dendribody (5) products. FIG. 2 represents a single scFv bound to the PEG modified dendrimer (3) for illustration purposes. However, higher order conjugates are possible and this was the goal of the optimization experiments herein presented.

Example 3

PEG Modification of G3 PAMAM Dendrimers

In order to control the degree of PEG modification of the dendrimers, the crosslinking reaction of NHS-PEG-maleimide (2) to G3 PAMAM dendrimer (1) was performed with PEG:G3 stoichiometric ratios of 5:1, 11:1, 16:1 and 32:1 (FIG. 2). In this reaction, the NHS cyclic group leaves after reacting with the dendrimer's free terminal amine. The NHS leaving group and unreacted PEG (2) crosslinker were removed to increase the efficiency of later steps of the dendribody (5) synthesis (FIG. 2).

Figure 3A:
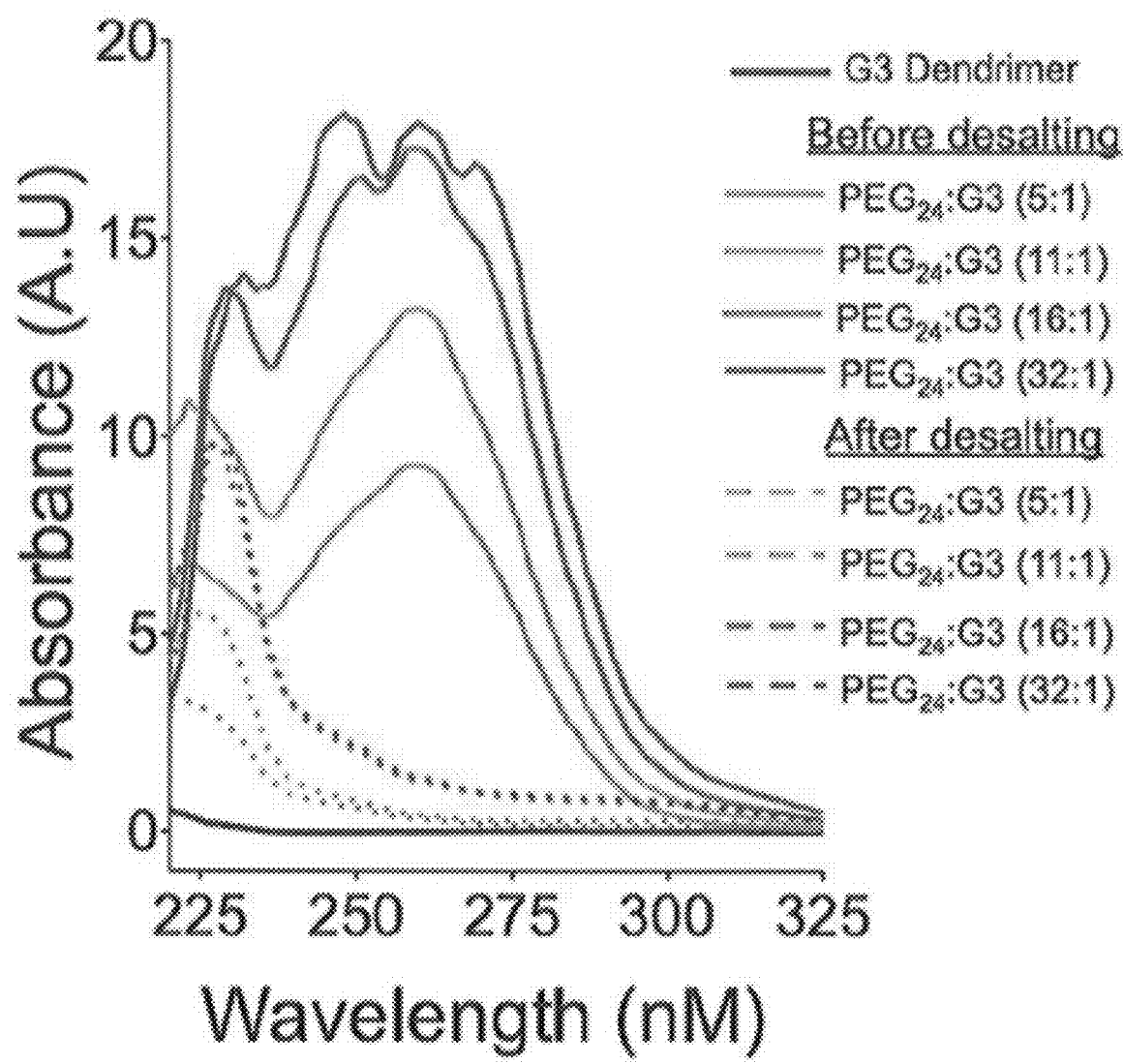
FIG. 3A and FIG. 3B depict the relative degree of PEG modification of the dendrimer.

An amide bond is formed when the NHS-ester reacts with dendrimer amines releasing N-hydroxysuccinimide. Hydrolysis of the NHS-ester is a major competing reaction of the NHS-ester acylation reaction. The NHS group is released by both the reaction with the primary amines and by hydrolysis. Thus, the extent of hydrolysis or reaction with the primary amines of NHS-esters in solution can be determined by measuring the absorbance at 260 nm, the NHS-ester group. Dendrimers do not exhibit UV absorption at this wavelength. This difference in spectral absorption was used to follow the efficiency of the desalting reactions as well as the relative degree of PEG modification of dendrimer at increasing stoichiometric reaction ratios (FIG. 3A).

Figure 3B:
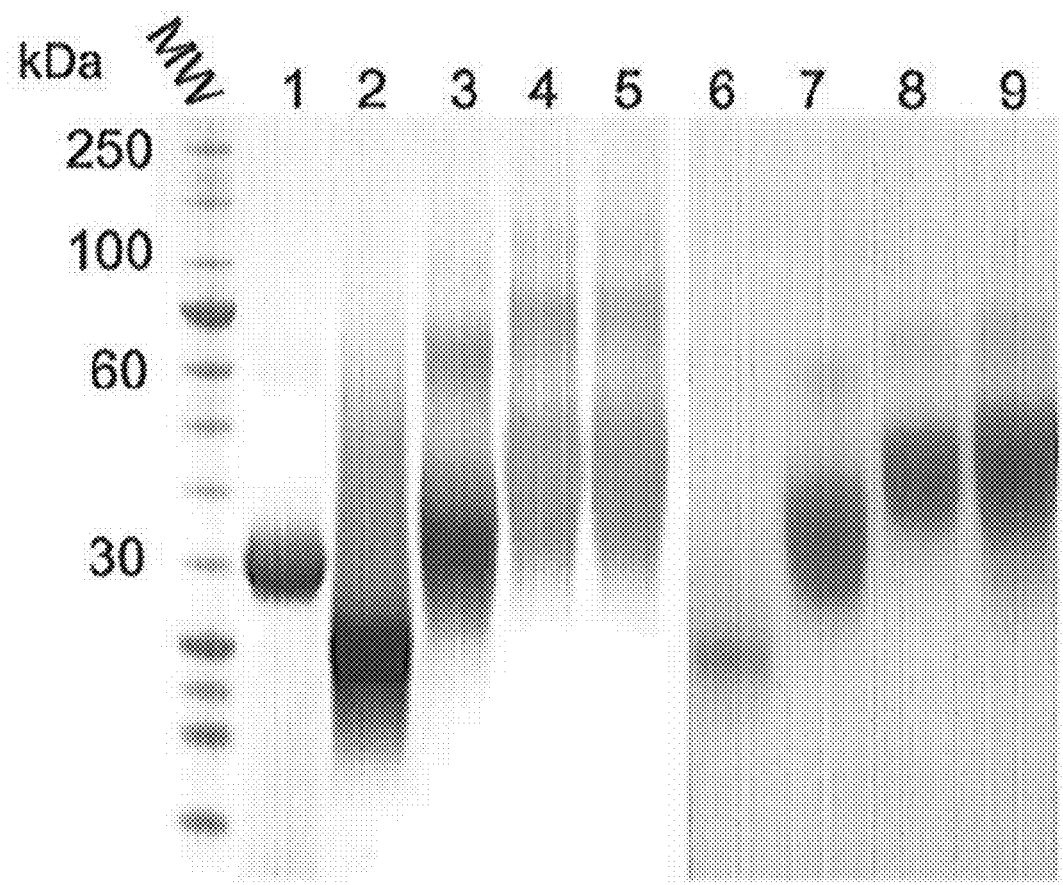

Following desalting and spectrophotometric analysis, the degree of PEG modification of dendrimer was further analyzed by SDS-PAGE. The amine-terminated PAMAM dendrimers 1 exhibit a net positive charge and do not migrate into standard polyacrylamide gels, even in the presence of SDS. However, they can be analyzed if the SDS-PAGE is conducted with reversed polarity. While this technique was useful for analyzing the dendrimer alone, it was of little utility since the other reactants (PEG 2 and scFv6H4Cys 4) in the dendribody synthesis could not be analyzed in the same reverse-polarized gel. The PEG 2 crosslinker alone migrated into SDS-PAGE gel, however it could not be detected with Coomassie-based stains. Once the PEG crosslinker 2 and the PAMAM dendrimer 1 were conjugated, the new PEG modified dendrimer 3 migrated into SDS-PAGE gels and could be monitored with Coomassie-based stain (FIG. 3B). The PEG modified dendrimer 3 migrated in a pattern that reflected the size increase resulting from the stoichiometric changes in PEG:G3 dendrimer reactions. As the ratio of PEG crosslinker was increased, an apparent higher shift in the molecular weight of each band was observed suggesting increased functionalization of the dendrimers with saturation at higher PEG concentrations (FIG. 3B, left panel, lanes 1-5). The molecular weight increase was due to the addition of PEG crosslinker by staining a duplicate SDS-PAGE with PEG-specific iodine stain (FIG. 3B, right panel, lanes 6-9). This analysis provided a useful insight into the relative degree of PEG modification of the dendrimers. Interestingly, as the degree of PEG functionalization increased, the ability of the conjugates to be detected by Coomassie-based stain decreased.

Example 4

Analysis of PEG Modified Dendrimers

While the SDS-PAGE analysis strongly indicated successful PEG 2 modification of the G3 PAMAM dendrimers 1, and that it appeared to be a saturable process, this needed to be confirmed by MALDI-TOF analysis. MALDI-TOF was a more accurate technique for analyzing the mass of G3 PAMAM dendrimers 1, $PEG_{24}$ crosslinker 2, and the products of each PEG:G3 dendrimer reaction.

Figure 4A:
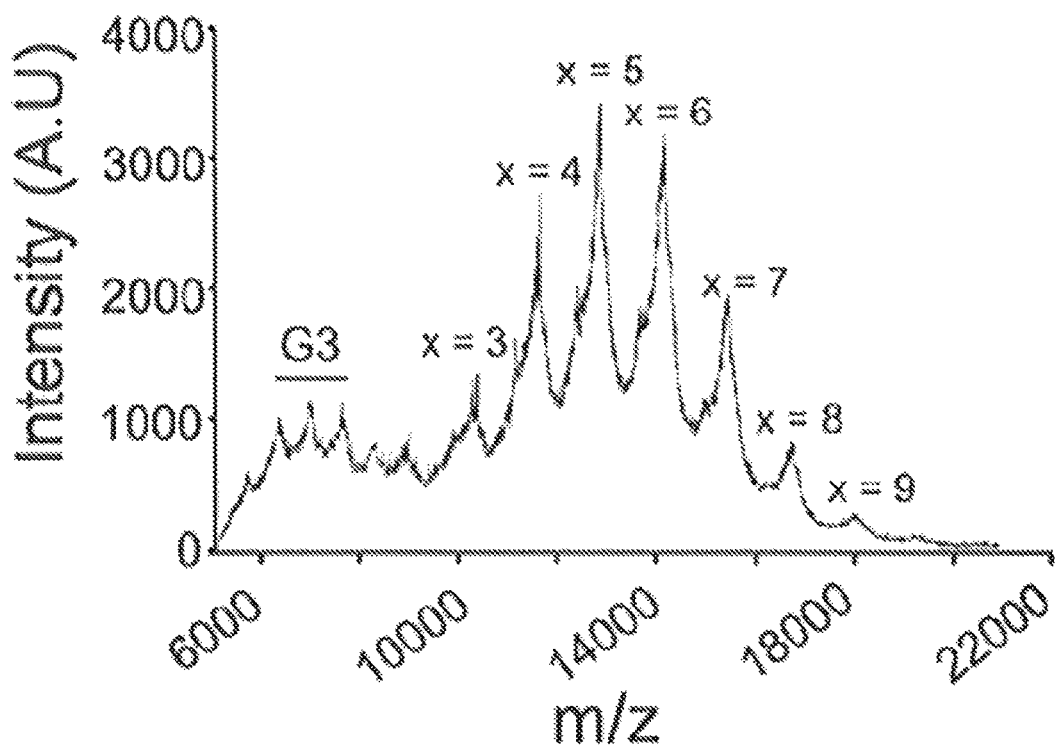
FIG. 4A and FIG. 4B depict MALDI-TOF analysis of PEG modified dendrimers.

MALDI-TOF analysis suggested that the average mass of the G3 PAMAM dendrimers 1 and $PEG_{24}$ 2 crosslinker alone was 6937 Da and 1280 Da respectively (Table 1) which closely agreed with the mass reported by the manufacturer. Each of the PEG24:G3 optimization experiments showed increasing mass as the ratio of PEG to dendrimer was increased in the reaction, confirming the SDS-PAGE results. The MALDI-TOF spectra showed a distribution of individual mass peaks. FIG. 4A is a representative spectrum from the 5:1 PEG:G3 dendrimer reaction ratio. In addition to a broad peak that corresponds to the mass of the G3 dendrimer 1 alone, several individual peaks were observed that iteratively increased by 1280 Da, corresponding to the theoretical mass addition of each PEG 2 crosslinker.

TABLE 1

The theoretical and experimental mass additions of $PEG_{24}$ to G3 PAMAM dendrimers corresponding to each reaction ratio of $PEG_{24}$:dendrimer.

| $PEG_{24}$:G3 reaction ratio | Theoretical MW[a] Da | MALDI-TOF[b] m/z | PEG/G3 ratio |
| --- | --- | --- | --- |
| 5:1 | 13324.05 | 13144 | 5 |
| 11:1 | 20998.11 | 29259 | 16 |
| 16:1 | 27393.16 | 34126 | 20 |
| 32:1 | 47857.32 | 34913 | 20 |

[a]Theoretical mass addition by G3 dendrimer and $PEG_{24}$ is 6929 and 1279 Da, respectively.
[b]Experimental mass addition by G3 dendrimer and $PEG_{24}$ is 6937 and 1280 Da, respectively.
The apparent molecular weights of $PEG_{24}$ and dendrimer were obtained from the manufacturers and calculated from MALDI-TOF spectra.

As the $PEG_{24}$:G3 stoichiometric ratio increased, an upward shift in the overall mass was observed, but there was also reduced resolution of the individual mass peaks. Thus, for the calculation of the average number of PEG 2 additions to the dendrimer 1, the mass of the highest peak, or group of peaks was selected. For this reason, the predominant, or highest signal peak was reported in Table 1 and it was assumed that each reaction resulted in a Gaussian distribution of PEG molecules incorporated around this central peak.

Figure 4B:
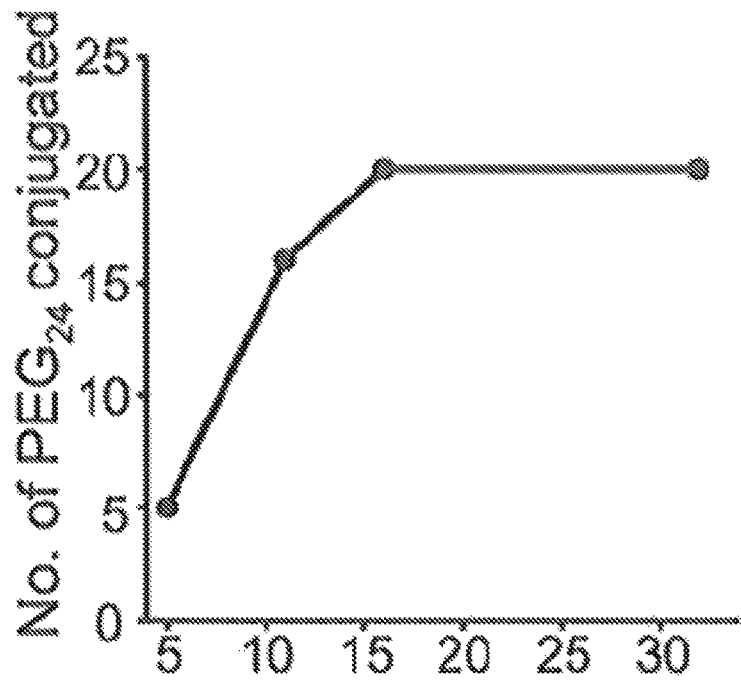

The mass increase for the 5:1, 11:1, 16:1, and 32:1 PEG24:G3 reaction ratios corresponded to 5, 16, 20, and 20 PEG 2 additions, respectively (FIG. 4B and Table 1). Surprisingly, there was over 100% addition of the calculated PEG 2 to the dendrimers 1. One explanation for this observation could be the difference in the reported and actual concentration of $PEG_{24}$ 2 crosslinker or G3 PAMAM dendrimers lots 1. Nevertheless, a saturation between 16:1 to 32:1 PEG to dendrimer reaction ratio similar to the SDS-PAGE analysis was observed with a maximum addition of 20 PEG units per dendrimer. This suggested that after crosslinking up to 63% of the available amines on the dendrimer (FIG. 4B) were occupied with PEG. It was not an aim to saturate the dendrimers with PEG since excess unreacted PEG can be difficult to remove from the products. Therefore, the 11:1 PEG24:G3 dendrimer reaction ratio was selected to synthesize the PEG modified dendrimer scaffolds for dendribody production.

Example 5

Crosslinking of scFv6H4Cys to PEG Modified Dendrimers and Optimization

Once the analysis of the PEG modified dendrimer 3 indicated that the degree of PEG incorporation onto the surface of the dendrimer could be regulated by controlling the stoichiometry of the reaction, a series of experiments aimed at optimizing the attachment of multiple scFv6H4Cys 4 molecules to the PEG modified dendrimer scaffold were initiated. These optimization experiments included varying numerous parameters known to affect maleimide-thiol reaction efficiency including: scFv to dendrimer stoichiometric ratio, ionic strength, EDTA concentration, temperature, and pH.

Figure 5A:
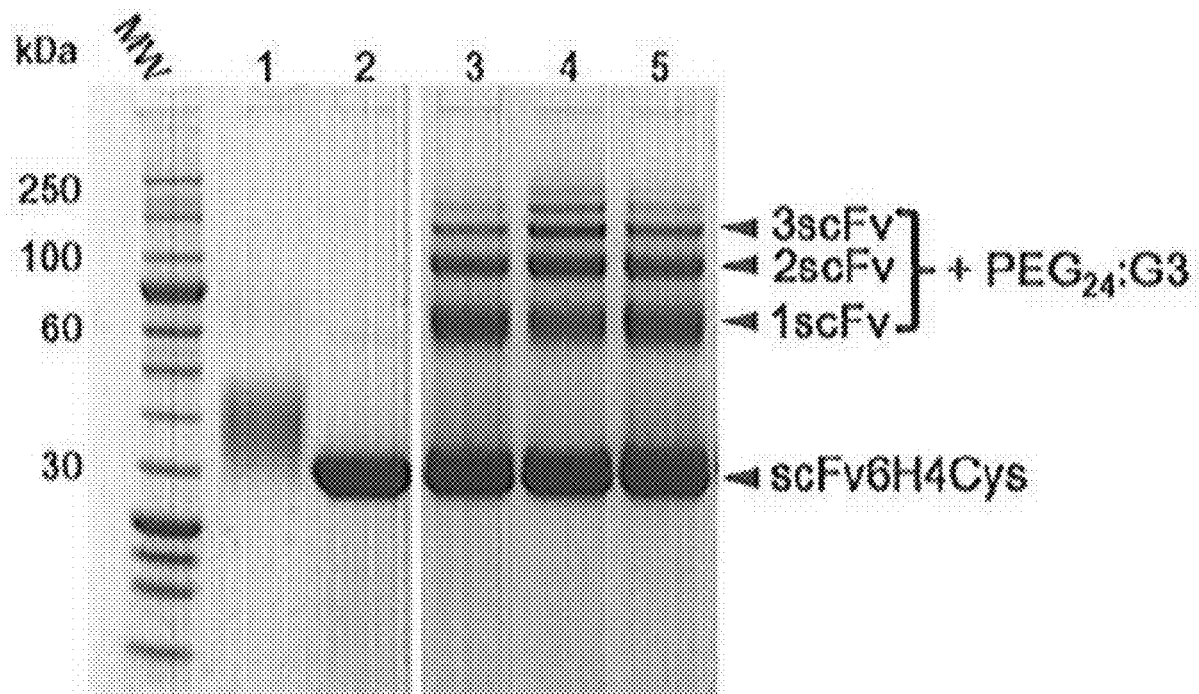
FIG. 5A and FIG. 5B depict the optimization and crosslinking of scFv6H4Cys to PEG modified dendrimers.

The endpoint of the reaction efficiency was the number of scFv6H4Cys 4 molecules that could be linked to the PEG modified G3 dendrimer 3 core. The number of scFv6H4Cys 4 on each dendrimer could be determined since the reaction products formed distinct and well-resolved bands in an SDS-PAGE gel. Both the maximum number of higher-order conjugates, as well as the relative amounts of each species were carefully examined. To determine if temperature influenced the reaction efficiency, the dendribody conjugation was allowed to proceed at 4°, 25°, and 37° C. for 2 hrs, and analyzed by SDS-PAGE (FIG. 5A). The reaction temperature had moderate effect on the efficiency of the reaction, with the 25° C. condition having a slightly higher efficiency in the number of scFv6H4Cys 4 molecules conjugated to PEG modified dendrimers. NaCl and EDTA concentrations had negligible effects on the efficiency of the reaction.

Figure 5B:
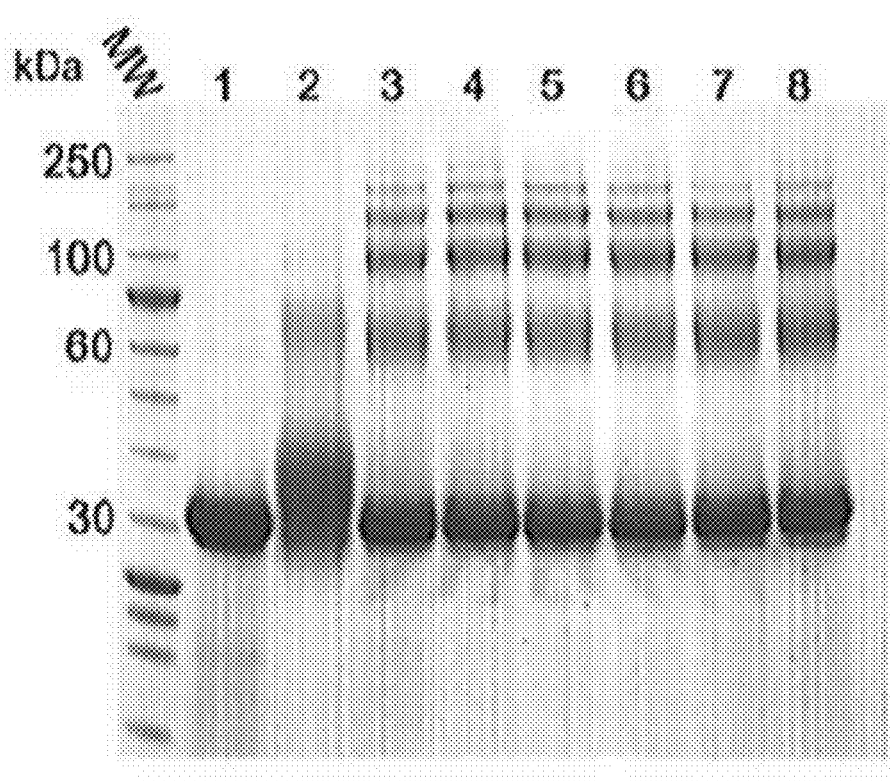
Figure 6A:
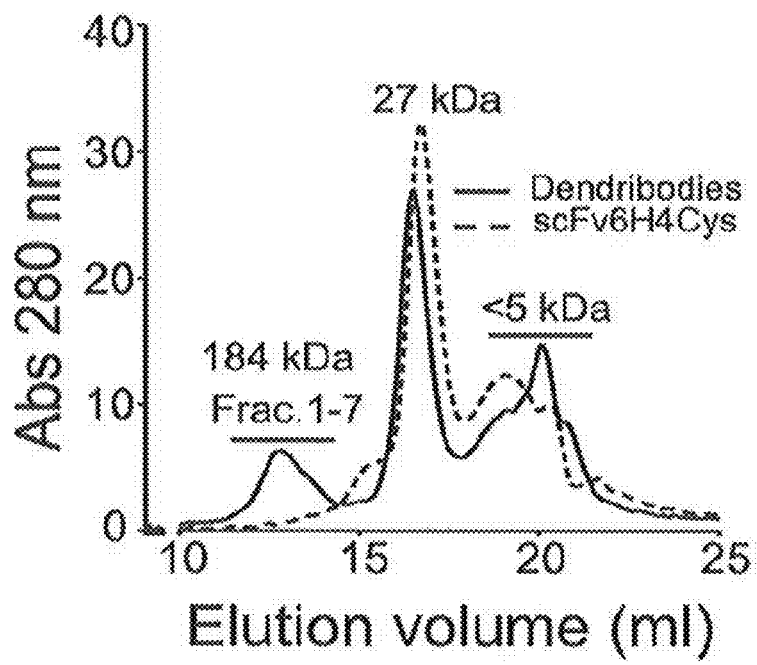
FIG. 6A and FIG. 6B depict that the DTT reduced scFv6H4Cys exists in vitro mainly as a monomer.
Figure 6B:
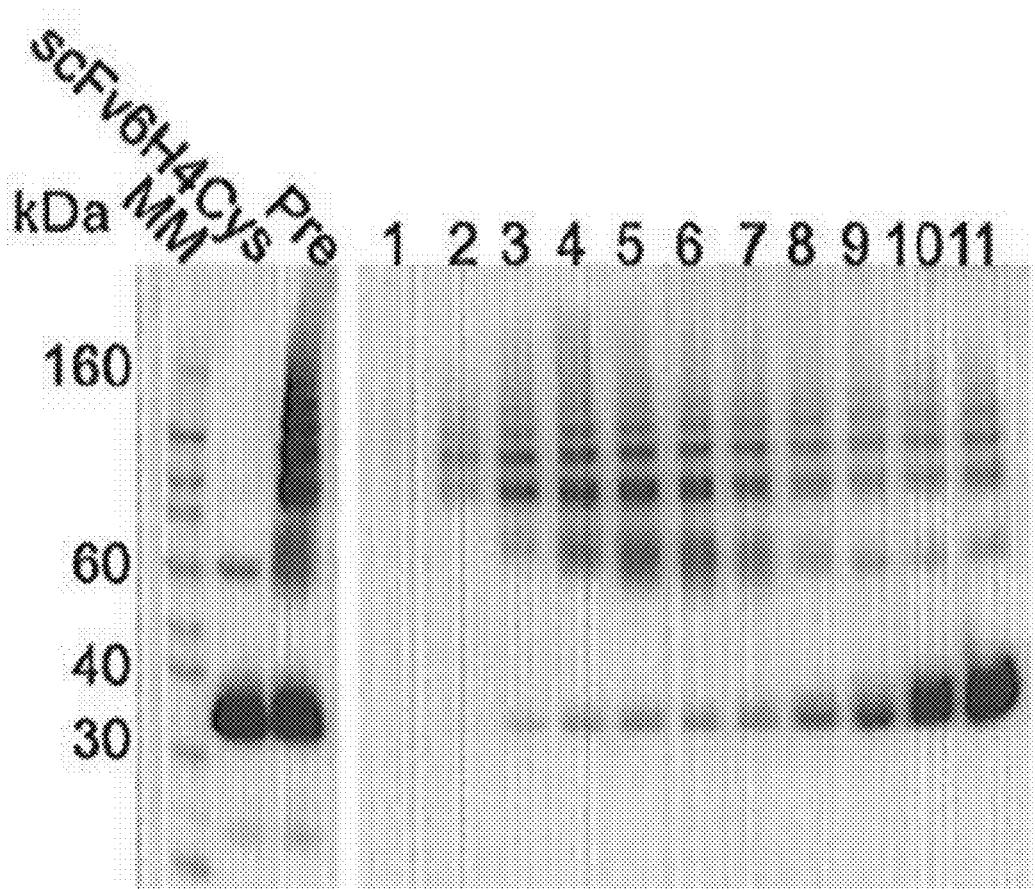

To determine how buffer pH affected the crosslinking efficiency, six reactions in the pH range from 6.2-7.2 were conducted. This range was selected based on manufacturer's instructions, previous reports, and on using a pH range compatible with the isoelectric point of our protein (calculated pI of scFv6H4Cys=6.2). The optimal reaction pH was found to be 6.4 (FIG. 5B). A Western blot (FIG. 6B) probed with an anti-FLAG antibody further confirmed that the discrete banding pattern observed for the dendribodies 5 in the SDS-PAGE analysis was indeed from the addition of increasing numbers of scFv6H4Cys 4 to the PEG modified dendrimers 3.

Example 6

Purification of Dendribodies by Immobilized Metal Affinity Chromatography

For the functional assay, it was first necessary to separate the prototype dendribodies 5 from the unconjugated PEG modified dendrimers 3 and scFv6H4Cys 4. We attempted several chromatographic purification techniques, including ion exchange (IEX) and size exclusion chromatography (SEC). These two approaches were not suitable due to either incomplete separation (IEX), or poor recovery of the product (SEC). Since not all of the possible IEX resins were explored, it is still possible that this method could be used in the future.

Figure 7A:
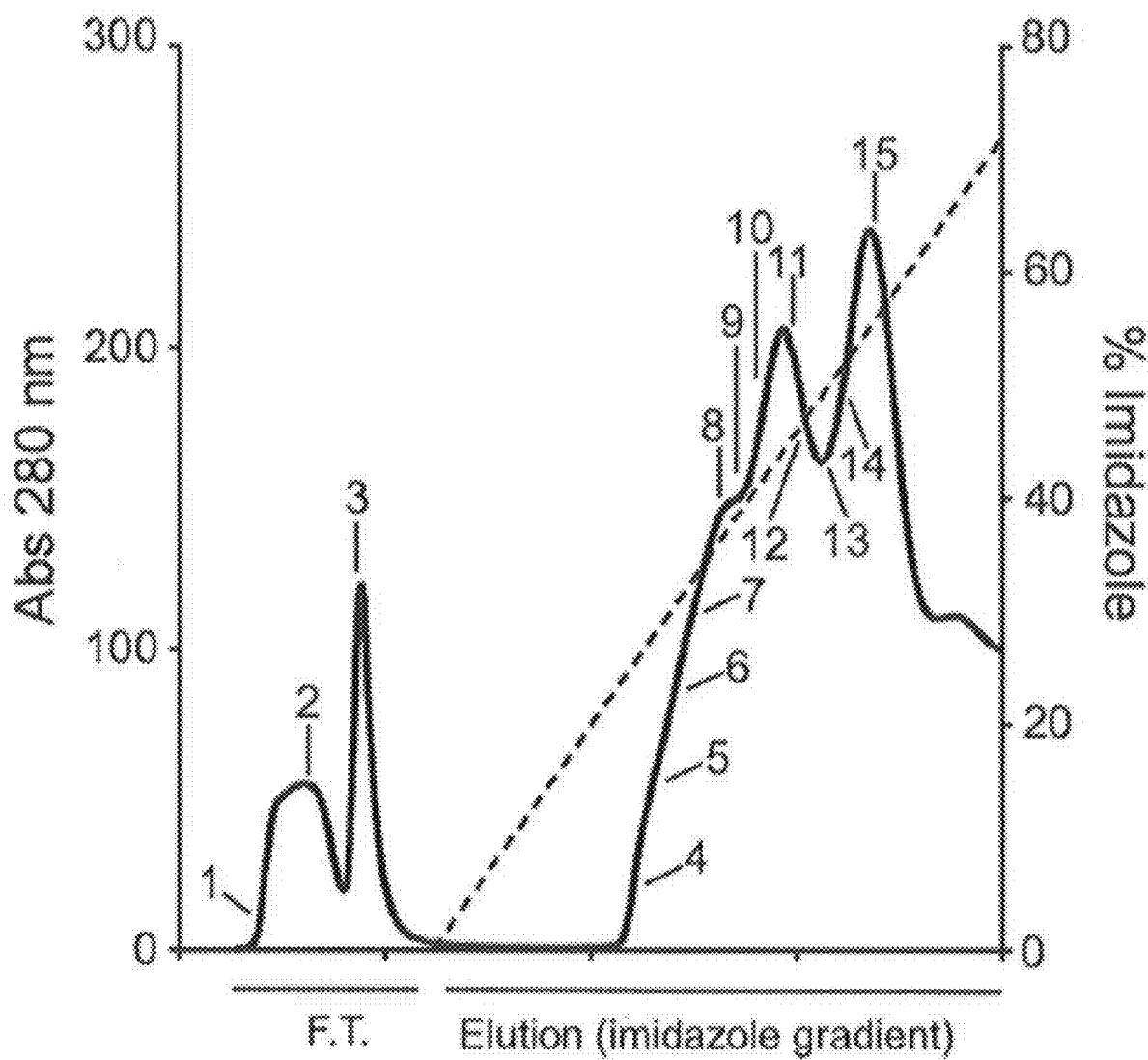
FIG. 7A, FIG. 7B and FIG. 7C depict the purification of the dendribodies by immobilized metal affinity chromatography.
Figures 7B, 7C:
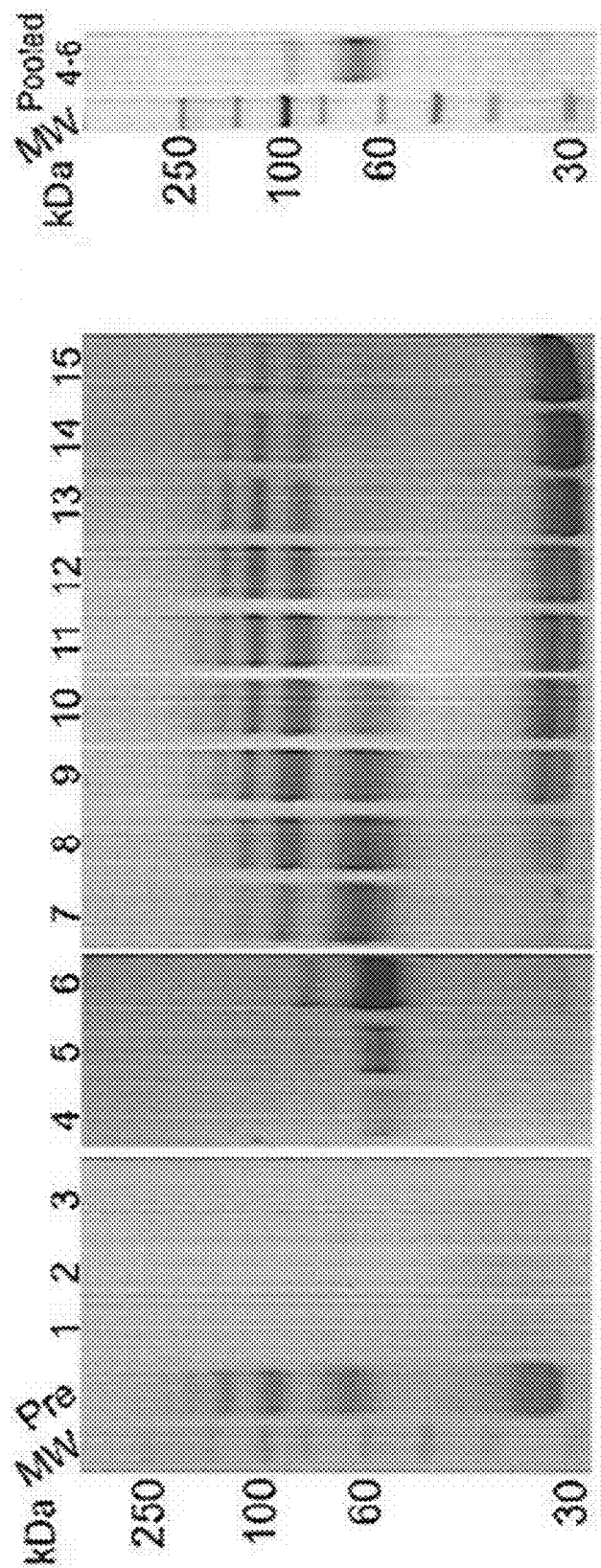

Ultimately, the His6 tag of scFv6H4Cys 4 was used for purification. The dendribody reaction mixture was applied to a Ni(II) affinity column and eluted with an imidazole gradient over 20 column volumes. The multiple dendribodies and reactants eluted at different points in the imidazole gradient, presumably due to their relative strength of interaction with the immobilized nickel groups on the chromatography resin. Unreacted PEG modified dendrimer did not bind to the IMAC column and was detected in the flow through fractions (FIGS. 7A and 7B). Dendribodies with lower number of scFv6H4Cys were eluted in the early fractions with low imidazole concentrations whereas the higher-order dendribodies eluted later with increasing imidazole concentration. Unreacted scFv6H4Cys eluted from the column predominantly in the later fractions with a peak around 50% (or 235 mM) imidazole. The early elution fractions (FIG. 7B, lanes 4 through 6) enriched in lower order dendribodies were pooled, concentrated and analyzed by Western blot. The Western blot confirmed that the pooled fraction was enriched in dendribodies. This confirmation was important since the lower order dendribodies migrate to a similar position on a gel as PEG modified G3 dendrimers. (FIG. 7C)

Example 7

Determination of In Vitro Activity of Dendribodies

For initial in vitro functional testing of the dendribodies, a saturation binding equilibrium dialysis assay was performed. To determine if the prototype dendribodies retained METH-binding function (capacity and affinity), a saturation binding equilibrium dialysis experiment was performed using a scFv6H4Cys and dendribody concentration capable of binding ~20% of a 50,000 dpm $^3$H-METH solution. This initial titration was performed to find a protein concentration that would provide a good signal-to-noise $^3$H-METH binding ratio at low concentrations while minimizing the effects of ligand depletion.

Figure 8:
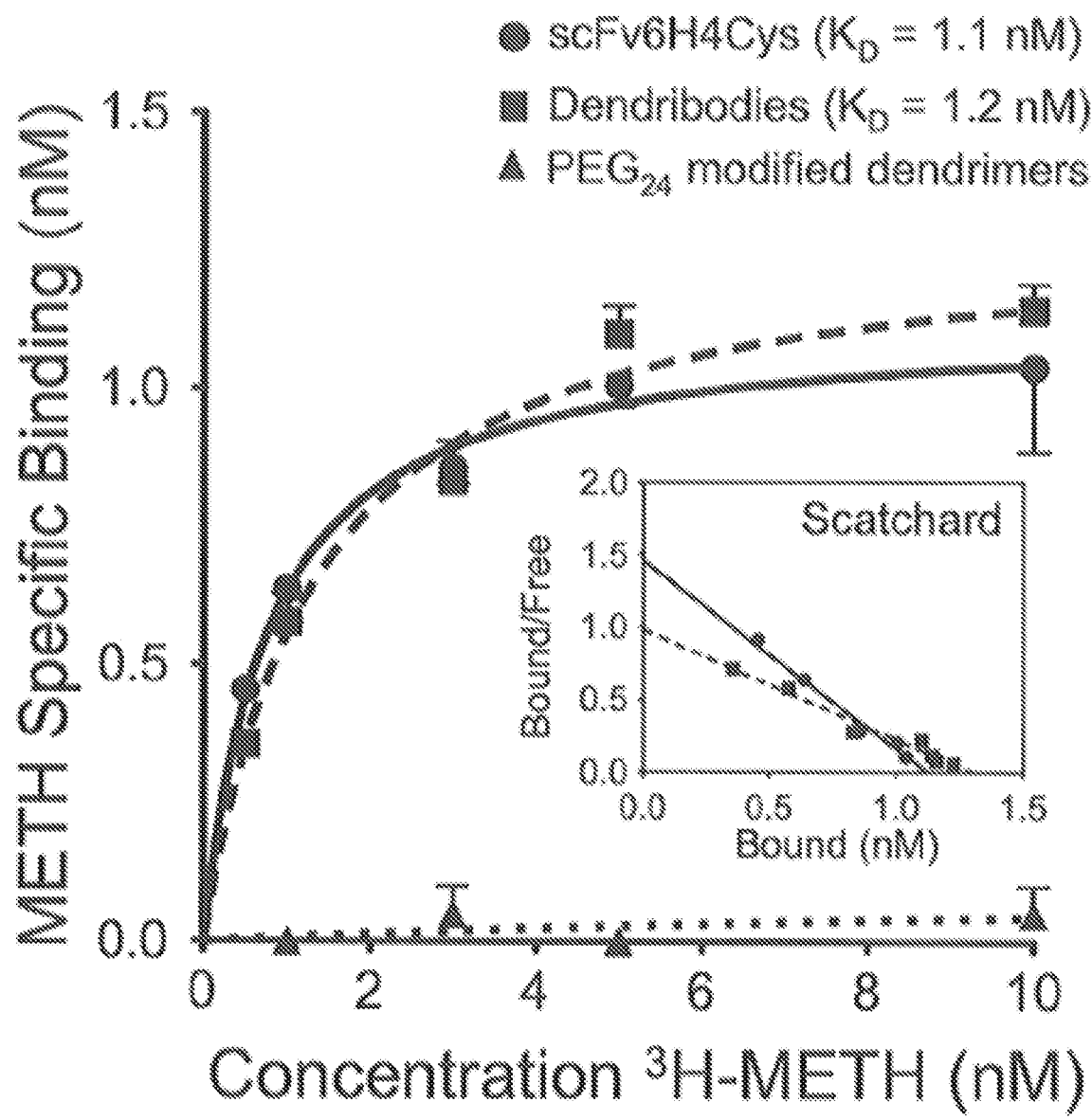
FIG. 8 graphically illustrates the binding affinity of scFv6H4Cys, dendribodies and $PEG_{24}$ modified dendrimers to METH. ScFv6H4Cys retained affinity for $^3$H-METH after conjugation to the dendrimers. $K_D$ values for $^3$H-METH were determined from Scatchard plots (presented in insets). Data points are the mean±S.E.M of triplicate determinations.

The absolute affinities of the unreacted scFv6H4Cys (4) and the purified lower-order dendribodies (5) were compared. The affinities, as measured by the dissociation constant (KD) of the dendribodies (5) and scFv6H4Cys (4) to $^3$H-METH, were 1.2 nM and 1.1 nM, respectively (FIG. 8). The PEG modified dendrimers showed little nonspecific binding to $^3$H-METH. The KD for scFv6H4Cys (4) differed from that previously published for parent scFv6H4 (KD=10 nM) (Peterson, E. C. et al., 2008, *J. Pharmacol. Exp. Ther.*

325, 124-133), but since a bead-based radioimmunoassay and not saturation binding equilibrium dialysis was used in the previous work, the inherent discrepancies in these assays likely account for the difference in reported affinity. Nonetheless, the results indicate that a high affinity anti-METH antibody can be successfully conjugated to a PEG modified nanoparticle with no apparent loss of affinity to its ligand.

The scFv6H4Cys retained its affinity for METH in the conjugated form, indicating that the conjugation process had little effect on the binding pocket of the protein.

Example 8

Cloning of Anti-METH scFv6H4

Figure 9A:
FIG. 9A and FIG. 9B depict the design, expression and purification of anti-METH scFv6H4.
Figure 9B:
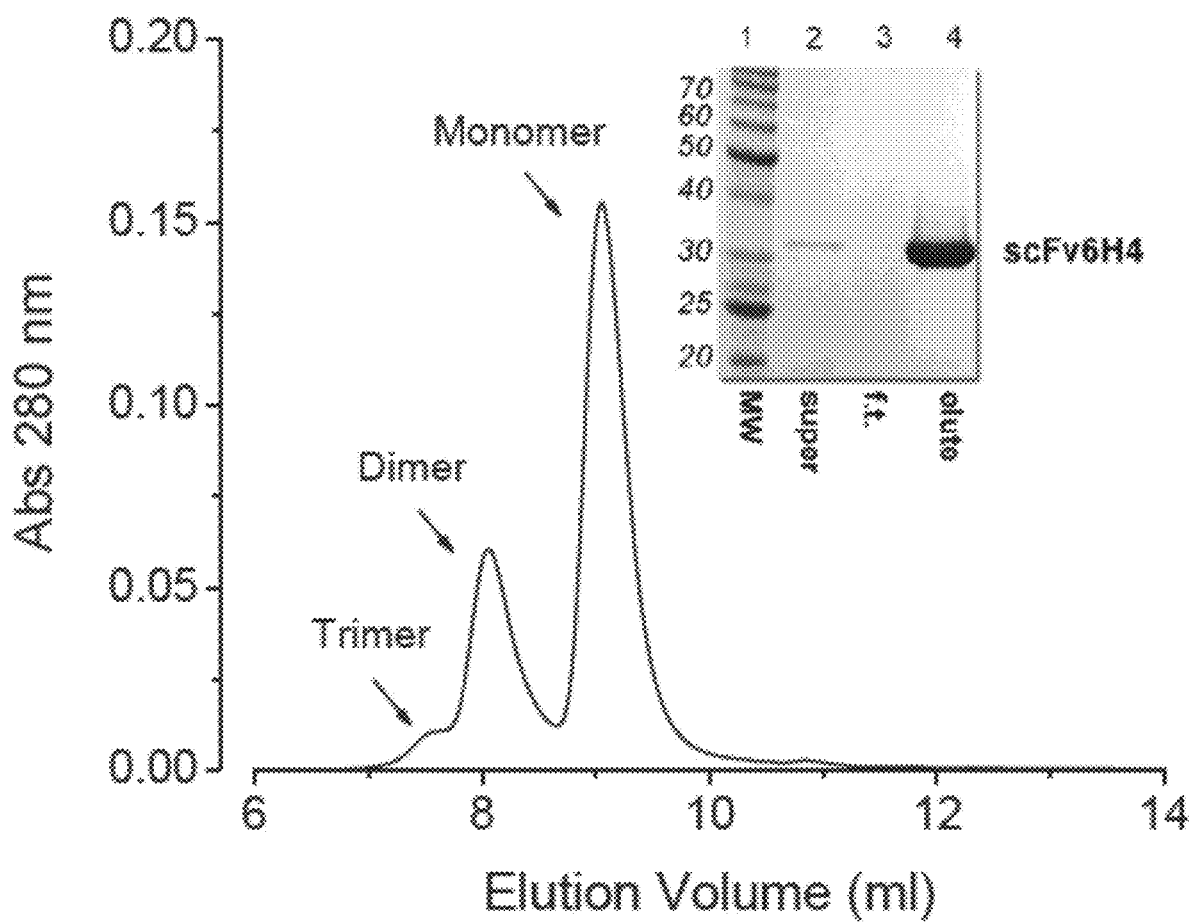

ScFv6H4 was constructed by joining the light and heavy chain variable domains of the parent mAb6H4 with a 15 amino acid linker (FIG. 9A). The genetic re-engineering of mAb6H4 IgG into scFv6H4 changed the protein from a ~150 kDa protein with two METH binding sites to a ~27.4 kDa protein with one METH binding site. It also converted the original IgG from a two gene product (form heavy and light chain coding sequences) into a single gene product. Linkers shorter than 12 amino acids can result in multimeric complexes (diabody, triabody, etc.) due to domain swapping, and transition between monovalent and divalent scFv can be controlled by linker length. While the intent was to design a predominately monomeric scFv, the purified and formulated scFv6H4 was a mixture of monomer (~75%) and dimmer (~25%), with traces of a possible trimer (FIG. 9B).

Example 9

Expression of scFv6H4

The scFv6H4 was initially expressed in *E. coli*, but during purification it was found to form >90% insoluble inclusion bodies. To circumvent this problem, the scFv6H4 coding sequence was re-cloned into a yeast expression system so that the coding sequence was in-frame behind a cleavable alpha-mating factor. This allowed protein secretion into the media during methanol-induced protein expression, thereby decreasing the potential for formation of insoluble protein inclusion bodies. The scFv6H4 yield after a 98 hr yeast fermentation production run and purification was approximately 12.4 mg/L.

Example 10

Purification of scFv6H4

The combination of a single gene-derived protein product, a media-secreted protein and an affinity tag on the protein allowed the purification of scFv6H4 to over 98% homogeneity in one purification step (FIG. 9B). Although the SDS-PAGE analysis showed a single protein band of <30 kDa, size exclusion chromatography analysis indicated that the purified and buffer-exchanged scFv6H4 product migrated as three peaks (FIG. 9B). When plotted against molecular weight protein standards, the apparent molecular weights for the monomer and dimer were 34 and 73 kDa. These estimated values were in relatively close agreement with the calculated molecular size of these two species, (monomer, 27.4 kDa; dimer, 54.8 kDa).

Example 11

Determination of $K_D$ Values for METH

Figure 10:
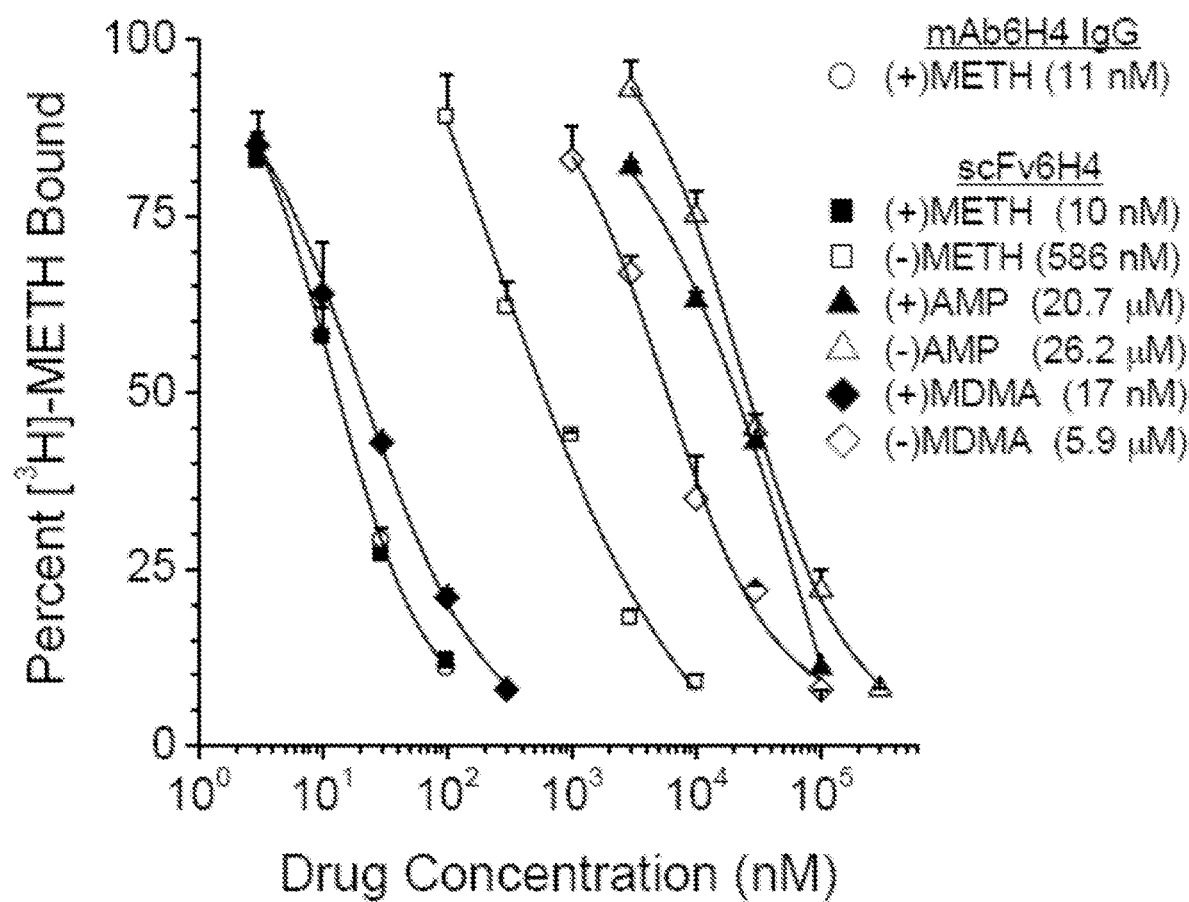
FIG. 10 graphically illustrates that scFv6H4 binds to METH and (+/−) isomers of METH-like compounds with the same affinity and specificity as the parent IgG.

To determine the IC50 values and specificity of the purified scFv6H4 for METH-like analogs, we used a bead-based radioimmunoassay (RIA). The RIA procedure utilized a His6 affinity tag at the carboxy-terminus of the VL region of scFv6H4. Binding an affinity bead to this His6 region orients the scFv6H4 METH binding site distal to the bead, allowing sterically unhindered access to METH and helping to stabilize the protein. This bead-based assay allows for the rapid separation of bound and free [$^3$H]-METH by centrifugation and excellent signal-to-noise ratios for the measurement of [$^3$H]-METH binding. The results of ligand binding characterization showed the apparent $K_D$ for METH (10 nM) was nearly identical to that previously determined for the parent IgG mAb6H4 (11 nM; Byrnes-Blake et al., 2003). The scFv6H4 also retained the same stereo-specificity as the parent IgG mAb6H4 for (+)-isomers of METH-like compounds, most importantly amphetamine, or AMP (FIG. 10). Thus, one anti-METH scFv has been developed that has potential clinical utility for the treatment of medical problems caused by METH.

Example 12

Serum Pharmacokinetics of METH with and without scFv6H4

Figure 11A:
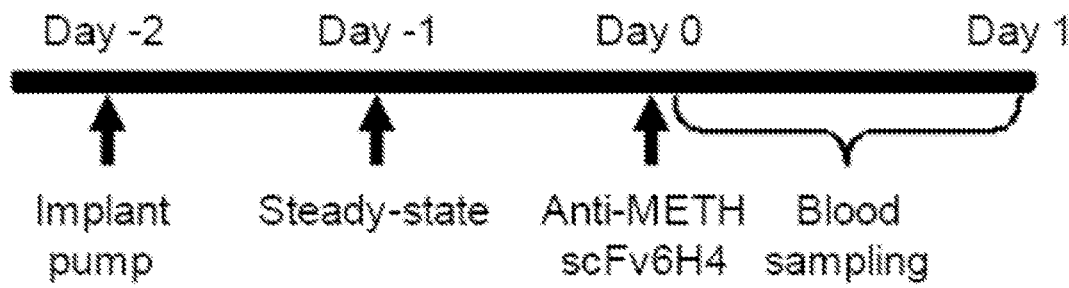
FIG. 11A and FIG. 11B depict that scFv6H4 significantly increases serum METH concentrations in vivo.
Figure 11B:
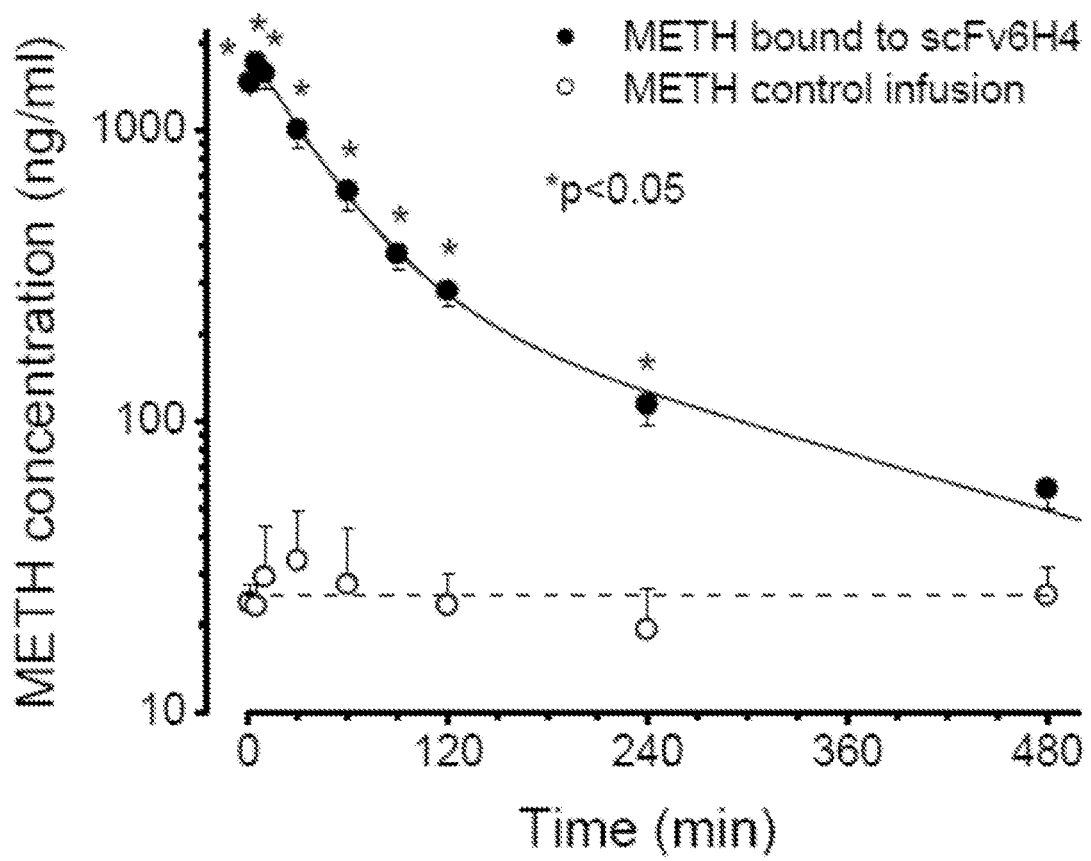

To determine the ability of anti-METH scFv6H4 to alter serum concentrations of METH, subcutaneous osmotic mini pumps were implanted to deliver METH at 3.2 mg/kg/day (FIG. 11A), which resulted in an average steady-state serum METH concentration of 25 ng/ml after 24 hrs (FIG. 11B). Administration of anti-METH scFv6H4 intravenously led to dramatic changes in serum METH concentrations. The serum METH concentration after scFv6H4 administration was significantly greater than vehicle treated controls from 1-240 min (P<0.05). The area under the METH serum concentration vs. time curve (AUC) from 1-480 min ($AUC_1^{480}$) increased from 11,120 ng*min*ml in vehicle treated controls (without scFv6H4) to 133,144 ng*min*ml for the scFv6H4 treated animals. It was calculated that a dosing regimen of 3.2 mg/kg/day of METH equates to a METH body burden of 0.2 mg/kg at steady-state. On day 2 after steady-state METH concentration was achieved, a single bolus dose of scFv6H4 (36.5 mg/kg) was administered that was equimolar in binding sites to the steady-state METH body burden. By comparison, this dose was one third of the dose of IgG (102 mg/kg) that would be needed to achieve the same number of METH antibody binding sites. Thus, use of scFv allowed a significantly lower protein load for the equivalent number of METH binding sites. Importantly, a single dose of scFv6H4 was administered, but the METH infusion continued to replace the drug at the rate of 50% of the body burden per hour based on a 1 hr METH $t_{1/2z}$.

Since METH was infused to steady-state before scFv6H4 was administered, METH was already equilibrated in tissues. Nevertheless, the scFv6H4 quickly bound METH in serum and caused a statistically significant redistribution of the drug for at least 6 hrs (FIG. 11B). Indeed, METH serum concentrations increased 65-fold within 1 min, and the METH $AUC_1^{480}$ increased 13-fold, compared to the control group. When METH concentrations in the presence of scFv6H4 (FIG. 12, solid circles) and total scFv6H4 protein concentrations (FIG. 12, open squares) were plotted as their respective molar concentrations, the relationship was nearly one-to-one. The nearly 1:1 ratio of scFv6H4 and METH concentration in the presence of scFv6H4 over time (FIG. 12) indicated that the scFv6H4 protein was responsible for the dramatic increases in METH concentrations during the 8 hr study.

Example 13

Determination of Pharmacokinetics of Monovalent and Multivalent Forms of scFv6H4

Figure 12:
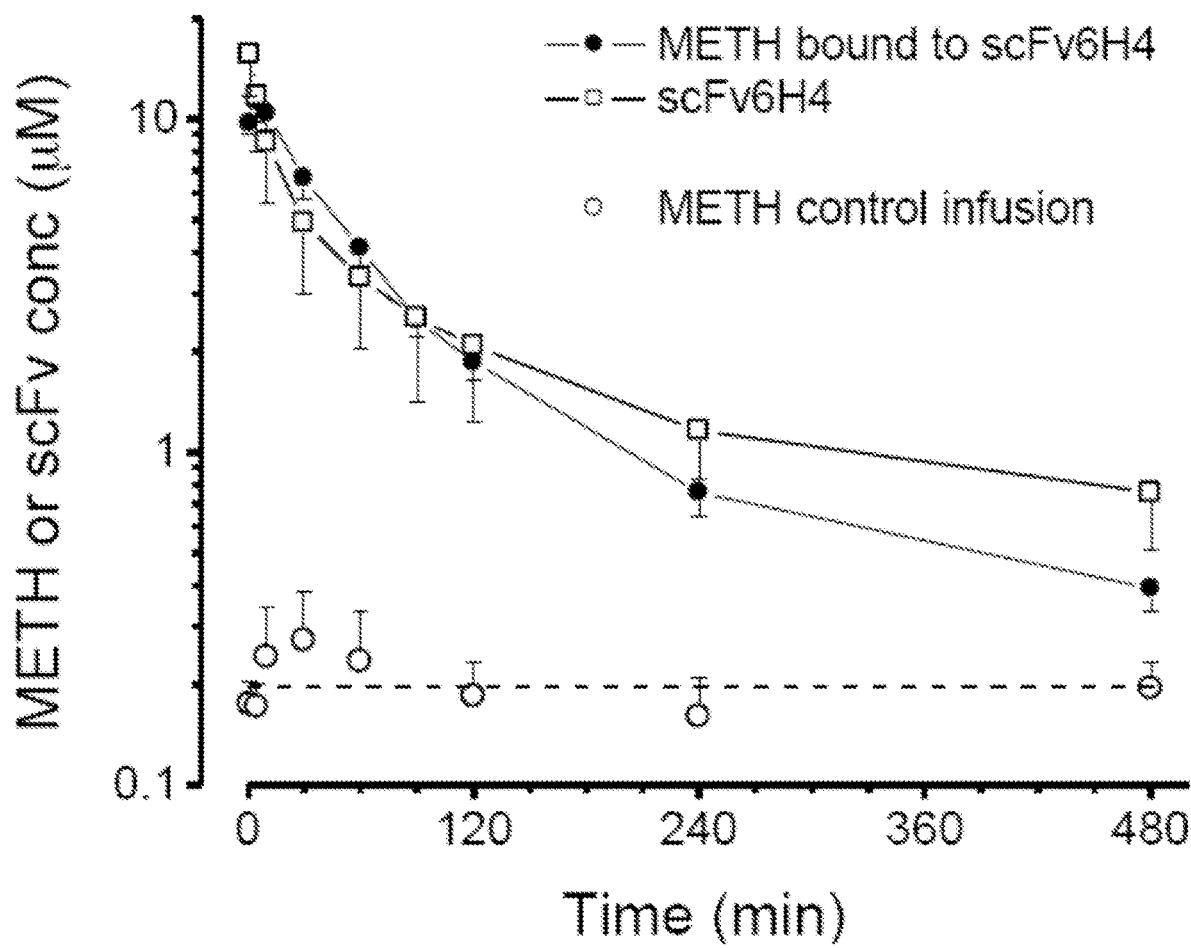
FIG. 12 depicts METH concentrations in the presence of scFv6H4 (closed circles), scFv6H4 protein concentrations (monomer and other multivalent forms), and METH steady-state concentration without scFv6H4. All concentration values are shown as µM concentrations versus time.

Since FIG. 9 indicates that the native scFv6H4 was administered as a mixture of monomer (75%) and dimer (25%), the pharmacokinetic profile of the scFv6H4 monomeric (alone) and other multivalent forms (as a composite) were assessed. Fractionation of the serum samples from each time point showed that the monomer was almost completely eliminated from the serum in <30 min, but the divalent and other apparently multivalent larger proteins persisted for >240 min (FIGS. 11, 12, and 13). Due to the complexity of these multivalent changes, the pharmacokinetic values for the monomer were calculated individually, and the pharmacokinetic values of the multimers (i.e. dimer, and trimer) were calculated together. Based on the analysis of the terminal elimination data in FIG. 12, the overall $t_{1/2\lambda z}$ of multivalent scFv6H4 forms was 228±38 min. The relative concentrations of scFv6H4 monomer and dimer were calculated and plotted against the time of collection (FIGS. 12 and 13). Concentrations of [$^3$H]-scFv6H4 in the SEC fractions eluting after the monomer peak (at ~9 min) were thought to be small molecular weight degradation products that did not contribute to METH binding, thus, they were not considered further.

Figure 13A:
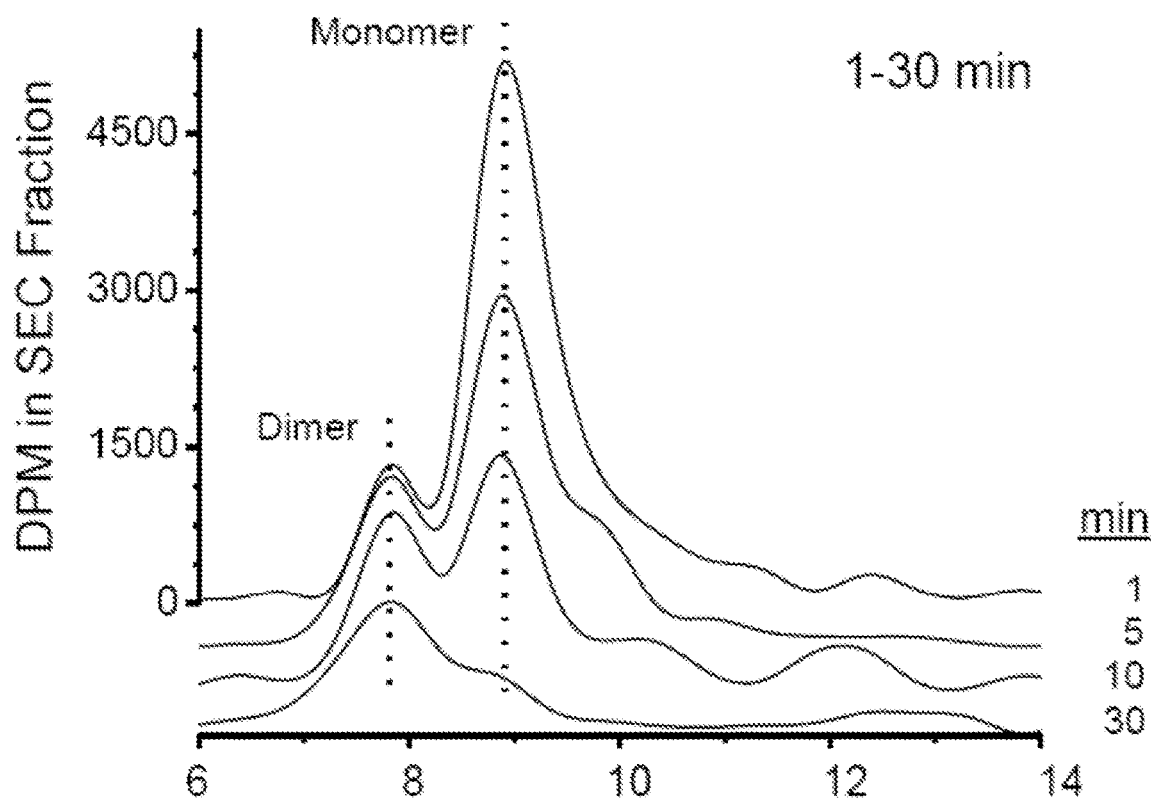
FIG. 13A and FIG. 13B graphically illustrate plots of scFv6H4 concentrations in rat serum vs. time after an intravenous bolus dose of anti-METH scFv6H4 (37 mg/kg) along with a tracer dose of anti-METH [$^3$H]-scFv6H4 (1×10$^6$ dpm).
Figure 13B:
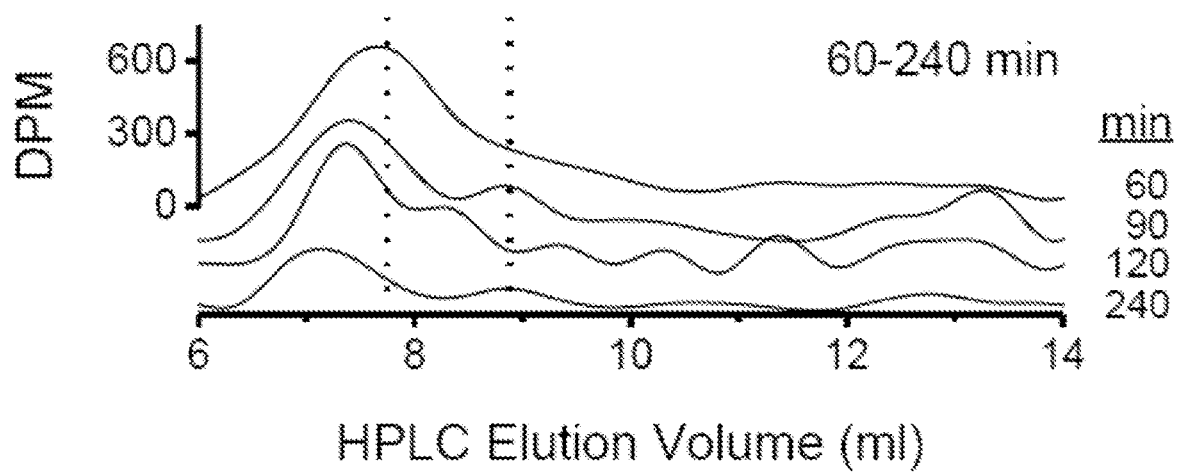
Figure 14:
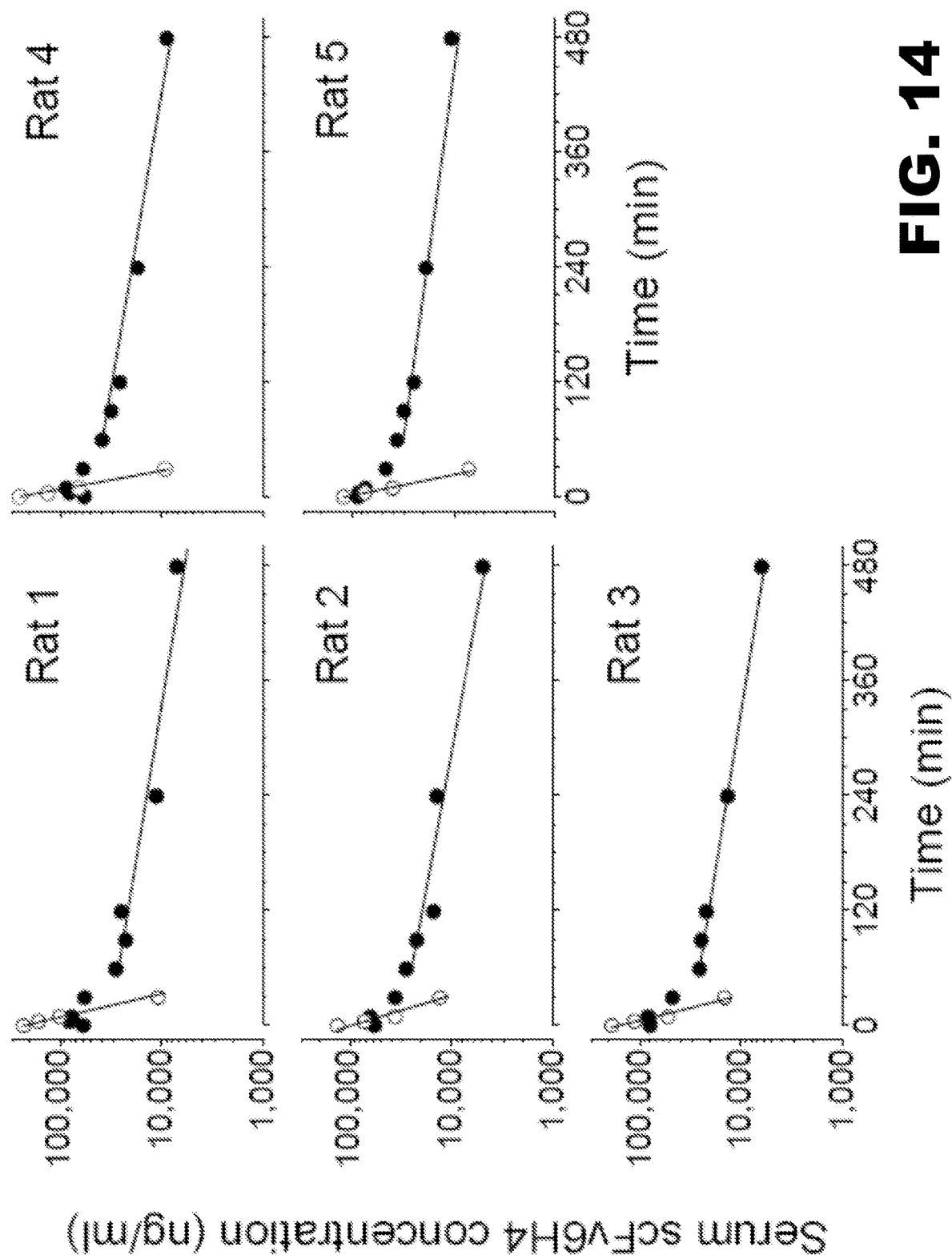
FIG. 14 depicts individual plots of scFv6H4 concentrations in rat serum vs. time after an intravenous bolus does of anti-METH scFv6H4 (37 mg/kg) along with a tracer dose of anti-METH [$^3$H]-scFv6H4 (1×10$^6$ dpm). After analysis of scFv6H4 by SEC, dpm peak heights of monomeric (open circles) and multimeric (closed circles) were plotted.

For the monomer form of the scFv6H4, the concentration in the first four time points (1, 5, 10, and 30 min) could only be determined, because after 30 min the concentration of the [$^3$H]-scFv6H4 was too low to accurately measure (FIG. 13A). These data indicated the monomer had a $t_{1/2\lambda z}$ of 5.8±0.8 min (See, Table 2 for complete PCKN parameters). The multimeric forms of scFv6H4 exhibited a much longer serum kinetic profile. Interestingly, in four of the five rats, the concentrations of the divalent form did not rapidly decrease in the first 10 min (FIG. 14, Rats 1-4). After 30 min, the multivalent scFv6H4 concentrations appeared to more rapidly decrease and exhibited an apparent biphasic curve. The biphasic shape of this curve was likely due to changes in scFv6H4 distribution and elimination, and formation of new scFv6H4 multimers.

Since both the monovalent (27.4 kDa) and divalent (54.8 kDa) scFv6H4 are below or near the molecular weight cut-off point of ~50 kDa for glomerular filtration, a fairly rapid clearance of both proteins was expected. Unexpectedly, there was an apparent time-dependent clearance of monovalent scFv6H4, and a progressive formation and clearance of other multivalent forms of scFv6H4 (FIGS. 12 and 13). Early changes in the monovalent form of scFv6H4 suggested the $t_{1/2\lambda z}$ for the monomer was only 5.5 min (See, FIGS. 12 and 13 for time-lapsed comparisons and Table 2 for volume and clearance). These time-dependent changes in scFv6H4 indicated the clearance (See, Cls, Table 2) of monomeric scFv6H4 resulted from a combination of loss and in vivo conversion to dimers and other multivalent forms of scFv6H4. These pharmacokinetic findings are extremely novel and are the most complete pharmacokinetic studies for any scFv.

TABLE 2

Serum PCKN Parameters of scFv6H4.

| ScFv6H4 Form | $\lambda_z$ (min$^{-1}$) | $t_{1/2\lambda z}$ (min) | $V_{ss}$ (ml/kg) | Cls (ml/min/kg) |
|---|---|---|---|---|
| Monovalent | 0.07 | 5.8 | 780 | 9.4 |
| S.D. | 0.02 | 0.8 | 234 | 2.8 |
| CV, % | 22.9 | 13.7 | 30 | 29.6 |
| Multivalent | 0.0031 | 228 | 246 | 1.1 |
| S.D. | 0.0004 | 38 | 22 | 0.2 |
| CV, % | 14.1 | 16.8 | 9.6 | 21.0 |

In vitro dimer formation is common in scFv proteins, and relative amounts of dimer and monomer can vary depending on linker length, pH, ionic strength, and presence or absence of antigen. Based on structural evidence, there are two major conformations that scFv dimers can adopt. The first conformation is the result of domain interactions between the VL of one scFv to the VH of another. After the protein folded, this conformation requires the "opening" of the scFv molecule around the linker and binding to another unhinged scFv, with an intermediate that is unable to bind to antigen. The other conformation that scFv dimers can adopt is a "back-to-back" conformation. Since the constant regions of the intact IgG that are normally adjacent to the variable region are absent in scFv, these regions are free to form other protein-protein interactions. Since transition from monomer to dimer does not require intra-VH and VL domains to dissociate, these dimers can theoretically associate and dissociate without perturbing the antigen binding site. scFv6H4 possesses the linker sequence and framework residues that favor back-to-back dimer formation, specifically Pro-L40 and Gly-L41 in the VL domain, and Pro-H41 and Gly-H42 in the VH domain. In light of these structural features, the rapid transition from monomer to dimer and other multivalent scFv forms in vivo, along with no apparent loss of binding to METH (FIG. 11), scFv6H4 likely forms a back-to-back dimer configuration. Because of this unpredictable multimerization, manipulation of the scFv solely through molecular engineering (e.g., linker alteration or linking two or more scFv by molecular techniques) does not usually produce reliable products.

These studies show the design, expression, purification, and preclinical characterization of a high affinity therapeutic scFv against METH. The scFv6H4 was pharmacologically active for an extended period of time in vivo and was able to significantly redistribute METH into serum for at least 4 hrs. Pharmacokinetic data indicated that the multivalent forms of scFv6H4 were primarily responsible for the longer-term METH binding in serum, although the scFv6H4 dose was primarily composed of monomer (75%).

Example 14

Structure Studies of Anti-METH scFv6H4

To more fully understand the interactions involved in antibody binding to METH, purified and concentrated scFv6H4 in the presence of METH were used to determine the crystal structure of scFv6H4 bound to METH. After preparing crystals of scFv6H4 in the presence of METH, the crystal structure of the scFv6H4/METH complex was determined by molecular replacement techniques using an earlier homology model of the scFv6H4 as the search model for the rotation and translation functions. The rotational and translational searches were carried out with 4 Å diffraction data using the CNS suite of programs (Brunger et al., 1998).

After several cycles of rebuilding and refinements the R-factor dropped to 22% and the R-free dropped to 24.5% for a final value of 1.9 Å resolution.

Example 15

A Deep Aromatic Binding Pocket Secures METH by Strong Hydrophilic Bonding

Figure 15A:
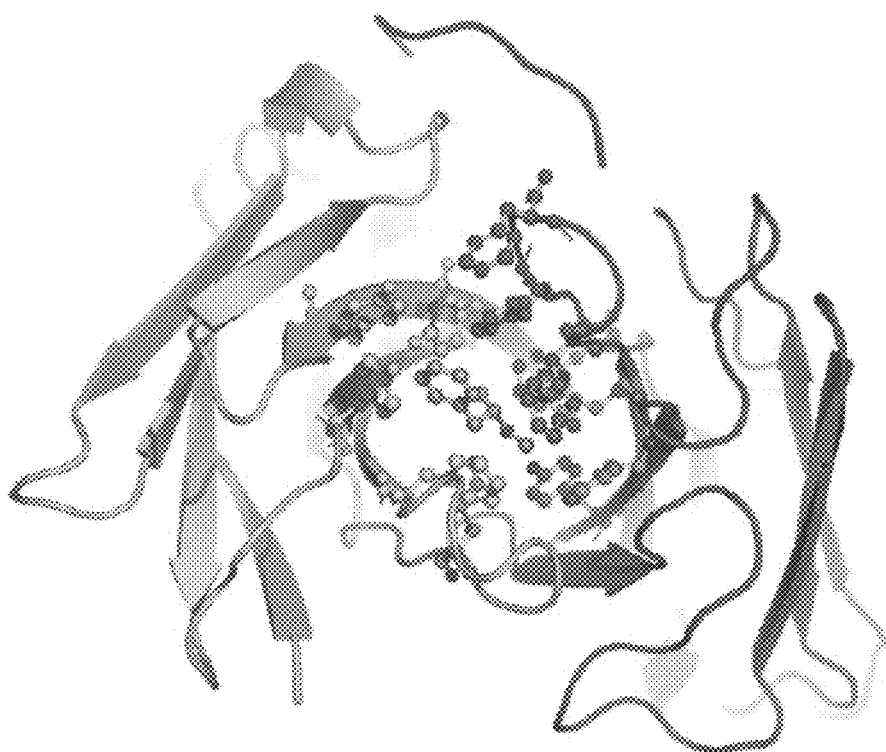
FIG. 15A and FIG. 15B depict the scFv6H4/METH complex.

Antibodies interact with antigens through the CDR loops on the antigen binding site of the antibody molecules. The binding sites for larger molecules, such as a protein, are usually a surface or a shallow crevice on the surface of the variable domains formed by the CDR loops of both heavy and light chains. In the present case, however, the METH moiety binds deeper in between the light and heavy chain variable domains (FIG. 15). It was found that scFv6H4 binds METH deeply in an aromatic pocket formed by several residues from both domains. Interestingly, some of the side chains for the formation of the pocket are contributed by the β-strands of the framework residues. The side chains forming the pocket are: LC-34Y, LC-36Y, LC-89H, LC-91W, LC-94F, LC-96F and LC-99F from the light chain and HC-33Y, HC-47Y, HC-50Y, HC-95F from the heavy chain. HC-33Y and HC-95F side chains are positioned on the upper side or "over" the aromatic ring of METH. HC-50Y is positioned to the side. The residues from the light chain form most of the lower portion of the pocket (FIG. 15A).

Figure 15B:
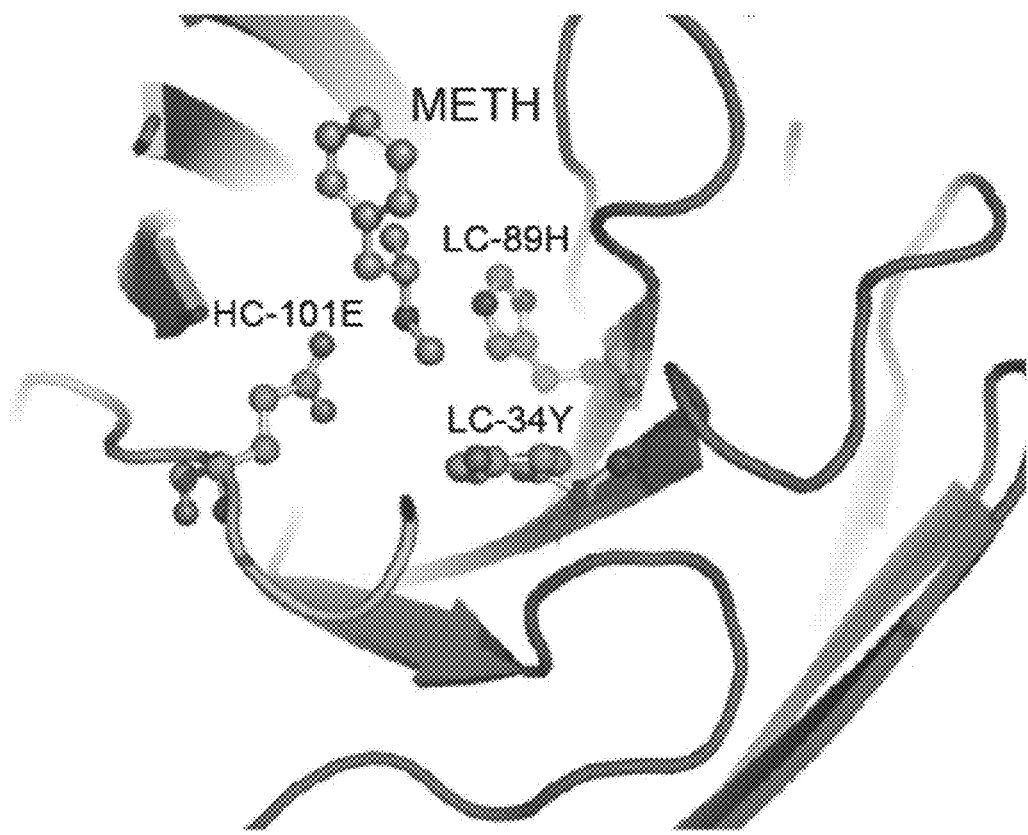

The secondary amine of METH plays a crucial role in binding by contributing to hydrogen bonding interactions (FIG. 15B). There is a strong hydrogen bond, and possibly a salt bridge, between the nitrogen atom of the METH and the carboxyl oxygen of Glu 101 of the heavy chain (distance=2.6 Å). There are two additional side chains, a tyrosine and a histidine, in the vicinity of the nitrogen of METH which contain hydrophilic groups. It is possible that the amide nitrogen is involved in some weaker interactions with these residues.

Example 16

Hapten Design has Produced Anti-METH mAb with Improved Specificity and Functionality A large collection of function and sequence data was analyzed and revealed important IgG sequence and structural features that are involved in antibody-METH interactions. In particular, key hapten features that are important for shaping necessary molecular interactions during immunization were found. The systematic design of METH-like haptens has generated a panel of antibodies that have varied affinity, specificity, and duration of action. Because the chemical composition and molecular orientation of the drug-like hapten on the antigen are crucial determinants in generating antibodies against small molecules, the goal of these long-term studies was to discover design criteria needed to produce long-acting anti-METH and anti-AMP mAb medications. This led to discovery of mAb medications with structural attributes needed to treat both overdose and addiction indications resulting from METH and AMP abuse. Although high affinity for METH was a foremost goal, it was a goal to eventually generate a single mAb with high affinity for the metabolite (+)AMP and a related compound, (+)MDMA ((+)-3,4-methylenedioxymethamphetamine, which is the (+)-isomer in the racemic mixture known as MDMA or ecstasy). Because antibodies generated against hapten-protein conjugates react to the portion of the hapten that is distal to the point of chemical attachment to the protein, molecular orientation of the hapten on the protein carrier is critical to control antibody specificity. Additionally, (+)-isomers of METH-like compounds are known to produce significantly more psychomimetic effects, locomotor activity, stereotyped behavior, monoamine oxidase inhibition, and addiction liability than (−)-isomers. After considering these immunological and pharmacological factors, prototype (+)METH-like haptens were synthesized to mimic molecular properties of (+)-isomers of the drugs, without significant cross-reactivity to (−)-isomers.

TABLE 3

Chemical Structure of Haptens, the Resulting mAb, and $K_D$ Values for Key Drugs.

| | | mAb Name | Key Psychostimulants | | |
| --- | --- | --- | --- | --- | --- |
| Hapten Structure | Hapten Name | (Isotype and light chain) | (+)METH $K_D$ (nM) | (+)AMP $K_D$ (nM) | (+)MDMA $K_D$ (nM) |
| [structure] | (+)METH P4 | mAb6H8 (IgG$_{1\kappa}$) | 250 | 41,000 | 106 |
| [structure] | (+)METH P6 | mAb6H4 (IgG$_{1\kappa}$) | 11 | 4000 | 4 |
| [structure] | (+)METH PO6 | mAb6H7 (IgG$_{2b\kappa}$) | 95 | 47,000 | 87 |

TABLE 3-continued

Chemical Structure of Haptens, the Resulting mAb, and $K_D$ Values for Key Drugs.

| Hapten Structure | Hapten Name | mAb Name (Isotype and light chain) | Key Psychostimulants | | |
|---|---|---|---|---|---|
| | | | (+)METH $K_D$ (nM) | (+)AMP $K_D$ (nM) | (+)MDMA $K_D$ (nM) |
| [structure] | (+)METH MO6 | mAb9B11 (IgG$_{1}$ $_\lambda$) | 41 | 5000 | 123 |
| [structure] | (+)METH MO10 | mAb4G9 (IgG$_{2b}$ $_\kappa$) | 34 | 120 (51 nM with [$^3$H]-(+)AMP) | 140 |

With the above criteria in mind, two haptens were generated with systematic changes in linker length (P4 and P6, Table 3) and one with an oxygen, all attached to the para-carbon of the phenyl ring of METH (P06). An oxygen was also attached to the phenyl ring structure in two additional haptens, MO6 and MO10, but the linkers were attached to a meta-carbon of the phenyl ring of (+)METH. This strategy was designed to present the oxygen of the (+)MDMA-like structure along the same spatial plane as the (+)METH molecule's chiral center. The longer (+)METH MO10 spacer was used to allow more flexibility in the hapten on the protein to discover mAb(s) with broader recognition of (+)METH-like structures.

From immunizations with these haptens, several classes of antibodies with different efficacies have been generated. The duration of action and function of anti-(+)METH mAbs in vivo was decreased compared to predictions based on known mAb pharmacokinetics, which was unanticipated. The first generation of haptens (e.g., (+)METH P6 and (+)METH P4) were purposely designed to produce mAbs specific for (+)METH, with virtually no cross reactivity with (+)AMP. With the second generation of haptens, having specificity for (+)METH and (+)AMP with (+)METH MO10, it was discovered that the resulting mAb (mAb4G9) had the other advantages of increased duration of action and efficacy. MAb4G9 has also shown the longest duration of in vivo function of any of the mAbs. This is related to important chemical properties of the MO10 hapten. Thus, studies will begin with anti-METH scFv4G9 and other scFv generated from the MO10 class of antibodies.

Example 17

Figure 16:
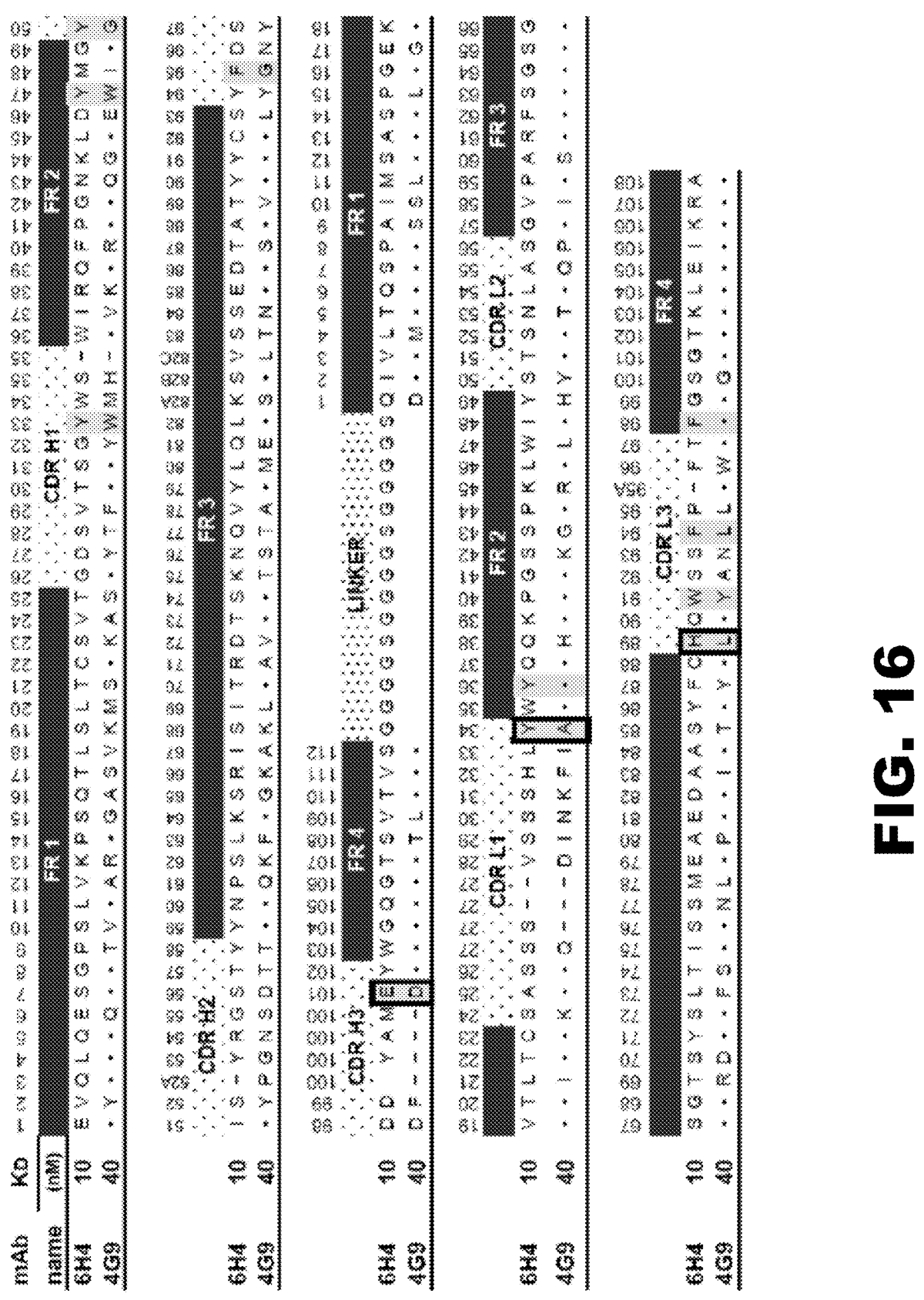

Comparison of Primary Amino Acid Sequences of mAb6H4 and mAb4G9 Based on Structural Data To determine the mechanism of binding between METH and scFv4G9 a sequence alignment of the primary sequences of the two antibodies was performed (FIG. 16). Both of these antibodies bind to METH with similar affinity (Table 3), but have very different affinities for AMP. From the alignment, it appears that although there is some similarity between the two antibodies, the differences far outweigh the similarities. For instance, when just the residues in the binding pocket are compared (FIG. 16, yellow highlight), only two residues share full identity, LC-36Y and LC-98F. The remaining residues share no identity and are not very similar in chemical properties, indicating that anti-METH mAb4G9 (and thus, scFv4G9) possesses a very different binding pocket than scFv6H4. This is not surprising since the two antibodies were generated with very different haptens (Table 3).

There is an additional important difference between the two antibody sequences that might explain data that indicates certain classes of our antibodies show inactivation over time in vivo. The crystal structure of scFv6H4 shows that the histidine at position LC-89 is important for interaction with the nitrogen of METH. The FcRn is responsible for the long half-life of IgG by interacting with the protein in a pH-dependent manner. Two key histidine side chains (pKa=6.0) of FcRn are titrated to a different protonation state in the lower pH environment of the endosome (pH<6.5), allowing them to interact with IgG. This pH change can also affect histidine side chains of IgG. If these residues are key to antigen binding (e.g., LC-89H of scFv6H4), affinity could be altered. By comparison, the sequence of mAb4G9 lacks histidine residues in key CDR positions and also does not lose function over time.

Example 18

Preliminary Dendrimer Conjugation to Anti-METH mAb

To test the crosslinking strategy and analytical and purification methods (Le., SDS-PAGE, FPLC, MS/MS), a preliminary experiment using a generation 3 PAMAM dendrimer and a high affinity anti METH IgG, mAb4G9 were performed. The IgG form of the antibody, instead of the scFv, was used due to the availability of the IgG over the scFv and the interest in defining the chemistry and analytical techniques. Briefly described, the common crosslinker 1-ethyl-3-[3-dimethylaminopropyl]carbodiimide hydrochloride (EDC), a zero-length crosslinking agent, was utilized. In this reaction scheme, the carboxyl group of the dendrimer was first activated by exchanging 19.65 mg of PAMAM G3 dendrimer into activation buffer (0.1 M MES, 0.5 M NaCl, pH 6.0) using a PD-10 desalting column (GE Healthcare). After pooling fractions, EDC was added to a concentration of 2 mM and then sulfo-N-hydroxysuccinimide (Sulfo-NHS) was added to 5 mM, stabilizing the amine-reactive intermediate by converting it to an amine-reactive Sulfo-NHS ester. This step increases the efficiency of EDC-mediated coupling reactions. The addition of NHS is also important because it allows a two step crosslinking procedure, keeping the side chain carboxyl groups of the protein intact by only reacting with the terminal amines. After the dendrimer activation and desalting into administration buffer (0.5 M NaPO4, 0.15 M NaCl, pH 7.4), 18 mg of the mAb in a dendrimer:mAb molar ratio of 1:100 was added to determine if more than one mAb could be conjugated to the dendrimer. The dendrimer selected for the experiment possessed 32 COOH terminal groups, allowing several IgG to couple to the dendrimer at once. After crosslinking, the reaction was analyzed by SDS-PAGE and size exclusion chromatography. The ability to analyze dendrimers by common protein analysis and detection techniques (SDS-PAGE and coomassie staining) greatly facilitates characterization. Additionally, dendrimers have a high molar absorptivity at 254 nm, a common wavelength used for detection during column chromatography.

Example 19

Evaluation of Detection and Analysis Techniques of Dendrimer Conjugation

Figure 17A:
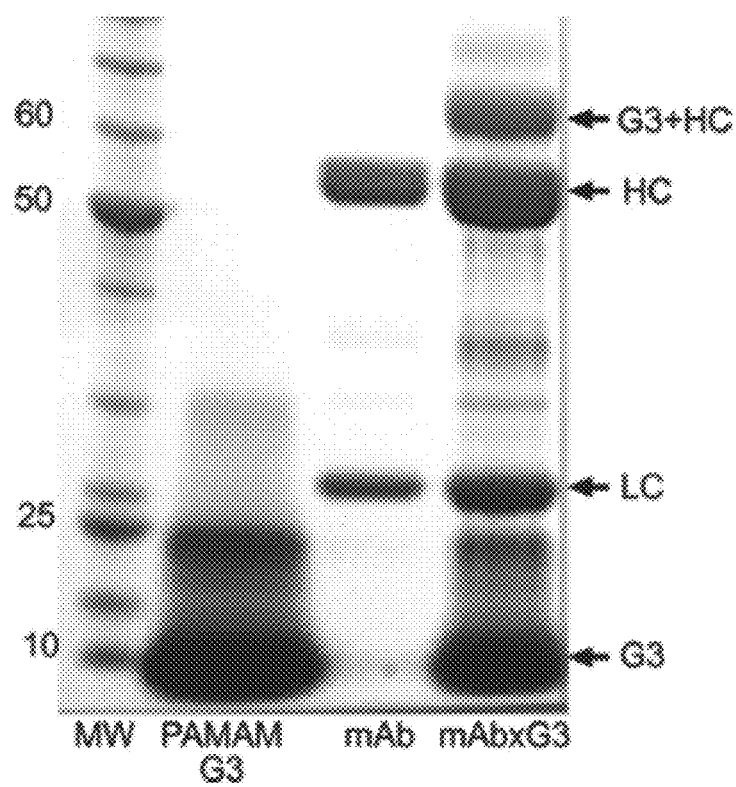
FIG. 17A and FIG. 17B depict crosslinking PAMAM G3 dendrimer to anti-METH mAb4G9.
Figure 17B:
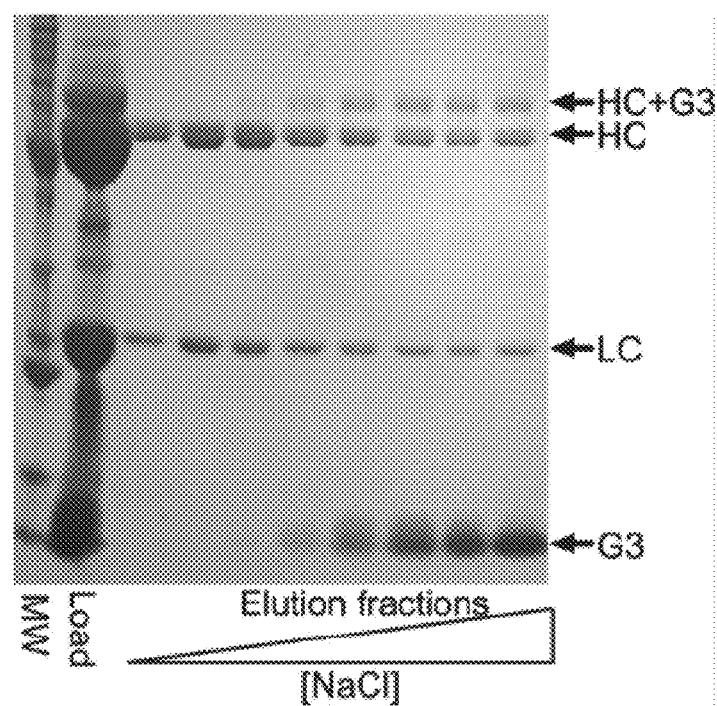

From the preliminary crosslinking experiment in Example 16, it was found that after the crosslinking reaction no change was seen in the size of the band corresponding to the light chain (LC) of the IgG (FIG. 17). However, a new band appeared in the 60 kDa molecular weight range. This band corresponds to the molecular weight of the G3 dendrimer conjugated to the heavy chain (HC) of the IgG. When analyzed by size exclusion chromatography, a small additional peak was observed, ~10 kDa larger than the intact IgG, supporting this theory. Interestingly, no larger molecular weight species were observed in the size exclusion chromatogram, indicating that the dendrimer preferentially cross-linked to only one heavy chain at a time.

Example 20

Evaluation of Chromatographic Separation Techniques of Dendrimer Conjugations

An initial purification of the IgG-dendrimer reaction was performed to determine the ability to perform standard chromatographic techniques with the dendrimer and conjugates. A 2 ml aliquot of the reaction mixture was loaded onto a 1 ml Q-sepharose column (GE Healthcare, Piscataway, N.J.). After washing, it was eluted with a 20 column volume gradient from 0.1 M to 1.0 M NaCl. In one chromatographic step, most of the unbound IgG was separated from the dendrimer utilizing the negative charge of the dendrimer to preferentially adhere to the column over the IgG. Also, the dendrimer dimer that was observed in the unconjugated sample was missing after the conjugation reaction. Due to the size differences in the IgG and dendrimer, a simple size exclusion chromatography step following the Q-sepharose should separate the unbound dendrimer from the IgG-dendrimer conjugate. The results of the above preliminary IgG crosslinking experiment demonstrate the ability to crosslink the dendrimer to a protein.

Example 21

Producing High Affinity Anti-METH Antibody Fragments

Small fragments based on existing anti-METH mAbs with favorable in vivo and in vitro METH-binding properties will be designed and produced. The anti-METH mAbs will be converted to a smaller fragment by combining the variable binding regions of the heavy and light chains with a linker to make a single gene. By converting to a single gene product, the antibody can be produced more easily since there is no concern about producing the correct stoichiometry of two gene products (heavy and light chains). Additionally, the dose of protein that will be delivered is less with the fragment, since the protein has been reduced from a 75 kDa protein (one-half of a 150 kDa IgG) to a 27 kDa protein for delivery of the same number of binding sites. An scFv from the variable domain sequences of anti-METH/AMP mAb4G9 will be cloned. The mAb4G9 antibody exhibits a dual specificity to both METH and AMP, and mAb4G9 exhibits significantly longer activity than any antibody known in the art.

Figure 18A:
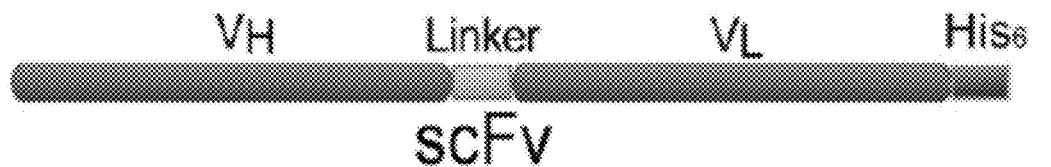
FIG. 18A and FIG. 18B depict the design schematic of two scFv prototypes including (FIG. 18A) scFv4G9 and (FIG. 18B) scFv4G9-C. (Key: VH, variable heavy region; VL, variable light region; Linker, 18 amino acid linker (GGGGPGGGGSGGPGGGGS; SEQ ID NO:1); His$_6$, 6-histidine tag for purification; and, Cys, engineered cysteine residue for site-specific conjugation). The PPL signal sequence is not shown since it will be cleaved during secretion and is not part of the mature protein.
Figure 18B:
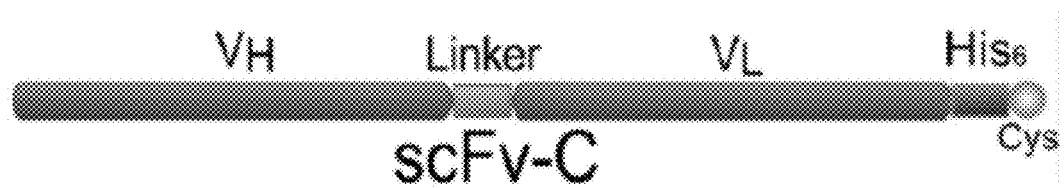

The general scFv4G9 cloning scheme includes joining the variable domain sequences of mAb4G9 with an 18 amino acid linker. This VH-linker-VL sequence will be the basis of the constructs used for expression of the scFv4G9. Two approaches to the design of the expression constructs will be taken (FIG. 18). Both designs will share the following cloning scheme. The scFv4G9 cDNA sequence will be amplified with primers that will introduce a Kozak sequence for translation initiation and a bovine preprolactin (PPL) signal sequence to the N-terminus of the protein for efficient secretion from cells. This signal sequence is an efficient sequence for targeting cells through the secretory pathway, which is important since the main advantage of using a eukaryotic expression system over a prokaryotic system is the quality control and protein folding that occurs as a protein passes through the secretory pathway. A $His_6$ tag will be added to the C-terminus for efficient purification by metal affinity chromatography.

The second design scheme will include the above cloning features plus adding an additional cysteine at the C-terminus of the scFv4G9 sequence following the His6 tag. Introduction of this cysteine will create a controllable synthetic attachment site for dendrimers. After sequencing the cDNA, the scFv4G9 sequences will be transfected into CHO cells via viral transduction. Expression media containing the expressed scFv4G9 will be analyzed by bead-based RIA for confirmation of retained original affinity and specificity. ScFv4G9 will be produced by expression in two 20 L batches to generate two 20 gram vials of protein. The scFv4G9 will be purified by metal affinity chromatography, utilizing the engineered His6 tag on the C-terminus of the protein.

Example 22

Figure 19:
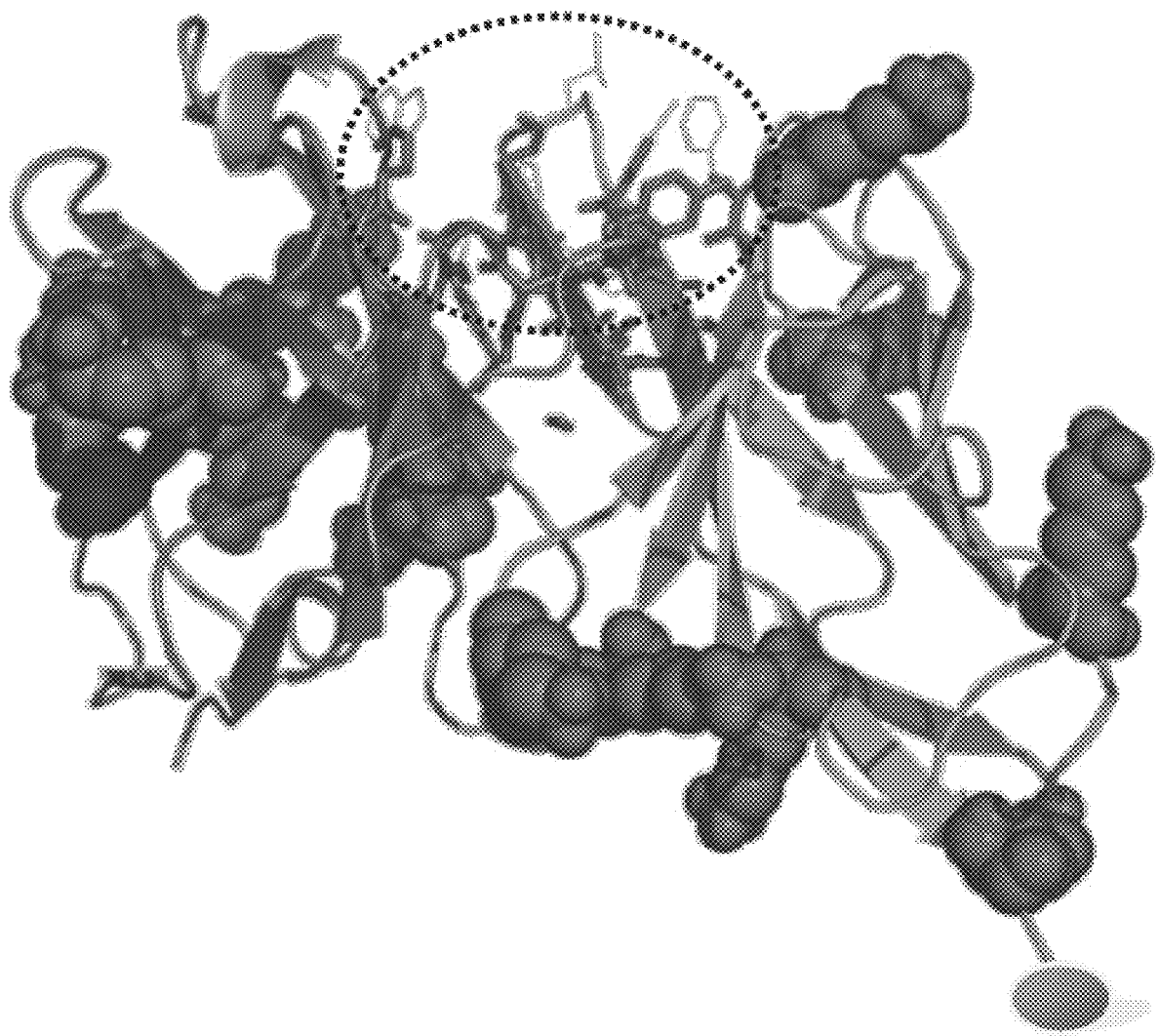
FIG. 19 depicts an in silico model of scFv4G9. The variable heavy chain is on the left (blue) and variable light chain is on the right (green). Lysine side chains are shown as red spheres for emphasis. The binding site of METH is circled. The location of the proposed cysteine is an orange oval to the bottom right of the figure.

Generate and Characterize Anti-METH scFv Dendrimer Delivery Systems (Dendribodies) for In Vivo Pharmacological Testing Based on the crystal structure of anti-METH scFv6H4 and in silico structural modeling of scFv4G9 (FIG. 19), there are 8-10 lysine residues available for crosslinking, all of which are positioned at structural sites away from the METH binding site. However, since METH is such a small molecule (~150 Da), it is not anticipated that steric interference will be a problem, even if the dendrimer is conjugated to a lysine proximal to the binding site. For lysine-specific conjugation, a G3 PAMAM dendrimer with succinamic acid terminal groups will be conjugated to the scFv as described herein. The optimal scFv4G9:dendrimer ratio to achieve the highest yield of multimeric dendribody will be determined as described herein.

The G3 PAMAM dendrimer succinamic acid terminal groups will be activated using EDC/Sulfo-NHS. scFv4G9 will be added to the reaction in scFv4G9:dendrimer binding site stoichiometric ratios of 1:1, 1:3, and 1:10. The reaction will be monitored for incorporation over 30 min to 2 hr by SDS-PAGE and SEC. Products will be purified by ion exchange chromatography (IEC) and/or SEC. The results will be analyzed and the procedure will be repeated on a large scale. Dendribody products will be analyzed by mass spec for accurate molecular weight characterization. Dendribodies will be formulated for use in pharmacokinetic experiments.

Figure 20:
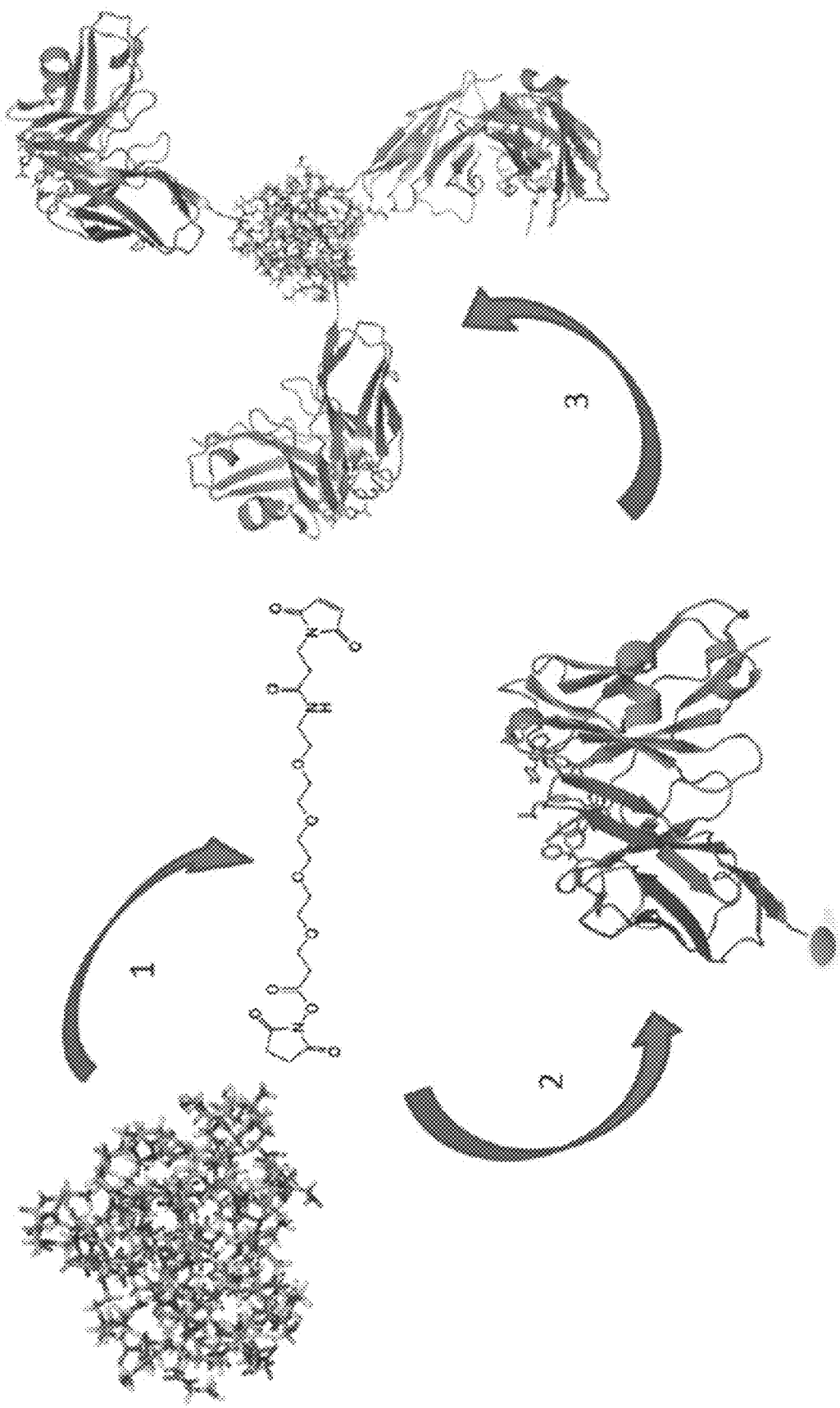
FIG. 20 depicts the experimental design scheme for site specific scFv4G9-C dendrimer conjugation. 1) PAMAM dendrimer will be conjugated to heterobifunctional PEO linker; 2) Dendrimer-linker will be conjugated to scFv4G9 creating a thiol bond; and, 3) Representation of expected product. Only three scFv4G9 molecules are shown attached to the dendrimer for clarity. However, five or more scFv4G9 molecules could couple without steric interference.

A second conjugation strategy has been designed with the potential to generate a dendribody with increased multivalency, increased solubility, and reduced risk of antigenicity. Site-specific conjugation to a cysteine will be engineered at the carboxy-terminus of the scFv4G9 protein sequence, creating scFv4G9-C. The scFv4G9-C will be conjugated to a PAMAM dendrimer with primary amine terminal groups (—NH2) utilizing a PEO (or PEG, used interchangeably) crosslinker that is reactive to free amines and reduced sulfhydryl groups (FIG. 20). The basis of the chemistry is to exploit the selective chemistry of a free cysteine. The variable regions of an IgG inherently possess four cysteines that form intrachain disulfide bonds in the variable light and heavy chains. The newly engineered scFv4G9 (scFv4G9-C) will contain an additional cysteine at the C-terminus, which due to its highly exposed nature at this position will be available for reactions with sulfhydryl-reactive crosslinkers.

This strategy was adopted for three reasons. First, site specific conjugation distal to the METH binding site will lessen the likelihood of steric interference with METH binding. Second, since the cysteine residue will be at the C-terminus of the protein, this strategy could allow more scFv4G9-C molecules to attach to the dendrimer surface (FIG. 20). Third, the PEO-based spacers that have been selected are an attractive alternative to carbon-based spacers for protein dendrimer conjugation due to the increased flexibility and solubility of the linker, the decreased change of aggregation, and reduced immunogenicity of the linker itself. The heterobifunctional PEO linker possesses an NHS ester at one end for crosslinking to terminal amines, and a maleimide group at the other for crosslinking to sulfhydryls. These linkers are commercially available in five different lengths, from 17.6 Å to 53.4 Å (Thermo Scientific, formerly Pierce Bio, Rockford, Ill.). Thus, this strategy could produce dendribodies with increased multivalency, increased solubility, and reduced risk of antigenicity.

The terminal cysteine of scFv4G9-C will be gently reduced. PEO heterobifunctional crosslinker will be conjugated to G3 PAMAM-succinamic acid dendrimer. ScFv4G9-C will be added to the reaction in scFv4G9-C: dendrimer binding site stoichiometric ratios of 1:1, 1:3, and 1:10. The reaction will be monitored for incorporation over 30 min to 2 hours by SDS-Page and SEC. Products will be purified by ion exchange chromatography (IEC) and/or SEC. The results will be analyzed and the procedure will be repeated on a large scale. Products will be analyzed by mass spec for accurate molecular weight characterization. Dendribodies will be formulated for use in pharmacokinetic experiments.

Example 23

Determine the Serum Pharmacokinetic Properties of Dendribodies and their Ability to Alter Serum Disposition of METH and its AMP Metabolite in Rats This series of studies is designed to examine the pharmacokinetic properties of unconjugated scFv4G9, dendribodies, and the effect of unconjugated scFv4G9 and dendribodies on METH and AMP pharmacokinetics. Since AMP is the major active metabolite of METH, and mAb4G9 shows AMP-binding activity as well, the ability of the dendribodies to alter the disposition of this metabolite will be measured. The serum pharmacokinetics of unconjugated scFv4G9 will be compared to up to five different dendribody conjugates in the presence of METH to determine key serum pharmacokinetic parameters (i.e. volume of distribution, clearance, AUC, and half-life).

The five dendribodies will be selected based on several factors. The overall goal is to find a range of duration of action—short acting (e.g., 2-6 hrs), intermediate acting (e.g., 6 hr-1 day), and longer acting (e.g., 2-14 days). Also, dendribodies with high valency (high METH-binding capacity), solubility, and stability as demonstrated in vitro will be selected. The in vivo $t_{1/2}$ will largely be influenced by the molecular weight of the dendribodies and the hydrodynamic volume, however, there are many factors that will affect t½, (e.g., catabolism, renal clearance, etc.).

Subcutaneous infusions of METH will be used because this method produces the most stable pharmacokinetic parameters (by avoiding variables introduced due to intravascular mixing), maintains constant and consistent tissue levels for prolonged time periods, and allows for minimal handling of the rats (compared to frequent iv, sc, im, or ip injections). It also provides stable tissue baseline drug concentrations for determining the dendribody-induced changes. This study design will allow simultaneous determination of the ability of the new dendribodies to alter serum METH pharmacokinetics and the pharmacokinetics of the dendribodies themselves.

Dual venous cannulated rats will be divided into seven groups (6 rats/group). One group will receive vehicle, one will receive scFv4G9, and the other five will receive a different dendribody. The dose of the scFv4G9 and dendribodies will be equimolar in binding sites to the 3.2 mg/kg/day METH sc infusion. The dendrimer dosing will be based on the body burden of METH at 3.2 mg/kg/day at steady state and the molecular mass and valency of each individual dendribody (e.g. 36.56 mg/kg for unconjugated scFv4G9).

Subcutaneous osmotic mini pumps will be implanted and METH will be delivered at 3.2 mg/kg/day. The next day, after METH steady state has been reached, one group will receive vehicle, one unconjugated scFv4G9, and the other five groups will receive one of the five different dendribodies spiked with $1 \times 10^6$ dpm of a [$^3$H]-labeled form of the dendribody as a tracer. Blood sampling via the jugular catheter will adhere to the following schedule following administration of unconjugated scFv4G9 or dendribody: 1 min, 5 min, 10 min, 30 min, 1 hr, 2 hr, 4 hr, 8 hr, 24 hr and daily for up to 2 weeks, or until dendribody, or METH-dendribody binding is no longer detected. Serum samples will be analyzed for scFv4G9 or dendribody by SEC/scintillation spectrophotometry. Serum samples will be analyzed for METH and AMP by LC-MS/MS. Urine samples will be collected to determine renal elimination of METH, AMP and scFv4G9 or dendribody.

It is anticipated that METH, in the presence of dendribodies, will have a lower volume of distribution and reduced renal clearance (as measured by urine output) compared to untreated controls or scFv treated rats. Also, it is anticipated that the site-specific conjugated dendrimer with the PEO linker will have a longer half-life than lysine-specific conjugated scFv due to the hydrodynamic volume of the linker. However, because these are completely new antibody-nanoparticle entities, it is uncertain how they will be distributed (Vd) and eliminated (Cls). Early catabolism could play a big role in the longevity of these dendribodies, and again, the PEO linker could reduce the rate of catabolism. Since the outcome cannot precisely be predicted, it will be necessary to make and test several dendribody forms. Thus, these dendribodies are just the initial phase of the 2nd generation of anti-METH antibody medications, and the knowledge gained from these studies will be used to continually improve and customize their properties.

Sample Size/Time Table: n=6 rats per group×7 groups (saline, unconjugated scFv, and five unique dendribodies)+ 10 replacements if needed=52 rats required to substantiate data for each of the dendribodies. This number allows for 25% cannula failure, the most common failure event.

From the results of the pharmacokinetic and locomotor activity studies, three dendribodies will be selected, including one short acting (e.g., 2-6 hrs), one intermediate acting (e.g., 6 hr-1 day), and one longer acting (e.g., 2-14 days) to determine METH tissue concentration at selected time points. The dendribody effect on METH concentration in brain (due to the CNS effects of METH), heart (due to the cardiovascular effects of METH), and kidney (due to high elimination of drugs and small proteins) will be examined. Also, the dendribody concentration in the kidney at these selected time points will be examined to assess any unexpected accumulation. The dosing regimen will be selected based on the earlier outcomes of the pharmacokinetic and behavior studies. Then early, peak, and late time points will be selected in the behavioral response curve for tissue sampling to determine METH and dendribody concentrations. For example, for the shorter acting dendribody for overdose treatment, the time of effect might be from 5 minutes through 1 hr, with at peak of effect at 30 min. Thus, tissue would be collected at 10 min, 30 min, and 50 min.

Sample Size/Time Table: n=3 rats per time point×3 time points×4 groups (saline control, short, intermediate, and long acting dendribodies)+9 replacements if needed=45 rats. Due to the small variance in the tissue extraction and LC MS/MS methodologies, a sample size of three will be adequate and a good balance between data quality and the minimum number of animals used.

Example 24

Evaluate In Vivo Safety and Immunogenicity of Dendribodies in Rats

The scFv4G9 and dendribodies are expected to be safe since known anti-METH mAbs do not appear to bind to endogenous ligands, even at anti-METH IgG doses of 1,000 mg/kg. However, since the dendribodies are an entirely new therapeutic medication, safety parameters will be monitored closely. A series of evaluations will be performed to assess potential adverse effects, including toxicities inherent in the therapeutic medications, from possible contaminants or impurities, and from antibodies generated in response to the dendribodies. The METH concentration will be determined in selected organs (e.g., heart, liver, kidney, and spleen in addition to brain) in one-third of animals (randomly selected) used in pharmacokinetic studies. Other assays of specific organs or tissues will be dictated by findings of grossly identifiable pathology, infections, or organ disease. Special attention will be paid to lymphoid organs, like spleen and thymus, due to the possibility of immunotoxicity. In instances of organ involvement, histopathology of target organs will be performed by a pathologist.

All rats will be observed frequently and regularly for signs of toxicity and potential immunogenicity by: performing ELISAs with serum from rats at the end of PCKN experiment to determine titers (if any) against dendribodies, monitoring general health, measuring body weight, observing feeding behavior, measuring blood chemistries, weighing and inspecting organs when animals are euthanized at the end of each study, or if unexpected adverse effects are found.

Any evidence of untoward effects will be carefully evaluated for etiology. Necropsy and histopathology studies will be performed on animals that display possible toxicities. Scheduled specific assays of serum chemistry (hepatic and renal function) and hematology (complete blood counts and white cell differential analysis) will be performed in rats used in the pharmacokinetic studies to look for subclinical evidence of toxicity.

Example 25

Determine the Ability of Dendribodies to Alter the Locomotor Effects of METH

A primary indicator of pharmacological efficacy of the dendribodies as a METH antagonist will be their ability to alter the locomotor effects caused by METH. This is a straightforward approach and is well characterized in the literature (Riviere et al., 1999; Byrnes-Blake et al., 2003; Gentry et al., 2006). All rats (n=6 for each scFv4G9 or dendribody) will be subjected to 4 study sessions, which will be separated by 48-72 hr. Because of the behavioral sensitization, each group will receive two sessions of METH. On the morning of each study session, the rats will be placed in their study chambers. Behavior will be measured for 1 hr. The rats will then receive the following treatments in successive sessions: saline (to establish baseline locomotor activity), 1 mg/kg METH (to allow for sensitization, activity will not be recorded), 1 mg/kg METH (vehicle delivered 30 min later, equivolume to dendribody injection), 1 mg/kg METH followed 30 min later by the scFv4G9 or dendribody, equimolar in binding sites to the dose of METH given. Locomotor activity (distance traveled, number of rearing events and duration of activity) will be measured for up to 6 hr after METH dosing, or until effects are over. The locomotor effects will be measured using automated analysis of behavior with the EthoVision system (Noldus Information Technology; Sterling, Va.). This system uses digitized video tracking and motion analysis as a means of automated data acquisition. It is more efficient than manual rating, and it eliminates the problems of observer fatigue and bias. In addition, the digital recording system allows us to evaluate and quantify the presence of stereotypic behavior, such as head weaving, by visual analysis.

Sample Size/Time Table: n=6 rats per group×6 groups (scFv, and up to 5 unique dendribodies)+9 replacements if needed=45 rats required to substantiate data for each of the dendribodies. This number allows for 25% cannula failure, the most common failure event.

Example 26

Additional Methods and Materials

Study Animals: Male Sprague-Dawley rats with dual venous catheters (implanted at the vendor) will be used in Aim 3a. For behavioral studies (Aim 3c), Male Sprague-Dawley rats with single venous catheters will be used. Approximately one week after arrival, the rats will be habituated to individual testing chambers to minimize stimulation from extraneous noise and odors.

ScFv4G9 and scFv4G9-C cloning: After amplification by PCR, we will ligate DNA sequences into plasmid pGEM-3Z and transform *E. coli* strain DH5a for plasmid growth and maintenance. Sequencing of all DNA constructs will be performed by the UAMS DNA Sequencing Core Facility.

Bead-based radioimmunoassay: The RIA will be performed similarly to the method of Owens et al. (1988) with the following changes: a 20 µl aliquot containing 100 ng of purified scFv4G9 or scFv4G9-C will be incubated with 50,000 DPM of [$^3$H]-METH in the presence of varying concentrations of unlabeled METH. A 20 µl aliquot of a 50% slurry of TALON beads (Clontech, Mountain View, Calif.) in RIA buffer (0.05 M Tris pH 7.6, 150 mM NaCl, 2% BSA, 0.2% NaN3, 0.05% Tween-20) will be added, and the final volume will be adjusted to 220 µl with RIA buffer. The solutions will be incubated overnight at 4° C. with end-over-end rotation. The next day, the tubes will be centrifuged at 1,000×g, the beads washed twice with 1 ml of RIA buffer and resuspended in 2 ml scintillation fluid for quantitation by scintillation spectrophotometry.

Seed cultures: Seed cultures will be expanded in shake flasks, monitoring for cell density and health by microscopy using a hemocytometer. Once these cells have grown to a density of $5 \times 10^5$ to $1 \times 10^6$ per ml, the cells will be used to inoculate the large scale production media at ½0th of the large scale volume.

Large scale production of scFv: Cultures will be grown in a Wave bioreactor (4-10 L bioreactor bags) (GE Healthcare, Piscataway, N.J.), which will allow accurate monitoring and control of pH (typically between 7.1 and 7.4), dissolved oxygen, CO2, temperature and agitation. Feed medium composition and timing of feeds will be monitored (e.g. soy or other hydrolysates, glutamine, or glucose; feed on multiple days during culture; feeding based on metabolite data). Production of scFv4G9 will be monitored by performing small batch immobilized metal affinity chromatography (IMAC) followed by SDS-PAGE and A280 quantitation. The effect of temperature shift on total yield will be monitored. The timing of this shift can be important (e.g. shift on day 4 of the production run). The typical shift is from 37° C. down to 31° C. Samples will be taken daily to monitor scFv4G9 production. When productivity has ceased and cell viability has dropped, the culture media will be centrifuged in 500 ml centrifuge bottles, pooled and the clarified cell culture supernatant will be transferred to downstream process development.

ScFv purification: ScFv4G9 and scFv4G9-C will be purified by metal affinity chromatography using an AKTA Explorer 100 FPLC system and a HisPrep metal affinity column (GE Healthcare). Briefly, the column will be equilibrated with five column volumes of binding/wash buffer (20 mM NaPO4, pH 7.4, 500 mM NaCl, 20 mM imidazole) at 7 ml/min. The supernatant from the cell culture will be loaded onto the column and the unbound sample will be washed out with three column volumes of binding/wash buffer. The scFv4G9 will be eluted from the column with elution buffer (binding/wash buffer with 500 mM imidazole) and collected in 12 ml fractions. Fractions will be analyzed for scFv4G9 content by SDS-PAGE.

Non site-Specific crosslinking: 19.65 mg of PAMAM G3 dendrimer will be exchanged into activation buffer (0.1 M MES, pH 6.0, 0.5 M NaCl) using a PD-10 desalting column (GE Healthcare). After pooling fractions, EDC will be added to a concentration of 2 mM and then Sulfo-NHS to 5 mM, stabilizing the amine-reactive intermediate by converting it to an amine-reactive Sulfo-NHS ester. After dendrimer activation and desalting into administration buffer (0.5 M NaPO4, pH 7.4, 0.15 M NaCl), scFv4G9 will be added in a dendrimer:mAb molar ratio of 1:50, 1:100, and 1:200. Incubation will be allowed to proceed for 2 hrs with samples taken at 30 min, 1 hr, and 2 hr for SDS-PAGE and SEC analysis.

Size exclusion chromatography: SEC evaluation of dendrimer conjugations will be performed on an AKTA Basic FPLC (GE Healthcare) equipped with an AS 900 Autosampler, Frac 950 fraction collector, and a TSK-GEL G2000SWxl 30 cm size exclusion column (Toso Haas, Montgomeryville, Pa.). A 20 µl sample will be injected onto the column at 1 ml/min flow rate in MWS buffer (50 mM NaPO4, pH 6.7, 100 mM NaSO4) after equilibration. The column elution profile will be determined using size exclusion standards (Sigma, St. Louis, Mo.) consisting of blue dextran (2000 kDa, to determine void volume), R-amylase (200 kDa), bovine serum albumin (66 kDa), carbonic anhydrase (29 kDa), cytochrome C (12.4 kDa), and phenol red (to determine the column inclusion volume). Samples will be centrifuged at 20,000×g for 10 min prior to chromatography to remove any precipitated material or debris. Elution profiles for dendrimer and dendribodies will be monitored for UV absorption at 254 nm.

Ion exchange chromatography: Ion exchange purification will be performed on a AKTA Explorer FPLC equipped with a sample loading pump and Frac 950 fraction collector, and HiTrap Q-Sepharose or HiTrap S-Sepharose ion exchange columns (GE Healthcare). This chromatography system has the capability to automatically run pH and gradient scouting methods in small scale to determine the optimum purification procedure (e.g. linear or step salt gradients, optimal binding pH, and flow rate). Once small scale procedures have been determined, they will be applied to large scale purification of the dendribodies.

MALDI/MS TOF/TOF Analysis: According to the ASMSF, the samples will be dissolved in a suitable solvent to produce concentrations on the order of 0.01-0.1 mg/ml. A saturated solution of matrix will be prepared, typically dissolved in acetonitrile/water, although the facility also frequently uses dihydroxybenzoic acid. Sample (1 µl) and matrix (1 µl) will be mixed and allowed to dry on a MALDI target, typically a Bruker (Madison, Wis.) Anchor Chip which is essentially a treated sample of stainless steel. The sample/matrix mixture is allowed to dry to crystals, which are analyzed by MALDI/MS using a Bruker Ultraflex II TOF/TOF.

Reduction of free cysteine on scFv4G9-C: Since the protein production and purification process will expose the engineered cysteine to an oxidizing environment, it will be necessary to reduce the cysteine sulfhydryl to restore reactivity. Because homodimers of single chain antibody fragments can spontaneously form when a C-terminal free cysteine is engineered in the protein, another important consideration in conjugation reactions is ensuring that these cysteines are reduced and available for conjugation. The disulfide reductants to be tested for the ability to reverse this dimerization and reduce the C-terminal cysteine will be tris[2-carboxyethyl]phosphine (TCEP) and 2-mercaptoethylamine (MEA). These reductants can preferentially reduce the disulfide bonds between two antibody heavy chains while sparing the interchain and intrachain disulfides in the variable region in a concentration-dependent manner. The presence of reducing agents in a conjugation reaction can dramatically lower the efficiency of conjugation, due to competitive binding of the reductant to the conjugate. Therefore, conjugation of dendrimer to anti-METH scFv4G9-C will be carried out following reduction of the antibody and subsequent removal of the reducing agent using either an FPLC desalting column or immobilized reductant. These methods, as well as reduction trials with TCEP and MEA, will be compared for maximum yield of targeted thiol reduction. Maintenance of a reduced free cysteine will be monitored by absorbance using 5,5'-dithiobis(2-nitrobenzoic acid) (DTNB), or Ellman's reagent.

Thiol-specific crosslinking of dendrimer to scFv4G9-C: Initially, the manufacturer's protocol for a two-step conjugation reaction will be utilized, but individual parameters of the reaction will be modified (i.e., pH, crosslinker, dendrimer, and scFv4G9 concentration) to produce the highest yield. Briefly, the dendrimer will be exchanged into conjugation buffer (0.1 mM PBS, pH 7.2) by desalting or dialysis. Crosslinker will be added to the dendrimer to a final concentration of 10 to 100-fold excess (e.g., 1 mM crosslinker to 0.1 mM dendrimer). This reaction will proceed for 30 min to 2 hr at 4° C., with samples taken at 30 min irtervals for analysis by SDS-PAGE for crosslinking efficiency. After incubation, excess crosslinker will be removed by desalting the sample with conjugation buffer and the previously prepared scFv4G9-C will be added in experimentally determined molar excess, and the reaction will be allowed to proceed from 30 min to 2 hr, with samples taken every 30 min for SDS-PAGE analysis. These systematic studies will enable the determination of the best conjugation conditions for high scFv4G9 to dendrimer ratios (multivalency) as well as conditions that produce the highest yield of dendribody.

Protein formulation for in vivo experiments: After purification and in vitro characterization, the dendribodies will be formulated for in vivo administration in rats. The purified preparations will be concentrated and exchanged into endotoxin-free antibody administration buffer (0.15 M NaPO4, pH 7.4, 0.1 M NaCl) with an Amicon stirred concentrator equipped with a filter membrane of an appropriate MWCO for the size of the dendribody (e.g. 30-100 kDa MWCO). After concentration and buffer exchange, the formulated dendribody will also be ultracentrifuged to remove any aggregated products and will be tested for endotoxins.

Equilibrium dialysis: The dendribodies will be tested for retention of METH binding properties. Since the sites of conjugation are distal to the binding site of the antibody, changes in binding or specificity are not anticipated, but equilibrium dialysis will be performed as described in (Proksch et al., 2000) on each construct made to elucidate any changes in affinity or specificity of the conjugated antibody.

[$^3$H]-labeling of scFv4G9 and dendribody: An aliquot of each final product will be radiolabelled for use in pharmacokinetic experiments. [$^3$H]-dendribodies will be synthesized similarly to a previous method for radiolabeling anti-METH scFv6H4 and anti-PCP Fab (McClurkan et al., 1993; Peterson et al., 2008) using 4.4 mg of dendribody and labeling with [$^3$H]-NSP (250 NCi, GE Healthcare, Piscataway, N.J.). After labeling, [$^3$H]-product will be separated from unincorporated [3H]-NSP by SEC and dialyzed into administration buffer.

Dendribody and METH PCKN studies: All serum pharmacokinetic experiments will consist of 6 rats per treatment group. For METH and scFv4G9 and dendribody PCKN studies, adult male Sprague-Dawley rats (~250 g) will be purchased from Charles River Laboratories (Raleigh, N.C.) with surgically implanted dual jugular vein catheters (silastic medical-grade tubing, 0.020 in inner diameter and 0.037 in outer diameter; Dow Corning, Midland, Mich.) that will be used for drug administration and blood sampling, respectively. Catheters are placed in the subcutaneous tissue for transport from the vendor and will be kept there until the day before the first experimental procedure, when catheters will be exposed under halothane anesthesia. Catheter patency will be maintained by daily injection of saline, followed by sterile glycerol containing 25 U of heparin. Animals will be housed individually in a light-controlled environment (12 hr light/dark cycle). They will receive water ad libitum and will be fed approximately 20 g of food pellets daily, to maintain their body weights between 250-280 g.

On Day −2 of the study (i.e., 2 days prior to METH dosing), pre-METH blood samples (100 µl) will be taken and the rats will be implanted with Alzet 2 week microosmotic pumps (Durect Corp, Cupertino, Calif.) delivering 3.2 mg/kg/day METH. On Day −1, blood samples (100 µl) will be taken at 10 am, 1 pm and 5 pm to allow determination of METH control steady-state concentrations. On Day 0, the rats will be given either anti-METH scFv4G9, dendribody or an equal volume of buffer without dendribody (controls) via the left jugular catheter. Immediately following administration of the scFv4G9, dendribody, or buffer, blood samples (100 µl) will be taken at various time points via the right jugular catheter. Following each blood collection, the catheter will be filled with glycerol, or heparinized glycerol if the time between blood collections is greater than 2 hr. The catheter solution will be removed prior to collection of the next sample to prevent volume dilution of the blood sample. Because of our very sensitive analytical methods we expected to collect a total of only 5-8% of the total blood volume of a rat in a 24 hr period.

Analysis of drug concentrations in serum and brain samples will be accomplished by LC-MS/MS. Data will be analyzed using Win-Nonlin software as previously described (Riviere et al., 1999; Byrnes-Blake et al., 2003). The following pharmacokinetic parameters will be determined: steady-state drug concentration (Css), elimination half-life ($t_{1/2\lambda z}$), clearance (Cls), and the volume of distribution at steady state (Vss).

Serum sampling for PCKN studies: Samples will be allowed to clot at room temperature and then centrifuged for collection of serum. Urine samples will be collected until elimination is over 90% complete. Serum and urine samples will be analyzed for METH and AMP by LC-MS/MS. As part of these experiments, METH protein binding in the serum samples by equilibrium dialysis will be evaluated.

Blood to serum ratios: Blood to serum ratios of scFv4G9 and dendribodies will be determined using blood samples collected during the PCKN studies. The blood samples will be collected and a small aliquot of whole blood will be immediately used to determine the hematocrit in heparinized hematocrit tubes by standard procedures. Duplicate whole blood samples (10 µl) will then be added to scintillation fluid and the [$^3$H]-tracer concentration will be determined by liquid scintillation spectrophotometry. After centrifugation of the remaining blood, duplicate 10 µl aliquots of the serum will be used to determine the [$^3$H]-tracer concentration in serum, as just described for the whole blood. The ratio of the concentration in the whole blood to the concentration in the serum (the blood to serum ratio) will be used to represent the distribution of dendribody between red blood cells and serum.

Determination of the concentration of dendribody in serum: The concentration of [$^3$H]-dendribody tracer in serum and urine samples will be determined by SEC similar to a previously described method (Proksch et al., 1998; Peterson et al., 2008). For the analysis of [$^3$H]-dendrimer protein concentrations, a TSK-GEL G2000SWxl 30 cm size exclusion column (TosoHaas, Montgomeryville, Pa.) will be connected to a Waters HPLC system (Waters, Corp., Milford, Mass.) consisting of an autoinjector in series with a multi-solvent delivery system, a UV absorbance detector and a fraction collector. The Empower software package (Waters Corp.) will be used to control the HPLC system and to collect all HPLC chromatography data. The column will be equilibrated with buffer (50 mM NaPO4, pH 6.7, 100 mM NaSO4) at a flow rate of 1 ml/min. The column elution profile will be determined using size exclusion standards as in METHOD 8. The UV Abs280 will be used to detect the real-time elution of serum proteins in each sample. Reproducibility will be monitored using blank serum and urine samples spiked with a known amount of [$^3$H]-dendribody tracer. These quality control samples will be analyzed with each batch of urine and serum samples. Liquid scintillation spectrophotometry will be used to quantitate the radioactivity in each 0.25 ml HPLC fraction. The concentration of dendribody will be calculated from the ratio of [$^3$H]-dendribody tracer:dendribody injected dose values.

Analytical LC-MS/MS methodologies for the quantitation of METH and AMP in rat serum and tissues: Current, published methodologies will be used to evaluate (+)METH and (+)AMP serum pharmacokinetics in the presence of new anti-METH scFv4G9 and dendribodies. Briefly, the drug will be extracted from samples using solid-phase extraction and then perform reversed-phase high-performance liquid chromatography (HPLC) on the extracted sample and the compounds of interest will be quantitated using tandem mass spectrometry. Typically, the on-column. The triple-quadrupole mass spectrometer (Waters Incorporated) will be operated using positive-ion electrospray ionization. Detection of (+)METH and (+)AMP is accomplished with mass spectrometry in multiple-reaction-monitoring mode using m/z transitions of 150 119 and 136-119, respectively. Samples (25 μl) will be quantitated using (±) -amphetamine-d11 as the internal standard. The lower limits of quantitation for (+)METH and (+)AMP are 0.3 ng/ml using 100 μl of serum and the linear dynamic range of the analytical method is 0.3-1000 ng/ml. The accuracy of the method is ±15% of the actual values and the within-day and between-day precision is <17% (RSD %).

Safety studies: Blood samples for chemistry and hematology studies will be collected when rats are sacrificed. Possible liver injury will be assessed with serum alanine aminotransferase (ALT) and aspartate aminotransferase (AST) levels, and kidney function will be monitored with blood urea nitrogen (BUN) and creatinine levels. Effects of dendribodies on hematologic function will be assessed with complete blood and automated white cell differential counts if adverse side effects are noted in any rats.

Antigenicity studies: ELISA will be used to test for the presence of rat antibodies against anti-METH dendribodies in randomly selected animals from the pharmacokinetic experiments as described previously (Proksch et al., 1998). Briefly, preimmune serum will be obtained from rats before the experiment as a negative control. Then serum will be taken from the same rats immediately following and 2 weeks after the end of the experiment. For a positive control in the ELISAs, several commercially available anti-mouse IgG antibodies (whole molecule or variable region specific) will be screened to find one that recognizes scFv4G9.

Locomotor studies: These experiments will be performed essentially as described previously (Byrnes-Blake et al., 2003). One week before the experiments, rats will be placed in the study chambers (60×45×40 cm, l×w×h) daily for 4-6 hr to allow habituation. On each experimental day, the rats will be placed in the chamber 1 hr before the administration of METH to acclimatize them to their surroundings. The rats will receive 1 mg/kg METH iv per day in a 1 ml/kg volume in a 15 sec injection 30 min prior to anti-METH scFv4G9, dendribody, or saline injections. The subjects will be recorded for 500 min. The parameters—distance traveled, number of rearing events and duration of activity—will be individually quantified for each animal. The distance traveled (in cm) and numbers of rearing events will be quantified in 2 min time intervals and totaled from the time of antibody administration until the pharmacological effects return to baseline levels. Locomotor activity will be considered to have returned to baseline when the first of two consecutive 4 min time intervals are equal to or below the mean±1 S.D. of the 30 min baseline prior to drug administration.

Data analysis and statistics: Pharmacokinetic analyses of concentration-time data will be conducted using both model-dependent and model-independent methods with WinNonlin software (Pharsight Corporation, Mountain View, Calif.). For model-dependent pharmacokinetic analysis, exponential curves (2 and 3 compartment models) with a first-order input function will be fit to the average concentration-time data sets using appropriate weighting functions. The best-fit line will be selected after visual inspection of the fit of each curve to the data, analysis of the residuals, and assessment of the statistical variance for each pharmacokinetic parameter.

For all experiments, statistical significance will be considered to be achieved at a level of $P<0.05$. A Student's two-tailed t test will be used when comparing two means (e.g., pharmacokinetic values for METH with and without anti-METH scFv or dendribody treatment). When multiple comparisons are required, one- or two-way analysis of variance (ANOVA) will be performed as appropriate. Repeated measures ANOVA will be used when animals receive multiple treatments. For post-hoc analysis, a Student-Newman-Keuls test will be used when all pair-wise comparisons are made. A Dunnett's test will be used when comparing all treatments to a control.

Example 27

Figure 23A:
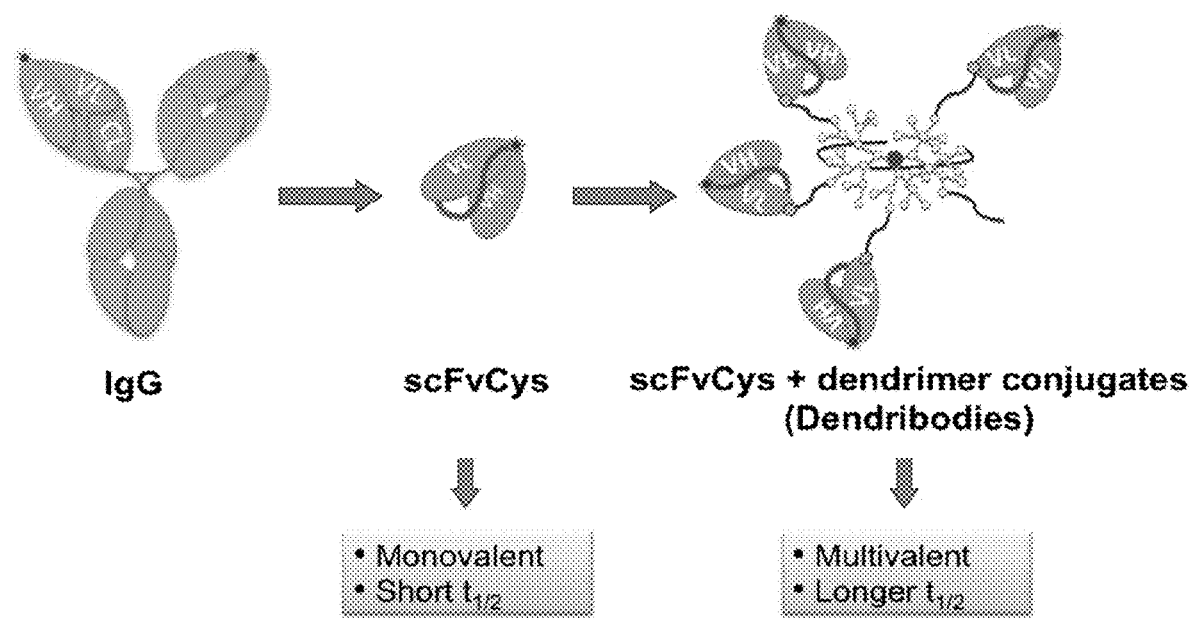
FIG. 23A, FIG. 23B, FIG. 23C and FIG. 23D depict a schematic illustration of dendrimer formation and a graph and SDS-PAGE gel of dendrimer purification.
Figure 23B:
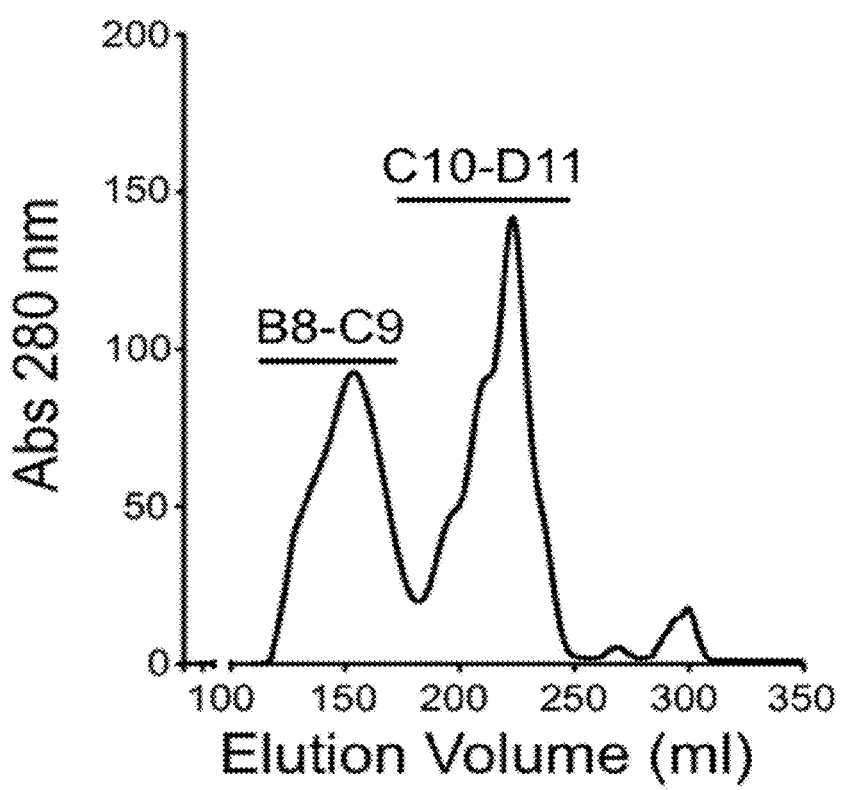
Figure 23C:
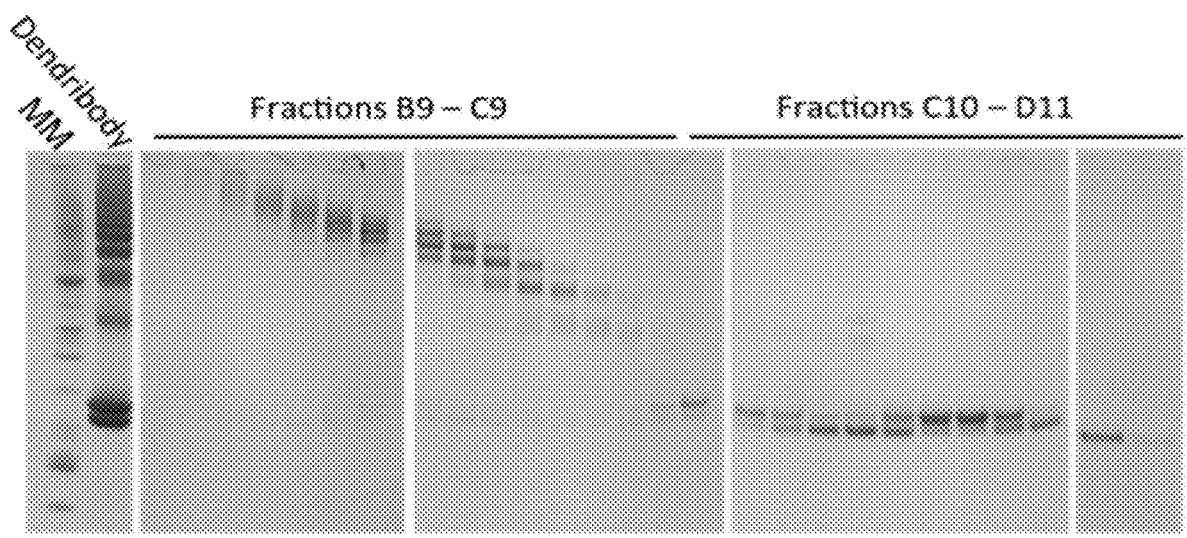
Figure 23D:
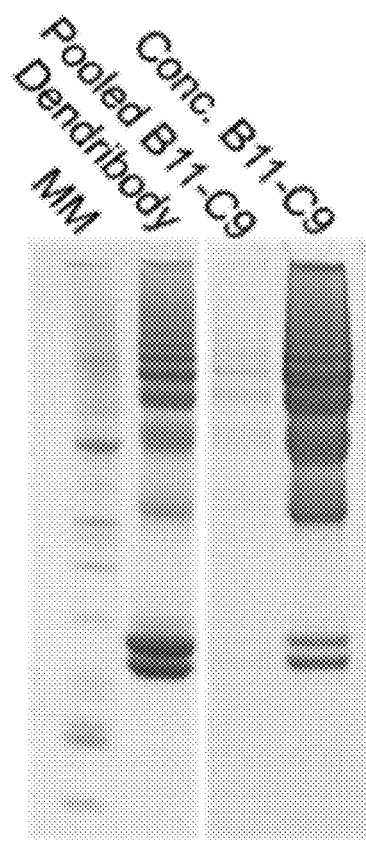

Production and In Vitro and In Vivo Characterization of Unconjugated scFv7F9Cys and scFv7F9Cys-Based Dendribodies Using methods described in the Examples above herein, an additional mAb (mAb7F9), and a scFv7F9Cys antibody fragment with high affinity for METH was generated (Stevens et al., 2013 mAbs 6(2):547-555). The scFv7F9Cys antibody fragment was then conjugated to G3PAMAM to generate a dendribody comprising the scFv7F9Cys antibody fragment. A short acting anti-METH scFv7F9Cys fragment was engineered from the IgG form of the mAb7F9. The scFv7F9Cys was then conjugated to the PEGylated dendrimer to generate long acting dendribodies as described in the Examples above and depicted in FIG. 23A. scFv7F9Cys dendribodies were separated via affinity chromatography from unreacted scFv7F9Cys (FIG. 23B) and the various fractions were run on an SDS-PAGE gel. Fractions B8-C9 represent dendribodies and fractions C10-D1 represent PEGylated and unreacted scFv7F9Cys (FIG. 23C). To further analyze the dendribodies, pooled and concentrated fractions B11-C9 were run on an SDS-PAGE gel (FIG. 23D).

Figure 24A:
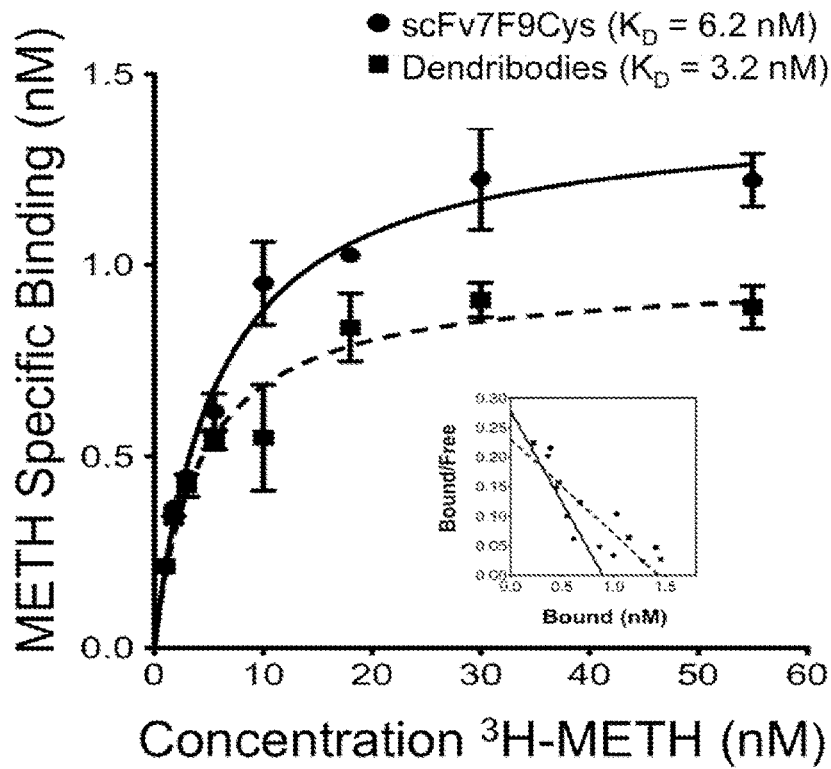
FIG. 24A, FIG. 24B and FIG. 24C depict graphs of binding kinetics of scFv7F9Cys and dendribodies and hemolysis of erythrocytes in the presence of dendribodies.
Figure 24B:
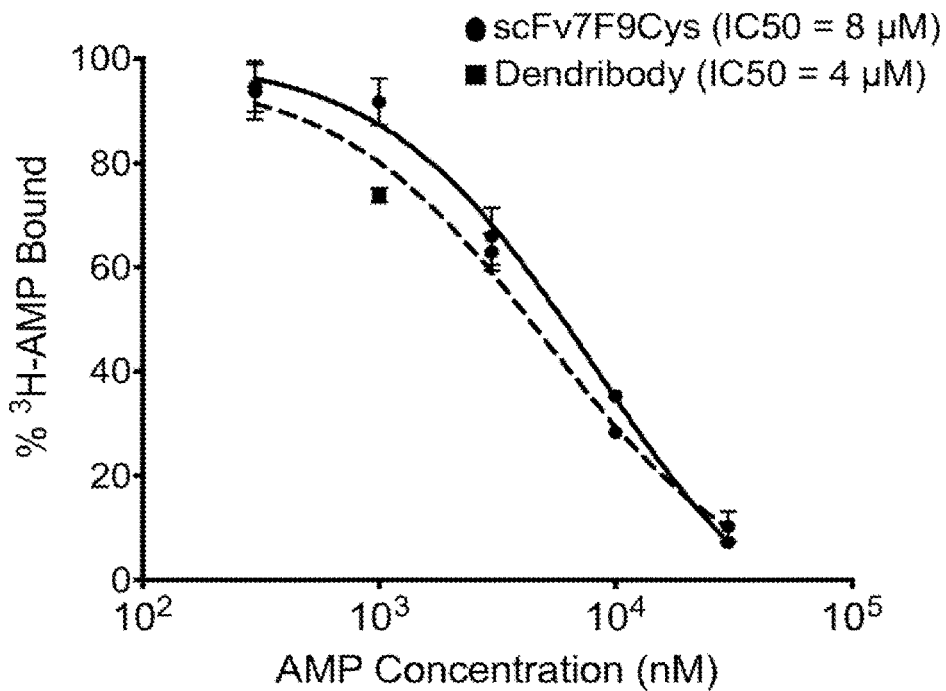

For initial in vitro functional testing of the dendribodies, a saturation binding equilibrium dialysis assay was performed. To determine if the dendribodies retained METH-binding function (capacity and affinity), a saturation binding equilibrium dialysis experiment was performed using a scFv7F9Cys and dendribody concentration capable of binding $^3$H-METH solution. The absolute affinities of the unreacted scFv7F9Cys and the purified lower-order dendribodies were compared. The affinities, as measured by the dissociation constant (KD) of the dendribodies and scFv7F9Cys to $^3$H-METH, were 3.2 nM and 6.2 nM, respectively (FIG. 24A). The scFv7F9Cys retained its affinity for METH in the conjugated form, indicating that the conjugation process had little effect on the binding pocket of the protein. To determine the affinity of scFv7F9Cys and dendribodies for amphetamine (AMP), and in vitro competition binding assay was performed. The $IC_{50}$ of the scFv7F9Cys and dendribodies were 8 and 4 µM, respectively (FIG. 24B). These results indicate that upon conjugation to dendrimer nanoparticles, an increase in scFv7F9Cys affinity for METH and AMP was seen.

Figure 24C:
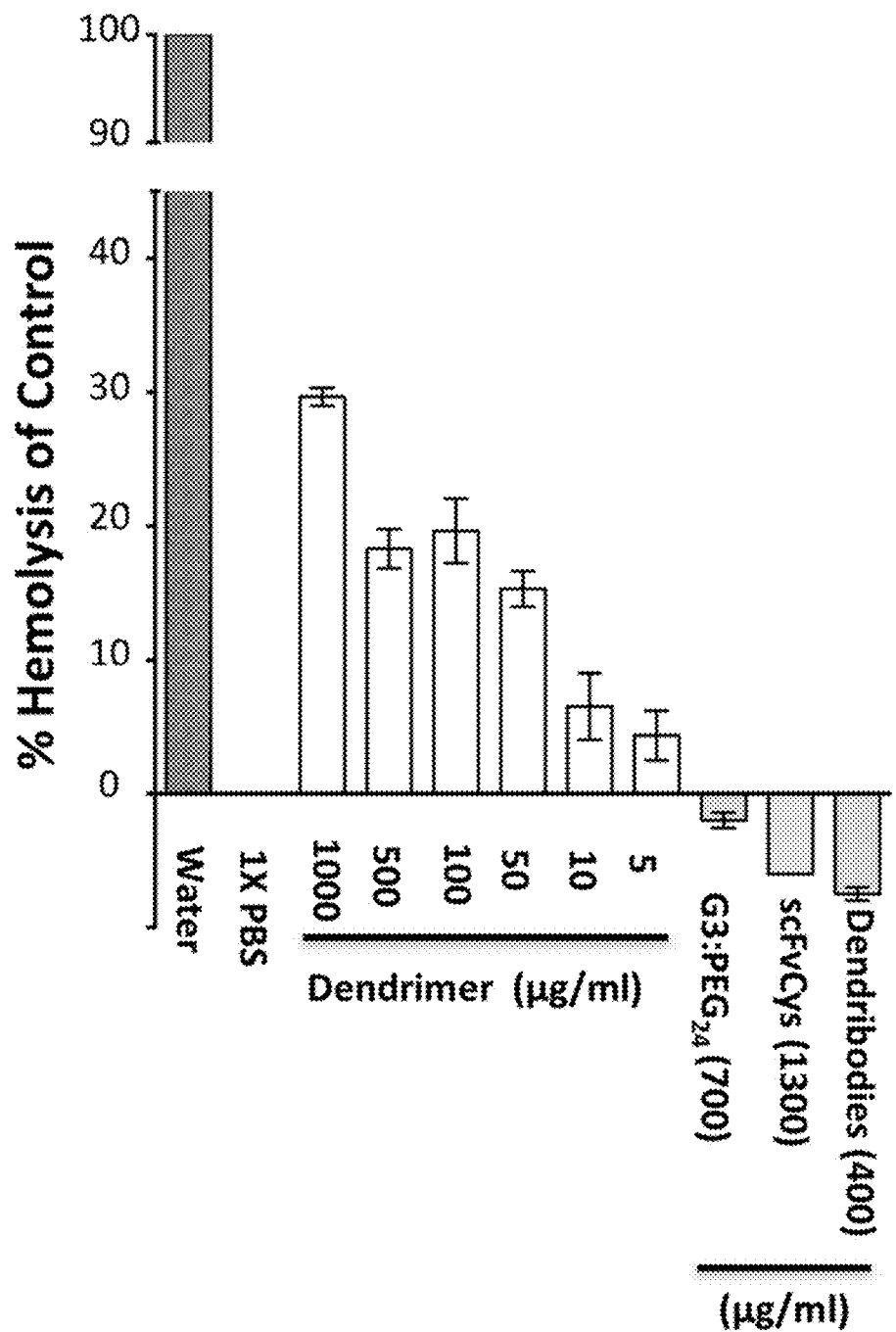

An in vitro hemolysis assay was performed to determine the effect of the dendribodies on erythrocytes. G3 PAMAM dendrimers exhibit concentration dependent hemolysis, whereas PEGylated dendrimers, unconjugated scFvCys and dendribodies are non-hemolytic. PEG functionalization protects the erythrocytes from hemolysis better than control buffer (PBS) (FIG. 24C).

Figure 21A:
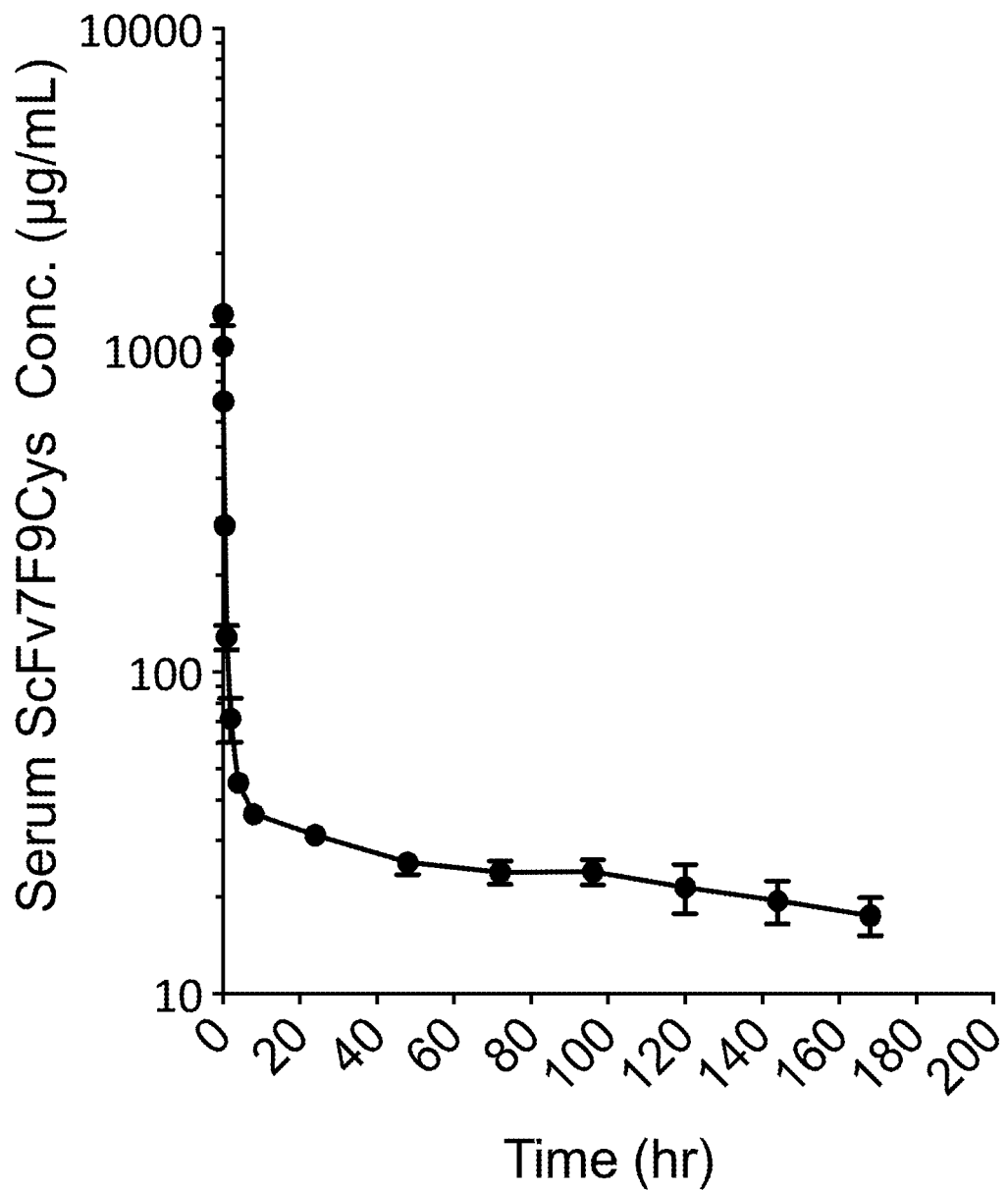
FIG. 21A and FIG. 21B graphically depict the pharmacokinetic properties of unconjugated scFv7F9Cys antibody in serum (FIG. 21A), and urine (FIG. 21B).
Figure 21B:
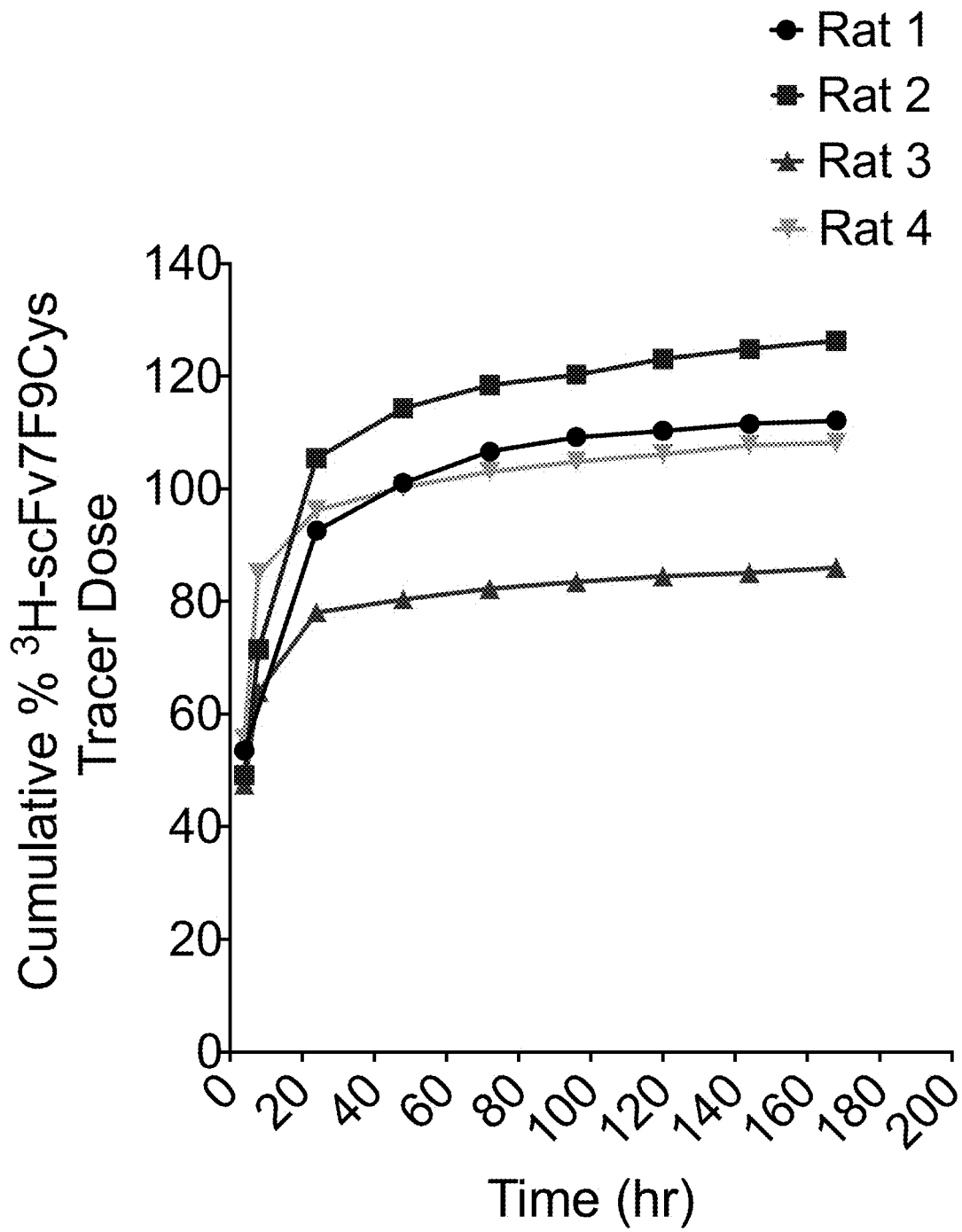

The pharmacokinetic profile of unconjugated scFv7F9Cys antibody was assessed. Analysis of serum samples from each time point showed that around 94% of the scFv7F9Cys was eliminated from the serum within 120 minutes of administration (FIG. 21A). In the urine, 50% of the injected dose of $^3$H-scFv7F9Cys accumulated in the urine within 240 minutes (4 hrs), which was the earliest point of urine collection (FIG. 21B). This analysis indicates that the serum $_{t1/2}$ of the unconjugated scFv7F9Cys is significantly less than 400 minutes, and closer to 100 minutes. This estimation is in agreement with the previously determined half-life of the anti-METH scFv6H4 monomers and multimers ($t_{1/2}$=5 and 280 min, respectively) described in the Examples above.

Figure 22A:
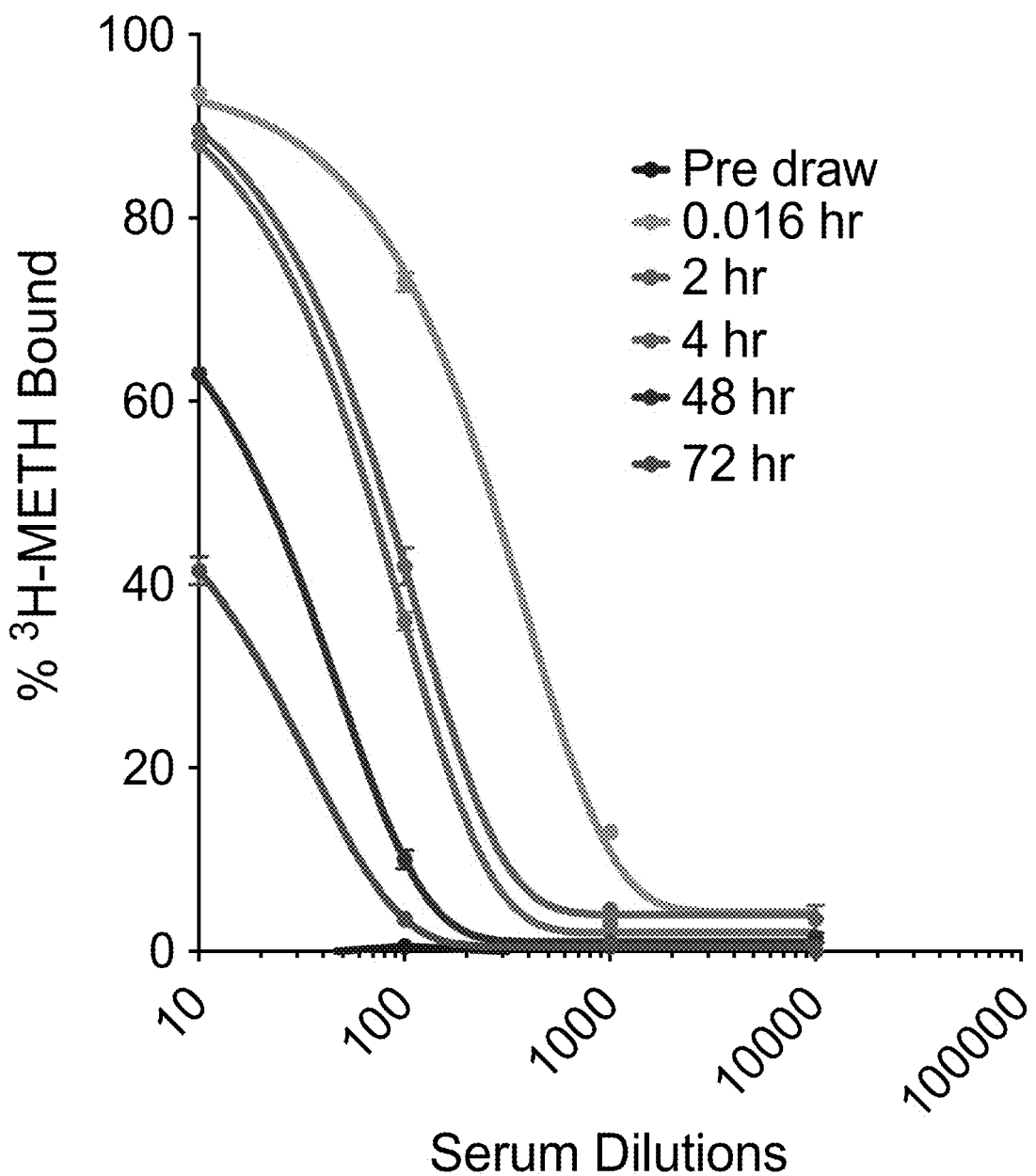
FIG. 22A and FIG. 22B graphically depict the pharmacokinetic properties of scFv7F9Cys-based dendribodies in serum over a 72 hr period (FIG. 22A), and % METH bound by the scFv7F9Cys-based dendribodies over the same period of time (FIG. 22B).
Figure 22B:
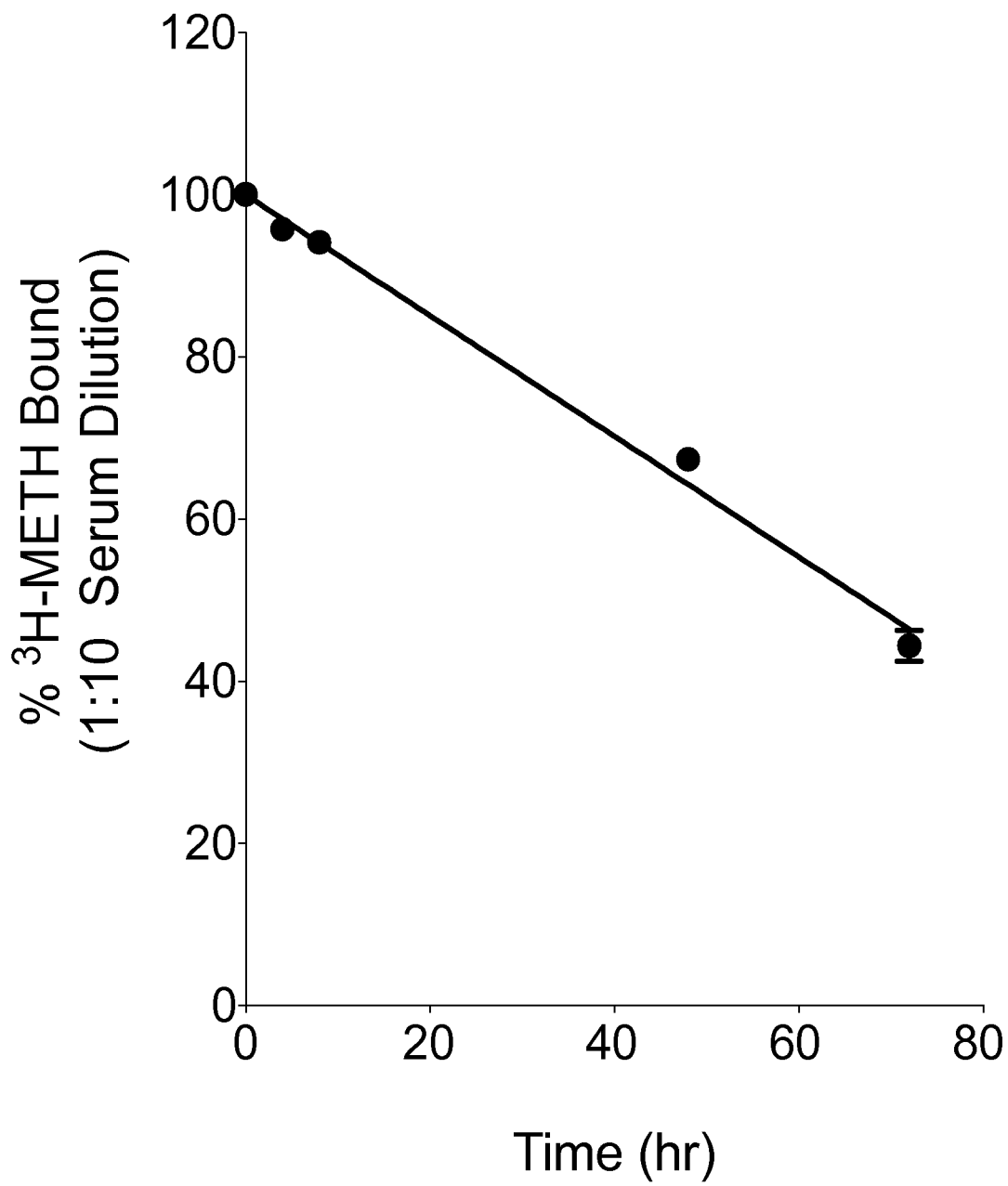

The pharmacokinetic profile of scFv7F9Cys-based dendribodies was also assessed. In short, scFv7F9Cys-based dendribodies were delivered intravenously to a male Sprague-Dawley rat and serum samples were collected over the course of 72 hrs. To determine the METH binding activity, serum titrations were performed in an equilibrium dialysis $^3$H-METH binding assay (FIG. 22A). The active scFv7F9Cys was present in the serum samples over the entire 72 hr collection period. More importantly, the normalized data indicated that the serum was still able to bind 50% as much $^3$H-METH as the 1 min (0.016 hr) time point (FIG. 22B). This suggests a significant and dramatic increase in half-life over the unconjugated scFv7F9Cys was achieved by converting to dendribodies. This data demonstrate that the dendribody design may be a potential platform for generating multivalent products from antibody fragments with customizable pharmacokinetic profiles.

Figure 25A:
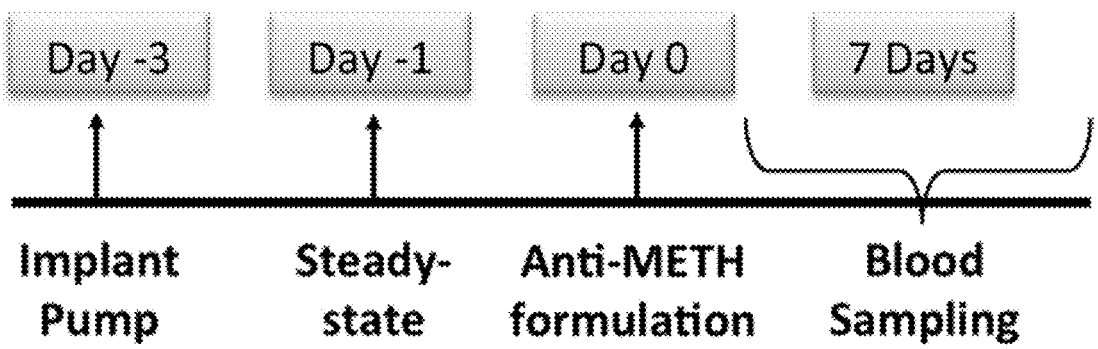
FIG. 25A and FIG. 25B depict a schematic illustration of the experimental design and a graph of the serum concentration over time of scFv7F9Cys and dendribodies.
Figure 25B:
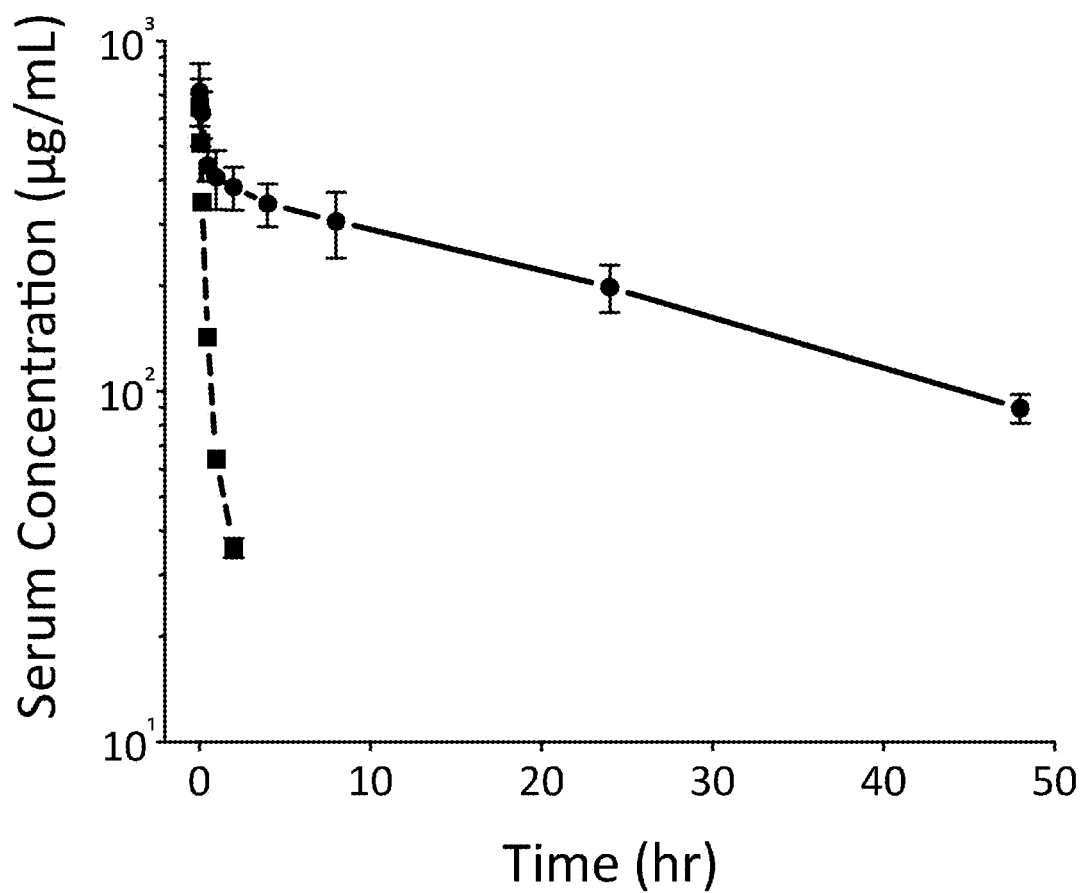

To determine the ability of anti-METH scFv759 to alter serum concentration of METH, subcutaneous osmotic mini pumps were implanted to deliver METH at 3.2 mg/kg/day (FIG. 25A). FIG. 25B depicts the concentration-time profile of anti-METH scFv7F9Cys and dendribodies after i.v. bolus dosing. The total amount of antibody (µg/ml) in the serum was calculated based on the ratio of dose to radiolabeled protein dose (DPM). These data indicated that the monomer had a $t_{1/2\lambda z}$ of 1.3±0.3 h (Table 4). The multimeric forms of scFv7F9Cys exhibited a much longer serum kinetic profile. The dendribodies had a $t_{1/2\lambda z}$ of 26±2.6 h (Table 4). See Table 4 for additional pharmacokinetic parameters.

TABLE 4

Serum PCKN Parameters of scFv7F9

| PCKN Parameter ± S.D. | scFv7F9Cys | Dendribodies | Fold Change |
|---|---|---|---|
| $t_{1/2\lambda z}$ (hr) | 1.3 ± 0.3 | 26 ± 2.6 | ↑20 |
| Cls (ml/min/kg) | 2 ± 0.1 | 0.044 ± 0.0034 | ↓45 |
| Vd (ml/kg) | 152 ± 26.3 | 98 ± 6.4 | ↓1.6 |

Figure 27:
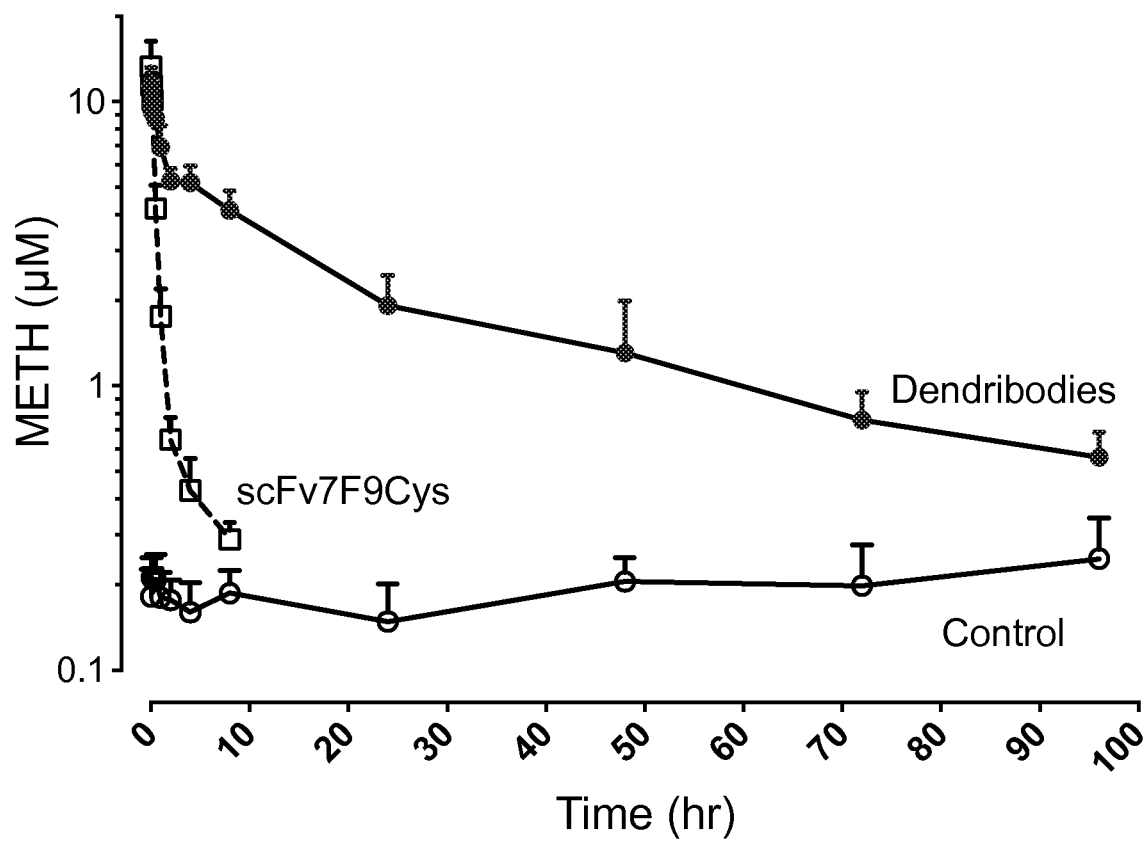
FIG. 27 depicts a graph of the average concentration versus time profiles for METH in serum with scFv7F9Cys (open squares), dendribodies (closed circles) or with a control injection of vehicle (open circles) administered at t=0 min. All groups of rats (n=6 per group) received a s.c. METH infusion of 3.2 mg/kg/day. All values are represented as the mean±SEM per time point. scFv7F9Cys and dendribodies redistributed METH to the central compartment to cause an immediate increase in the METH concentrations. However, the dendribodies maintained higher serum METH concentrations for 48 hr compared to 2 hr by xcFv7F9Cys.

In a further experiment, the average concentration versus time profiles for METH in serum was assessed with scFv7F9Cys, dendribodies or control were administered. All groups of rats (n=6 per group) received a subcutaneous METH infusion of 3.2 mg/kg/day. The scFv7F9Cys and dendribodies redistributed METH to the central compartment to cause an immediate increase in the METH concentrations (FIG. 27). However, the dendribodies maintained higher serum METH concentrations for 48 hours compared to 2 hours by the scFv7F9Cys.

Figure 26A:
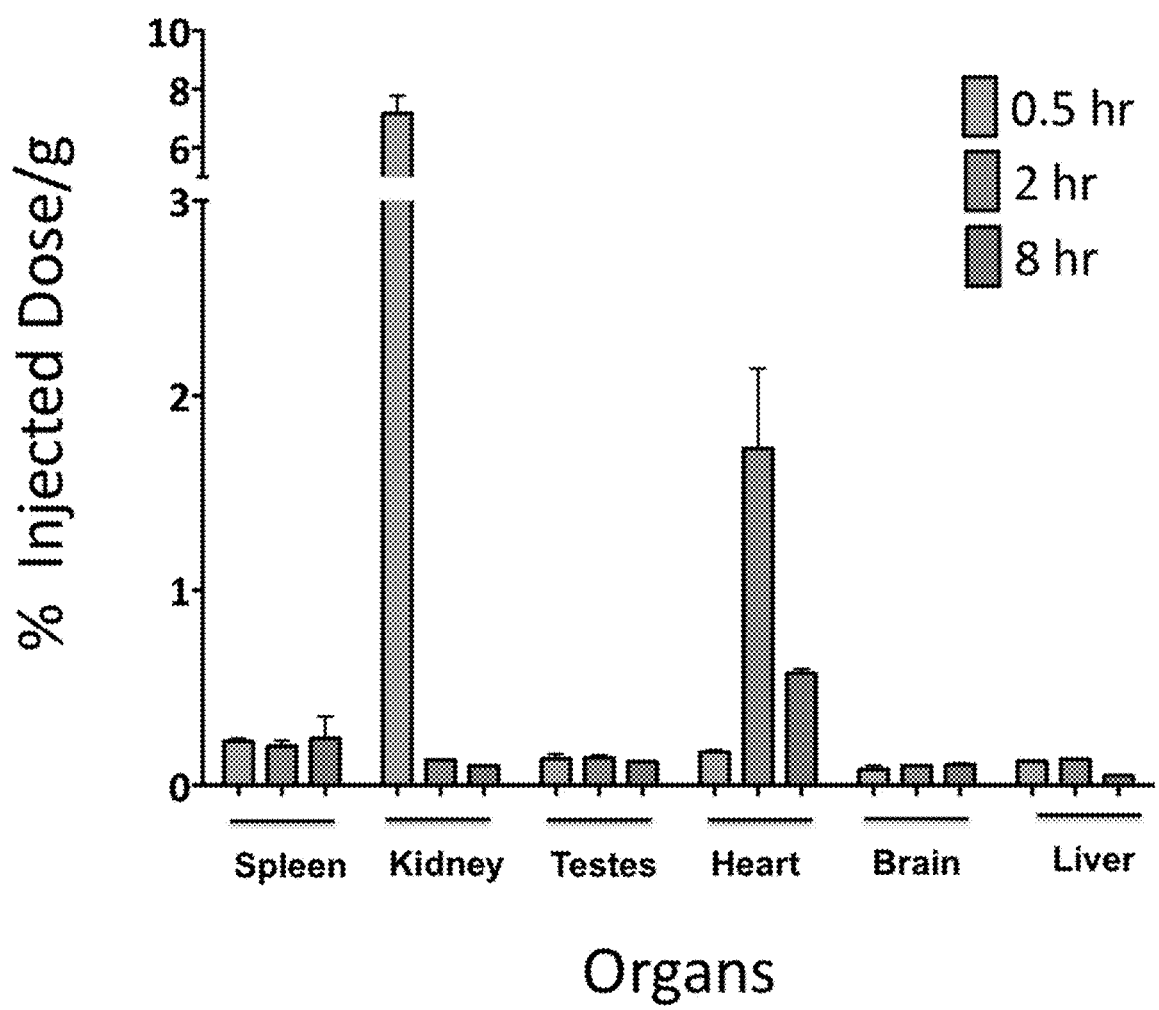
FIG. 26A, FIG. 26B and FIG. 26C depict graphs of the organ distribution of scFv7F9Cys and dendribodies.
Figure 26B:
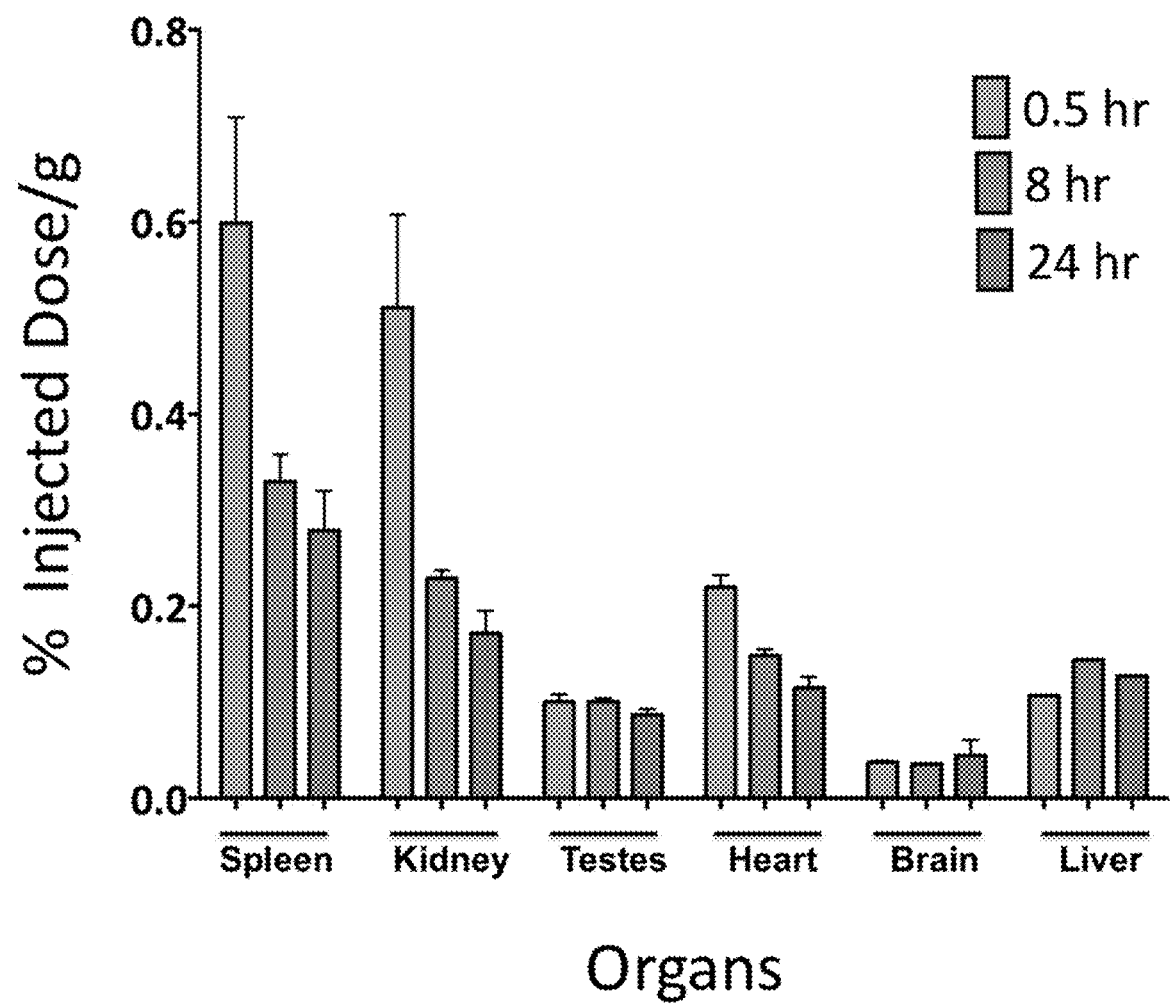
Figure 26C:
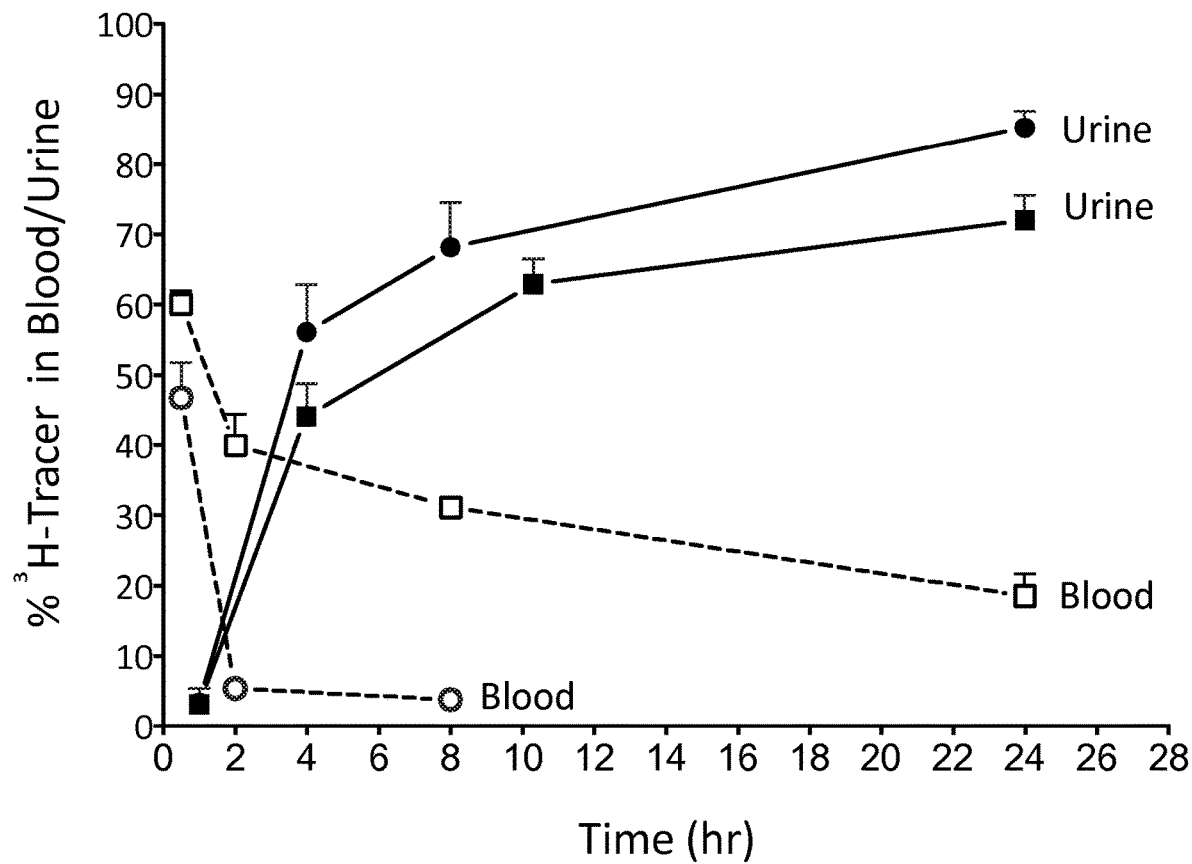

The organ distribution of scFv7F9Cys in male Sprague Dawley rats at three time points (0.5, 2 and 8 hours post-injection) was assessed. Two mice per time point were utilized. Data is depicted as the percent injected dose recovered per gram of organ (% ID/g) (FIG. 26A). Also, the organ distribution of scFv7F9Cys dendribodies in male Sprague Dawley rats at three time points (0.5, 2 and 8 hours post-injection) was assessed (FIG. 26B). Further, distribution of scFv7F9Cys and dendribodies in blood and urine is shown. Blood circulation and urine profile of $^3$H-tracer is shown as cumulative dose in blood and urine over time (FIG. 26C). Overall, the organ distribution and % $^3$H-tracer in blood and urine data for scFv7F9Cys and dendribody group agrees well with the estimated pharmacokinetic parameters. Renal clearance appears to be the major route of elimination for both the groups.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

What is claimed is:

1. A method of antagonizing the effects of amphetamine and amphetamine-like compounds in a subject, the method comprising administering to the subject an antibody composition comprising:
   a. a single chain antibody that binds an amphetamine compound;
   b. a nanoparticle, wherein the nanoparticle is a PEG modified poly(amidoamine) PAMAM dendrimer wherein the dendrimer conjugates two or more single chain antibody fragments and resulting dendribodies are multivalent; and,
   c. a crosslinker wherein the antibody composition antagonizes the effects of the amphetamine compound by binding the compound and maintaining the compound in the serum at higher concentrations relative to a corresponding unconjugated antibody, wherein the antibody composition has a longer in vivo serum half-life when compared to a composition comprising a corresponding unconjugated single chain antibody and wherein the antibody composition still displays at least 30% binding activity in the subject at 72 hours after administration, when compared to binding activity of the antibody composition at 1 minute after administration.

2. The method of claim 1, wherein the subject is selected from the group comprising a rodent, a non-human primate, and a human.

3. The method of claim 1, wherein the amphetamine-like compound is selected from the group consisting of (+)amphetamine, (+)methamphetamine, (+)3,4-methylenedioxymethamphetamine, and combinations thereof.

4. The method of claim 1, wherein the single chain antibody does not include an FcRn binding site.

5. The method of claim 1, wherein the single chain antibody does not include an effector region.

6. The method of claim 1, wherein the single chain antibody comprises a terminal cysteine.

7. The method of claim 1, wherein the single chain antibody is conjugated to the nanoparticle via the crosslinker.

8. The method of claim 1, wherein a plurality of single chain antibodies are conjugated to a single nanoparticle.

* * * * *